US012805863B2

(12) United States Patent
Rivard et al.

(10) Patent No.: US 12,805,863 B2
(45) Date of Patent: Nov. 24, 2026

(54) SMART CIRCULAR STAPLERS

(71) Applicant: Cilag GmbH International, Zug (CH)

(72) Inventors: Monica L. Z. Rivard, Cincinnati, OH (US); Christopher A. Denzinger, Cincinnati, OH (US); Leonardo N. Rossoni, Rahway, NJ (US); Nohemi C. Wells, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/202,531

(22) Filed: May 26, 2023

(65) Prior Publication Data

US 2023/0404572 A1 Dec. 21, 2023

Related U.S. Application Data

(60) Provisional application No. 63/353,279, filed on Jun. 17, 2022.

(51) Int. Cl.
*A61B 17/068* (2006.01)

(52) U.S. Cl.
CPC .................................. *A61B 17/068* (2013.01)

(58) Field of Classification Search
CPC ....... A61B 17/068; A61B 34/37; A61B 34/76; A61B 90/361; A61B 2017/00119; A61B 2017/00128; A61B 34/20; A61B 90/36; A61B 2017/00017; A61B 2017/00221; A61B 2017/00809; A61B 2090/064; A61B 2090/066; A61B 2090/0811; A61B 2090/365; A61B 2090/502; A61B 17/1155; G16H 20/40; G16H 30/40; G16H 40/63; G16H 40/67; G16H 50/20; G16H 50/50
USPC ................................ 227/175.1–182.1, 8, 19
See application file for complete search history.

(56) References Cited

U.S. PATENT DOCUMENTS

| | | | | |
|---|---|---|---|---|
| 4,008,523 | A * | 2/1977 | von Voros | G01B 3/205 33/784 |
| 7,747,311 | B2 * | 6/2010 | Quaid, III | A61B 34/74 345/157 |
| 8,066,167 | B2 | 11/2011 | Measamer et al. | |
| 8,353,438 | B2 | 1/2013 | Baxter, III et al. | |
| 8,622,275 | B2 | 1/2014 | Baxter, III et al. | |
| 8,672,207 | B2 | 3/2014 | Shelton, IV et al. | |
| 8,801,734 | B2 | 8/2014 | Shelton, IV et al. | |

(Continued)

FOREIGN PATENT DOCUMENTS

| | | | | |
|---|---|---|---|---|
| CA | 2699134 | A1 * | 10/2010 | A61B 17/07207 |
| EP | 3108823 | A2 * | 12/2016 | A61B 17/1155 |

(Continued)

*Primary Examiner* — Robert F Long
(74) *Attorney, Agent, or Firm* — Vorys, Sater, Seymour and Pease LLP; D. Jeremy Harrison

(57) ABSTRACT

A surgical stapler is disclosed comprising an end effector configured to receive a staple cartridge, a trocar movable relative to the end effector, an anvil removably coupleable to the trocar, a sensor, a housing comprising a display, and a control circuit operably coupled to the sensor and the display. The anvil is movable relative to the end effector based on movement of the trocar. The sensor is configured to sense a position of the anvil relative to the end effector. The control circuit is configured to interrogate the sensor to determine the position of the anvil and display a representation of the determined position on the display.

10 Claims, 49 Drawing Sheets

(56) References Cited

U.S. PATENT DOCUMENTS

| | | | | |
|---|---|---|---|---|
| 8,801,735 | B2 | 8/2014 | Shelton, IV et al. | |
| 8,827,903 | B2 | 9/2014 | Shelton, IV et al. | |
| 8,899,466 | B2 | 12/2014 | Baxter, III et al. | |
| 8,978,955 | B2 | 3/2015 | Aronhalt et al. | |
| 9,033,204 | B2 | 5/2015 | Shelton, IV et al. | |
| 9,113,883 | B2 | 8/2015 | Aronhalt et al. | |
| 9,125,654 | B2 | 9/2015 | Aronhalt et al. | |
| 9,204,877 | B2 * | 12/2015 | Whitman | A61B 17/068 |
| 9,345,544 | B2 * | 5/2016 | Hourtash | B25J 9/1643 |
| 10,426,476 | B2 | 10/2019 | Harris et al. | |
| 10,675,021 | B2 | 6/2020 | Harris et al. | |
| 10,682,136 | B2 | 6/2020 | Harris et al. | |
| 10,980,538 | B2 | 4/2021 | Nalagatla et al. | |
| 11,123,074 | B2 | 9/2021 | Adams et al. | |
| 11,147,559 | B2 | 10/2021 | Wise et al. | |
| 11,284,890 | B2 | 3/2022 | Nalagatla et al. | |
| 11,510,720 | B2 * | 11/2022 | Morgan | A61B 18/16 |
| 11,589,888 | B2 | 2/2023 | Shelton, IV et al. | |
| 11,690,624 | B2 * | 7/2023 | Eisinger | A61B 17/105<br>227/180.1 |
| 11,751,874 | B2 * | 9/2023 | Eschbach | A61B 17/07207<br>227/176.1 |
| 2004/0106916 | A1 * | 6/2004 | Quaid | A61B 34/71<br>606/1 |
| 2006/0097025 | A1 * | 5/2006 | Milliman | A61B 17/115<br>227/175.1 |
| 2006/0273135 | A1 * | 12/2006 | Beetel | A61B 17/128<br>227/175.1 |
| 2006/0278680 | A1 * | 12/2006 | Viola | A61B 17/068<br>227/176.1 |
| 2007/0151390 | A1 * | 7/2007 | Blumenkranz | G01L 5/22<br>74/490.06 |
| 2007/0175949 | A1 * | 8/2007 | Shelton, IV | A61B 17/285<br>227/176.1 |
| 2007/0270884 | A1 * | 11/2007 | Smith | A61B 17/1155<br>606/1 |
| 2008/0185419 | A1 * | 8/2008 | Smith | A61B 17/115<br>227/179.1 |
| 2008/0312687 | A1 * | 12/2008 | Blier | A61B 17/0686<br>227/176.1 |
| 2009/0012556 | A1 * | 1/2009 | Boudreaux | A61B 17/068<br>600/587 |
| 2009/0057369 | A1 * | 3/2009 | Smith | A61B 17/07207<br>227/175.1 |
| 2010/0096431 | A1 * | 4/2010 | Smith | A61B 17/115<br>227/175.2 |
| 2010/0096435 | A1 * | 4/2010 | Fuchs | A61B 17/1114<br>227/179.1 |
| 2010/0237132 | A1 * | 9/2010 | Measamer | A61B 17/115<br>227/180.1 |
| 2011/0017801 | A1 * | 1/2011 | Zemlok | A61B 17/07207<br>227/175.1 |
| 2011/0022032 | A1 * | 1/2011 | Zemlok | A61B 17/07207<br>606/1 |
| 2011/0144640 | A1 * | 6/2011 | Heinrich | A61B 17/062<br>606/41 |
| 2011/0307020 | A1 * | 12/2011 | Geist | A61B 34/70<br>606/86 R |
| 2012/0061447 | A1 * | 3/2012 | Williams | A61B 17/115<br>227/175.1 |
| 2012/0116391 | A1 * | 5/2012 | Houser | A61B 34/76<br>606/1 |
| 2012/0205419 | A1 * | 8/2012 | Weir | A61B 17/0686<br>227/175.1 |
| 2012/0223121 | A1 * | 9/2012 | Viola | A61B 17/07207<br>227/175.1 |
| 2012/0248167 | A1 * | 10/2012 | Flanagan | A61B 17/068<br>227/2 |
| 2013/0175318 | A1 * | 7/2013 | Felder | A61B 17/115<br>227/175.1 |
| 2014/0144968 | A1 * | 5/2014 | Shelton, IV | A61B 17/07292<br>227/175.1 |
| 2015/0053749 | A1 * | 2/2015 | Shelton, IV | G16H 40/63<br>227/181.1 |
| 2015/0054753 | A1 * | 2/2015 | Morgan | A61B 17/072<br>345/173 |
| 2015/0265358 | A1 * | 9/2015 | Bowling | A61B 34/20<br>700/261 |
| 2016/0256184 | A1 * | 9/2016 | Shelton, IV | A61B 17/295 |
| 2016/0256186 | A1 * | 9/2016 | Shelton, IV | A61B 17/295 |
| 2016/0374668 | A1 * | 12/2016 | Measamer | A61B 17/1155<br>227/175.1 |
| 2016/0374672 | A1 * | 12/2016 | Bear | H02J 7/00<br>606/219 |
| 2016/0374681 | A1 * | 12/2016 | Miller | A61B 17/105<br>227/176.1 |
| 2017/0095301 | A1 * | 4/2017 | Brisson | B25J 9/1607 |
| 2018/0360447 | A1 * | 12/2018 | Shelton, IV | A61B 17/0686 |
| 2019/0000478 | A1 * | 1/2019 | Messerly | A61B 18/00 |
| 2019/0125361 | A1 * | 5/2019 | Shelton, IV | A61B 17/1227 |
| 2019/0200981 | A1 * | 7/2019 | Harris | H04N 7/183 |
| 2019/0200998 | A1 * | 7/2019 | Shelton, IV | A61B 1/051 |
| 2019/0201020 | A1 * | 7/2019 | Shelton, IV | G16H 40/63 |
| 2019/0201034 | A1 * | 7/2019 | Shelton, IV | A61B 17/068 |
| 2019/0201104 | A1 * | 7/2019 | Shelton, IV | A61B 90/98 |
| 2019/0201145 | A1 * | 7/2019 | Shelton, IV | A61B 90/53 |
| 2019/0205001 | A1 * | 7/2019 | Messerly | A61B 17/295 |
| 2019/0206562 | A1 * | 7/2019 | Shelton, IV | H04N 23/555 |
| 2019/0206565 | A1 * | 7/2019 | Shelton, IV | A61B 90/90 |
| 2019/0388091 | A1 * | 12/2019 | Eschbach | A61B 17/07207 |
| 2020/0281595 | A1 * | 9/2020 | Wise | A61B 17/1114 |
| 2020/0281676 | A1 * | 9/2020 | Rohs | A61B 34/10 |
| 2020/0289119 | A1 * | 9/2020 | Viola | A61B 17/072 |
| 2020/0367891 | A1 * | 11/2020 | Kollar | A61B 17/1155 |
| 2020/0405304 | A1 * | 12/2020 | Mozdzierz | A61B 17/1155 |
| 2020/0405414 | A1 * | 12/2020 | Shelton, IV | A61B 17/320092 |
| 2021/0077111 | A1 * | 3/2021 | Adams | A61B 90/06 |
| 2021/0077112 | A1 * | 3/2021 | Adams | A61B 17/1114 |
| 2021/0282773 | A1 * | 9/2021 | Kuruvatti | A61B 17/072 |
| 2021/0298846 | A1 * | 9/2021 | Dozeman | A61B 90/03 |
| 2022/0082367 | A1 * | 3/2022 | Jeon | G01B 3/18 |
| 2022/0104806 | A1 * | 4/2022 | Shelton, IV | A61B 17/1155 |
| 2022/0104820 | A1 * | 4/2022 | Shelton, IV | A61B 17/07207 |
| 2022/0331047 | A1 | 10/2022 | Shelton, IV et al. | |
| 2022/0395348 | A1 * | 12/2022 | Nicholas | A61B 17/1155 |
| 2023/0038322 | A1 * | 2/2023 | Hart | A61B 17/3476 |
| 2023/0123673 | A1 * | 4/2023 | Gonenc | A61B 17/07207<br>227/176.1 |
| 2023/0255701 | A1 * | 8/2023 | Post | A61B 34/30<br>606/82 |
| 2023/0404572 | A1 * | 12/2023 | Rivard | G16H 30/40 |
| 2024/0023967 | A1 * | 1/2024 | Valentine, Jr. | A61B 90/06 |
| 2024/0081934 | A1 * | 3/2024 | Khurana | A61B 34/74 |
| 2025/0060758 | A1 * | 2/2025 | Magner | B25J 9/1664 |
| 2025/0221782 | A1 * | 7/2025 | Dozeman | A61B 17/14 |

FOREIGN PATENT DOCUMENTS

| | | | | |
|---|---|---|---|---|
| EP | 3231371 | A1 * | 10/2017 | A61B 17/068 |
| EP | 3705061 | A2 * | 9/2020 | A61B 17/115 |
| WO | WO-2010057867 | A2 * | 5/2010 | G01N 27/4073 |
| WO | WO-2022070051 | A1 * | 4/2022 | A61B 17/1155 |
| WO | WO-2022070064 | A1 * | 4/2022 | A61B 17/1155 |
| WO | WO-2022125397 | A1 * | 6/2022 | A61B 17/1155 |
| WO | WO-2023242762 | A1 * | 12/2023 | A61B 17/1155 |

* cited by examiner

Embodiment A: Indicator Position Feedback

Embodiment B: Graphical Position Feedback

1400

Embodiment C: Numerical Gap and Force Feedback

Embodiment C: Numerical Gap and Force Feedback

Embodiment D: Graphical Gap and Force

SMART CIRCULAR STAPLERS

CROSS-REFERENCE TO RELATED APPLICATIONS

This application claims the benefit of priority under 35 U.S.C. 119(e) to U.S. Provisional Patent Application Ser. No. 63/353,279, titled SMART CIRCULAR STAPLERS, filed Jun. 17, 2022, the disclosure of which is herein incorporated by reference in its entirety.

BACKGROUND

This disclosure relates to apparatuses, systems, and methods for providing feedback to a user of a circular stapler during a surgical procedure.

SUMMARY

In various embodiments, a surgical stapler is disclosed comprising an end effector configured to receive a staple cartridge, a trocar movable relative to the end effector, an anvil removably coupleable to the trocar, a sensor, a housing comprising a display, and a control circuit operably coupled to the sensor and the display. The anvil is movable relative to the end effector based on movement of the trocar. The anvil is configured to apply a force to tissue positioned between the anvil and the end effector. The sensor is configured to sense the force. The control circuit is configured to interrogate the sensor to determine the force and display a representation of the determined force on the display.

In various embodiments, a surgical stapler is disclosed comprising an end effector configured to receive a staple cartridge, a trocar movable relative to the end effector, an anvil removably coupleable to the trocar, a sensor, a housing comprising a display, and a control circuit operably coupled to the sensor and the display. The anvil is movable relative to the end effector based on movement of the trocar. The sensor is configured to sense a position of the anvil relative to the end effector. The control circuit is configured to interrogate the sensor to determine the position of the anvil and display a representation the determined position on the display.

In various embodiments, a surgical stapler is disclosed comprising an end effector configured to receive a staple cartridge, a trocar movable relative to the end effector, an anvil removably coupleable to the trocar, a sensor, a housing comprising a display, and a control circuit operably coupled to the sensor and the display. The anvil is movable relative to the end effector based on movement of the trocar. The anvil is configured to apply a force to tissue positioned between the anvil and the end effector. The sensor is configured to sense attachment of the anvil with the trocar. The control circuit is configured to interrogate the sensor to determine that the anvil is coupled to trocar and display a representation on the display that the anvil is coupled to the trocar.

FIGURES

The various aspects described herein, both as to organization and methods of operation, together with further objects and advantages thereof, may best be understood by reference to the following description, taken in conjunction with the accompanying drawings as follows.

Corresponding reference characters indicate corresponding parts throughout the several views. The exemplifications set out herein illustrate various disclosed embodiments, in one form, and such exemplifications are not to be construed as limiting the scope thereof in any manner.

DESCRIPTION

Figure 1:
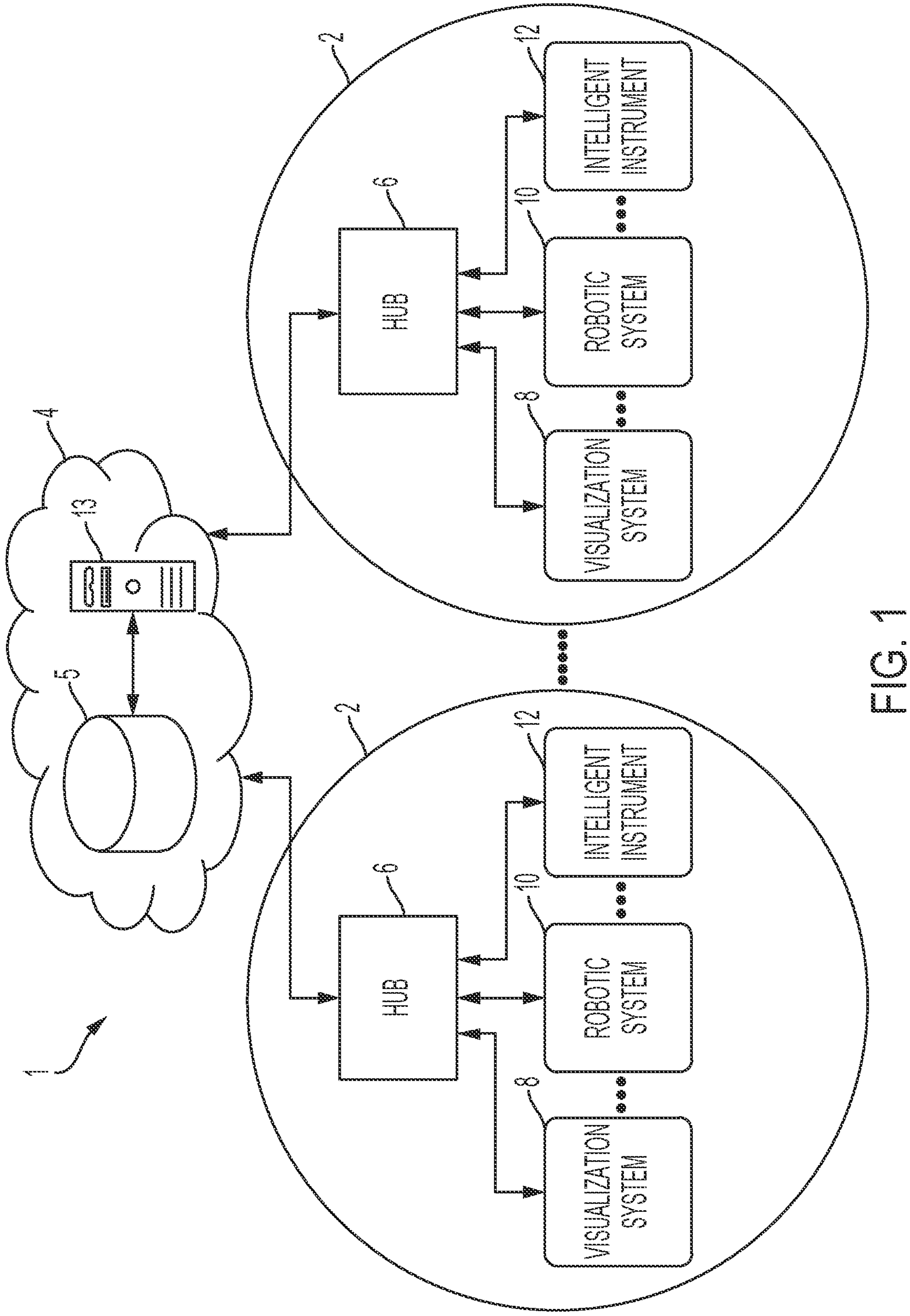
FIG. 1 is a block diagram of a computer-implemented interactive surgical system, according to one aspect of this disclosure.

Applicant of the present application owns the following U.S. patent application, the disclosures of which is herein incorporated by reference in its entirety:

- U.S. patent application Ser. No. 17/688,589, titled METHOD FOR INTRAOPERATIVE DISPLAY FOR SURGICAL SYSTEMS, filed Mar. 7, 2022.

Applicant of this application owns the following U.S. patent applications, the disclosure of each of which is herein incorporated by reference in its entirety:

- U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Publication No. US-2019-0200981-A1;
- U.S. patent application Ser. No. 16/209,453, titled METHOD FOR CONTROLLING SMART ENERGY DEVICES, now U.S. Patent Publication No. US-2019-0201046-A1; and
- U.S. Provisional Patent Application No. 63/348,218, titled "CUSTOMIZATION, TROUBLESHOOTING, AND WIRELESS PAIRING TECHNIQUES FOR SURGICAL INSTRUMENTS, filed Jun. 2, 2022.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to onscreen displays for surgical systems for a variety of energy and surgical stapler based medical devices. Energy based medical devices include, without limitation, radio-frequency (RF) based monopolar and bipolar electrosurgical instruments, ultrasonic surgical instruments, combination RF electrosurgical and ultrasonic instruments, combination RF electrosurgical and mechanical staplers, among others. Surgical stapler devices include and combined surgical staplers with electrosurgical and/or ultrasonic devices. Aspects of the ultrasonic surgical devices can be configured for transecting and/or coagulating tissue during surgical procedures, for example. Aspects of the electrosurgical devices can be configured for transecting, coagulating, sealing, welding and/or desiccating tissue during surgical procedures, for example. Aspects of the surgical stapler devices can be configured for transecting and stapling tissue during surgical procedures and in some aspects, the surgical stapler devices may be configured to delivery RF energy to the tissue during surgical procedures. Electrosurgical devices are configured to deliver therapeutic and/or nontherapeutic RF energy to the tissue. Elements of surgical staplers, electrosurgical, and ultrasonic devices may be used in combination in a single surgical instrument.

In various aspects, the present disclosure provides onscreen displays of real time information to the OR team during a surgical procedure. In accordance with various aspects of the present disclosure, many new and unique onscreen displays are provided to display onscreen a variety of visual information feedback to the OR team. According to the present disclosure, visual information may comprise one or more than one of various visual media with or without sound. Generally, visual information comprises still photography, motion picture photography, video or audio recording, graphic arts, visual aids, models, display, visual presentation services, and the support processes. The visual information can be communicated on any number of display options such as the primary OR screen, the energy or surgical stapler device itself, a tablet, augmented reality glasses, among others, for example.

In various aspects, the present disclosure provides a large list of potential options to communicate visual information in real time to the OR team, without overwhelming the OR team with too much visual information. For example, in various aspects, the present disclosure provides onscreen displays of visual information to enable the surgeon, or other members of the OR team, to selectively activate onscreen displays such as icons surrounding the screen option to manage a wealth of visual information. One or a combination of factors can be used to determine the active display, these may include energy based (e.g., electrosurgical, ultrasonic) or mechanical based (e.g., staplers) surgical devices in use, the estimated risk associated with a given display, the experience level of the surgeon and the surgeons' choice among other things. In other aspect, the visual information may comprises rich data overlaid or superimposed into the surgical field of view to manage the visual information. In various aspects described hereinbelow, comprise superimposed imagery that requires video analysis and tracking to properly overlay the data. Visual information data communicated in this manner, as opposed to static icons, may provide additional useful visual information in a more concise and easy to understand way to the OR team.

In various aspects, the present disclosure provides techniques for selectively activating onscreen displays such as icons surrounding the screen to manage visual information during a surgical procedure. In other aspects, the present disclosure provides techniques for determining the active display using one or a combination of factors. In various aspects, the techniques according to the resent disclosure may comprise selecting the energy based or mechanical based surgical device in use as the active display, estimating risk associated with a given display, utilizing the experience level of the surgeon or OR team making the selection, among other things.

In other aspects, the techniques according to the present disclosure may comprise overlaying or superimposing rich data onto the surgical field of view to manage the visual information. A number of the display arrangements described by the present disclosure involve overlaying various visual representations of surgical data onto a livestream of a surgical field. As used herein the term overlay comprises a translucent overlay, a partial overlay, and/or a moving overlay. Graphical overlays may be in the form of a transparent graphic, semitransparent graphic, or opaque graphic, or a combination of transparent, semitransparent, and opaque elements or effects. Moreover, the overlay can be positioned on, or at least partially on, or near an object in the surgical field such as, for example, an end effector and/or a critical surgical structure. Certain display arrangements may comprise a change in one or more display elements of an overlay including a change in color, size, shape, display time, display location, display frequency, highlighting, or a combination thereof, based on changes in display priority values. The graphical overlays are rendered on top of the active display monitor to convey important information quickly and efficiently to the OR team.

In other aspects, the techniques according to the present disclosure may comprise superimposing imagery that requires analyzing video and tracking for properly overlaying the visual information data. In other aspects, the techniques according to the present disclosure may comprise communicating rich visual information, as opposed to simple static icons, to provide additional visual information to the OR team in a more concise and easy to understand manner. In other aspects, the visual overlays may be used in combination with audible and/or somatosensory overlays such as thermal, chemical, and mechanical devices, and combinations thereof.

The following description is directed generally to apparatuses, systems, and methods that provide an augmented reality (AR) interactive experience during a surgical procedure. In this context, images of a surgical field and surgical instruments and other objects appearing in the surgical field are enhanced by overlaying computer-generated visual, auditory, haptic, somatosensory, olfactory, or other sensory information onto the real world images of the surgical field, instruments, and/or other objects appearing in the surgical field. The images may be streamed in real time or may be still images. Augmented reality is a technology for rendering and displaying virtual or "augmented" virtual objects, data, or visual effects overlaid on a real environment. The real environment may include a surgical field. The virtual objects overlaid on the real environment may be represented as anchored or in a set position relative to one or more aspects of the real environment. In a non-limiting example, if a real world object exits the real environment field of view, a virtual object anchored to the real world object would also exit the augmented reality field of view.

A number of the display arrangements described by the present disclosure involve overlaying various visual representations of surgical data onto a livestream of a surgical field. As used herein the term overlaying comprises a translucent overlay, a partial overlay, and/or a moving overlay. Moreover, the overlay can be positioned on, or at least partially on, or near an object in the surgical field such as, for example, an end effector and/or a critical surgical structure. Certain display arrangements may comprise a change in one or more display elements of an overlay including a change in color, size, shape, display time, display location, display frequency, highlighting, or a combination thereof, based on changes in display priority values.

As described herein AR is an enhanced version of the real physical world that is achieved through the use of digital visual elements, sound, or other sensory stimuli delivered via technology. Virtual Reality (VR) is a computer-generated environment with scenes and objects that appear to be real, making the user feel they are immersed in their surroundings. This environment is perceived through a device known as a Virtual Reality headset or helmet. Mixed reality (MR) and AR are both considered immersive technologies, but they aren't the same. MR is an extension of Mixed reality that allows real and virtual elements to interact in an environment. While AR adds digital elements to a live view often by using a camera, an MR experience combines elements of both AR and VR, where real-world and digital objects interact.

In an AR environment, one or more computer-generated virtual objects may be displayed along with one or more real (i.e., so-called "real world") elements. For example, a real-time image or video of a surrounding environment may be shown on a computer screen display with one or more overlaying virtual objects. Such virtual objects may provide complementary information relating to the environment or generally enhance a user's perception and engagement with the environment. Conversely, the real-time image or video of the surrounding environment may additionally or alternatively enhance a user's engagement with the virtual objects shown on the display.

The apparatuses, systems, and methods in the context of this disclosure enhance images received from one or more imaging devices during a surgical procedure. The imaging devices may include a variety of scopes used during non-invasive and minimally invasive surgical procedures, an AR device, and/or a camera to provide images during open surgical procedures. The images may be streamed in real time or may be still images. The apparatuses, systems, and methods provide an augmented reality interactive experience by enhancing images of the real world surgical environment by overlaying virtual objects or representations of data and/or real objects onto the real surgical environment. The augmented reality experience may be viewed on a display and/or an AR device that allows a user to view the overlaid virtual objects onto the real world surgical environment. The display may be located in the operating room or remote from the operating room. AR devices are worn on the head of the surgeon or other operating room personnel and typically include two stereo-display lenses or screens, including one for each eye of the user. Natural light is permitted to pass through the two transparent or semi-transparent display lenses such that aspects of the real environment are visible while also projecting light to make virtual objects visible to the user of the AR device.

Two or more displays and AR devices may be used in a coordinated manner, for example with a first display or AR device controlling one or more additional displays or AR devices in a system with defined roles. For example, when activating display or an AR device, a user may select a role (e.g., surgeon, surgical assistant, nurse, etc., during a surgical procedure) and the display or AR device may display information relevant to that role. For example, a surgical assistant may have a virtual representation of an instrument displayed that the surgeon needs to perform for a next step of a surgical procedure. A surgeon's focus on the current step may see different information displayed than the surgical assistant.

Although there are many known onscreen displays and alerts, this disclosure provides many new and unique augmented reality interactive experiences during a surgical procedure. Such augmented reality interactive experiences include visual, auditory, haptic, somatosensory, olfactory, or other sensory feedback information to the surgical team inside or outside the operating room. The virtual feedback information overlaid onto the real world surgical environment may be provided to an operating room (OR) team, including personnel inside the OR including, without limitation, the operating surgeon, assistants to the surgeon, a scrub person, an anesthesiologist and a circulating nurse, among others, for example. The virtual feedback information can be communicated on any number of display options such as a primary OR screen display, an AR device, the energy or surgical stapler instrument, a tablet, augmented reality glasses, device etc.

FIG. 1 depicts a computer-implemented interactive surgical system 1 that includes one or more surgical systems 2 and a cloud-based system 4. The cloud-based system 4 may include a remote server 13 coupled to a storage device 5. Each surgical system 2 includes at least one surgical hub 6 in communication with the cloud 4. For example, the surgical system 2 may include a visualization system 8, a robotic system 10, and handheld intelligent surgical instruments 12, each configured to communicate with one another and/or the hub 6. In some aspects, a surgical system 2 may include an M number of hubs 6, an N number of visualization systems 8, an O number of robotic systems 10, and a P number of handheld intelligent surgical instruments 12, where M, N, O, and P are integers greater than or equal to one. The computer-implemented interactive surgical system 1 may be configured to provide an augmented reality interactive experience during a surgical procedure as described herein.

Figure 2:
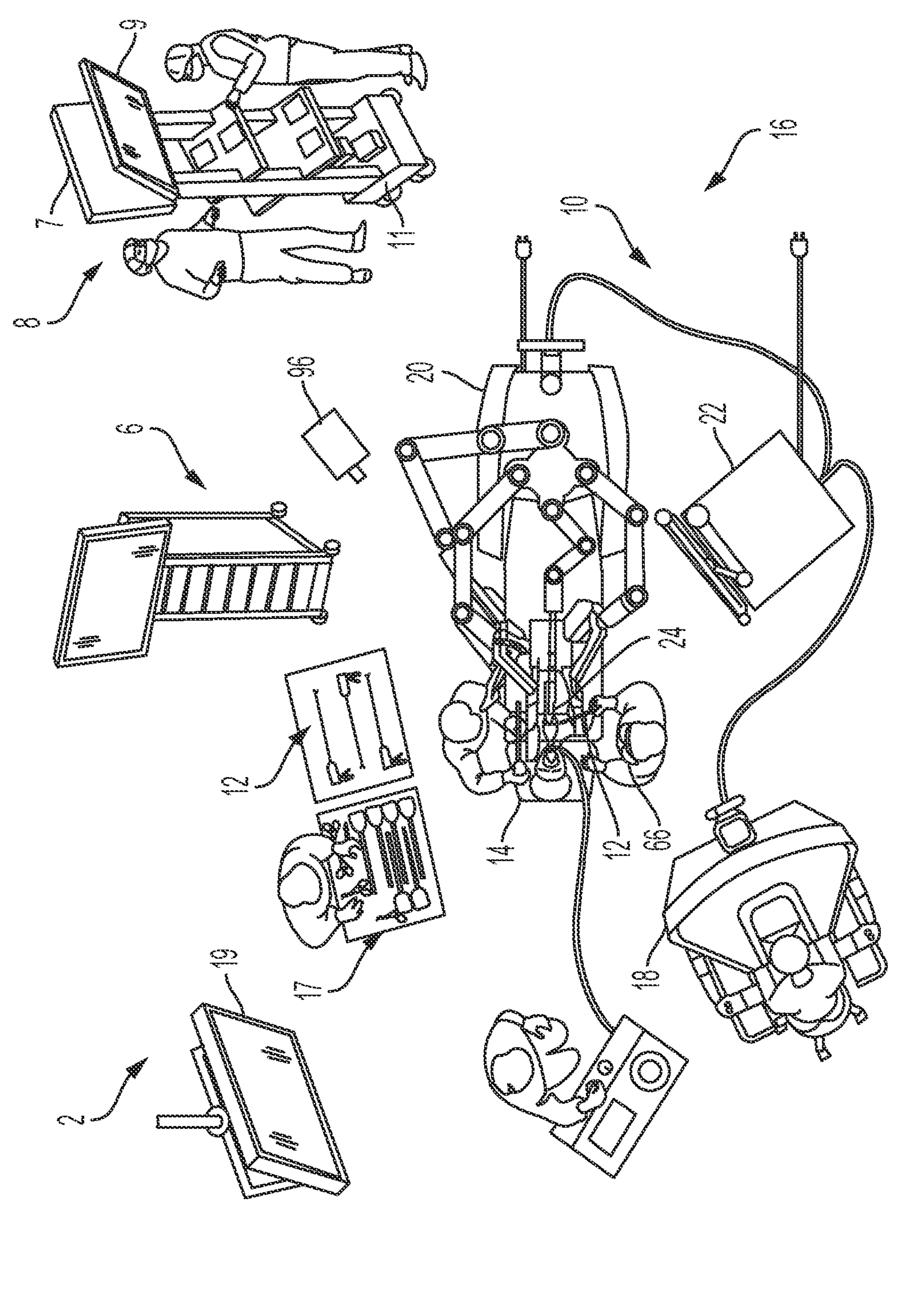
FIG. 2 is a surgical system being used to perform a surgical procedure in an operating room, according to one aspect of this disclosure.

FIG. 2 depicts an example of a surgical system 2 to perform a surgical procedure on a patient lying down on an operating table 14 in a surgical operating room 16. A robotic system 10 is used in the surgical procedure as a part of the surgical system 2. The robotic system 10 includes a surgeon's console 18, a patient side cart 20 (surgical robot), and a surgical robotic hub 22. The patient side cart 20 can manipulate at least one removably coupled surgical tool 17 through a minimally invasive incision in the body of the patient while the surgeon views the surgical site through the surgeon's console 18 or an augmented reality (AR) device 66 worn by the surgeon. An image (e.g., still or live streamed in real time) of the surgical site during a minimally invasive procedure can be obtained by a medical imaging device 24. The patient side cart 20 can manipulate the imaging device 24 to orient the imaging device 24. An image of an open surgical procedure can be obtained by a medical imaging device 96. The robotic hub 22 processes the images of the surgical site for subsequent display on the surgeon's console 18 or the AR device 66 worn by the surgeon, or other person in the surgical operating room 16.

The optical components of the imaging device 24, 96 or AR device 66 may include one or more illumination sources and/or one or more lenses. The one or more illumination sources may be directed to illuminate portions of the surgical field. One or more image sensors may receive light reflected or refracted from tissue and instruments in the surgical field.

In various aspects, the imaging device 24 is configured for use in a minimally invasive surgical procedure. Examples of imaging devices suitable for use with this disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope. In various aspects, the imaging device 96 is configured for use in an open (invasive) surgical procedure.

In various aspects, the visualization system 8 includes one or more imaging sensors, one or more image-processing units, one or more storage arrays, and one or more displays that are strategically arranged with respect to the sterile field. In one aspect, the visualization system 8 includes an interface for HL7, PACS, and EMR. In one aspect, the imaging device 24 may employ multi-spectrum monitoring to discriminate topography and underlying structures. A multi-spectral image captures image data within specific wavelength ranges in the electromagnetic spectrum. Wavelengths are separated by filters or instruments sensitive to particular wavelengths, including light from frequencies beyond the visible light range, e.g., IR and ultraviolet. Spectral imaging can extract information not visible to the human eye. Multi-spectrum monitoring can relocate a surgical field after a surgical task is completed to perform tests on the treated tissue.

FIG. 2 depicts a primary display 19 positioned in the sterile field to be visible to an operator at the operating table 14. A visualization tower 11 is positioned outside the sterile field and includes a first non-sterile display 7 and a second non-sterile display 9, which face away from each other. The visualization system 8, guided by the hub 6, is configured to utilize the displays 7, 9, 19 to coordinate information flow to operators inside and outside the sterile field. For example, the hub 6 may cause the visualization system 8 to display AR images of the surgical site, as recorded by an imaging device 24, 96 on a non-sterile display 7, 9, or through the AR device 66, while maintaining a live feed of the surgical site on the primary display 19 or the AR device 66. The non-sterile display 7, 9 can permit a non-sterile operator to perform a diagnostic step relevant to the surgical procedure, for example.

Figure 3:
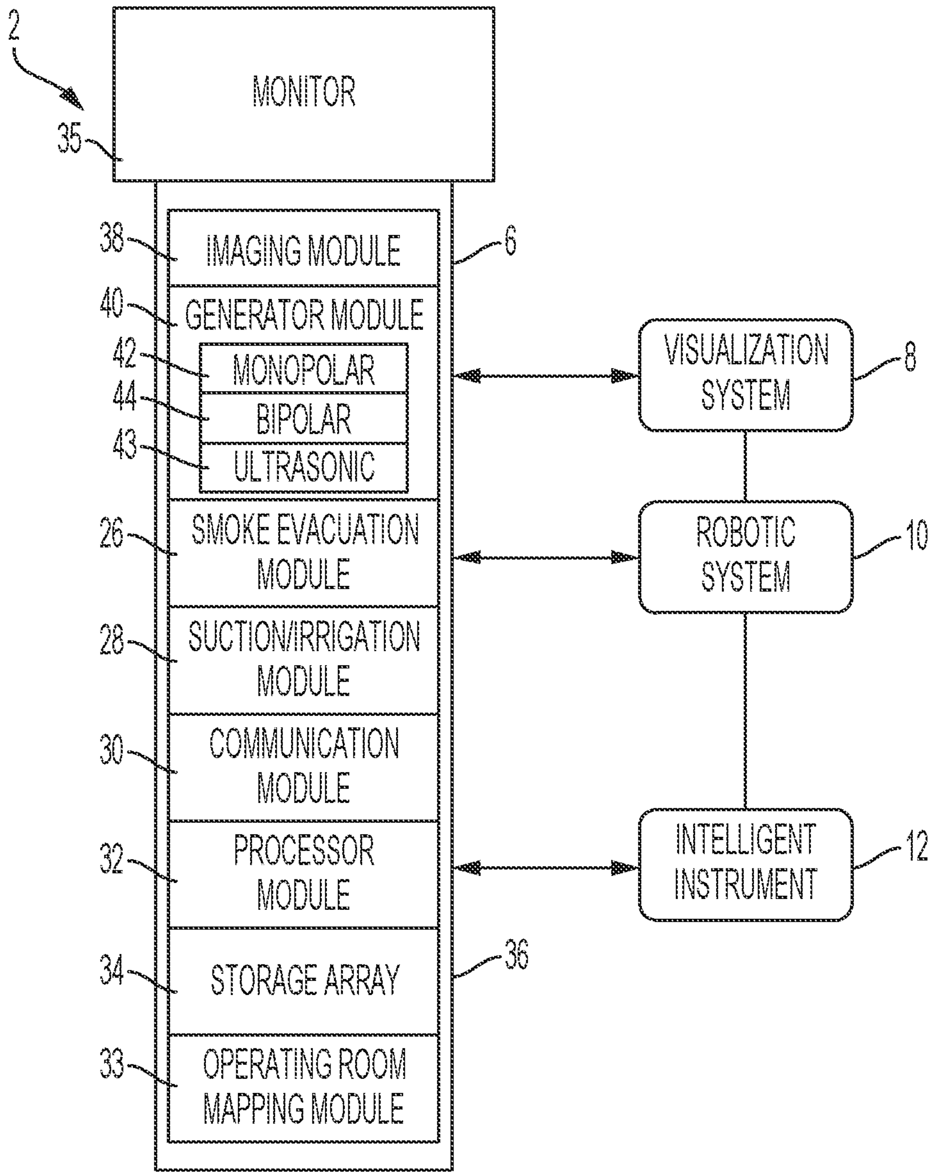
FIG. 3 is a surgical hub paired with a visualization system, a robotic system, and an intelligent instrument, according to one aspect of this disclosure.
Figure 10:
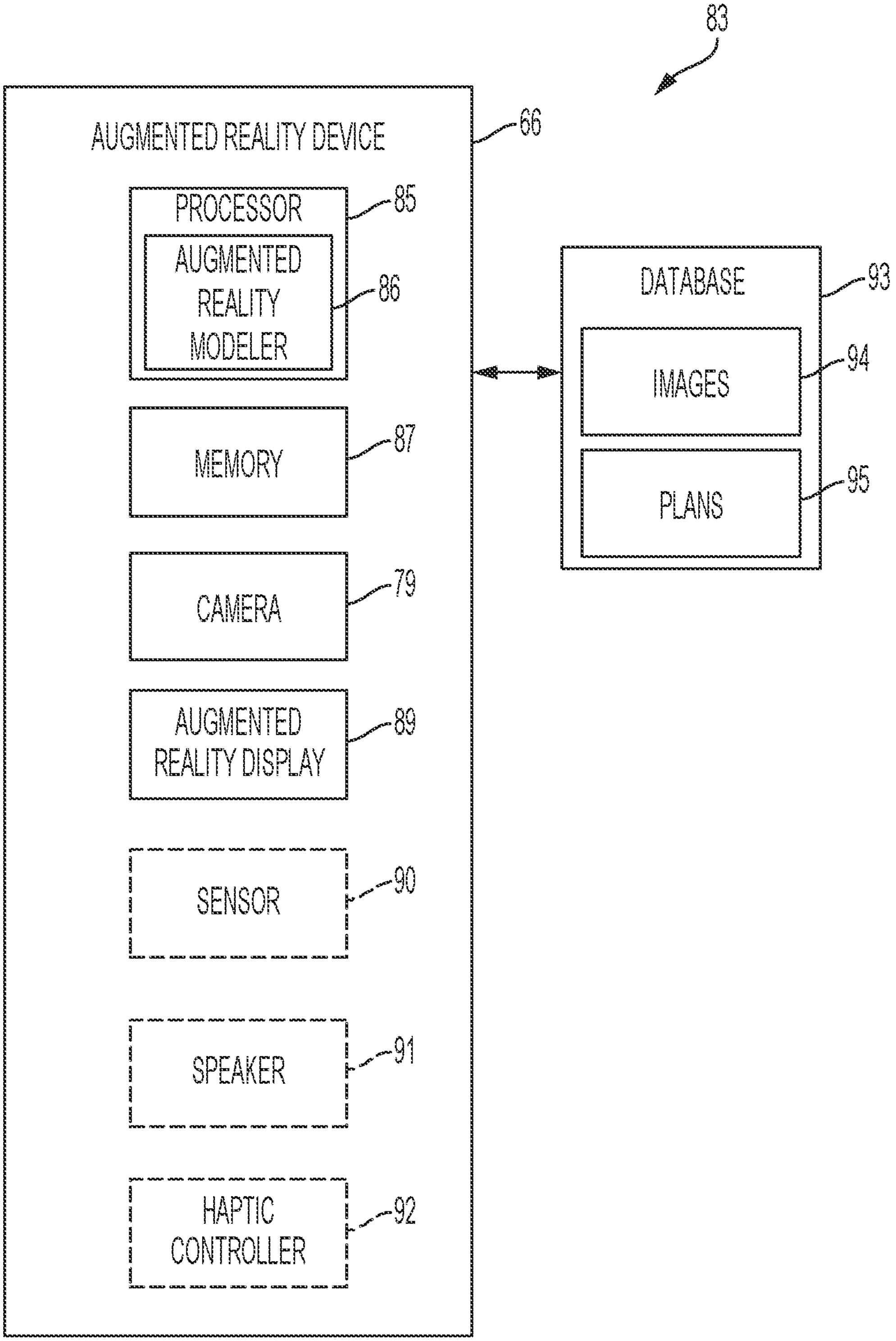
FIG. 10 illustrates a system for augmenting surgical instrument information using an augmented reality display, according to one aspect of this disclosure.

FIG. 3 depicts a hub 6 in communication with a visualization system 8, a robotic system 10, and a handheld intelligent surgical instrument 12. The hub 6 includes a hub display an imaging module 38, a generator module 40, a communication module 30, a processor module 32, a storage array 34, and an operating room mapping module 33. The hub 6 further includes a smoke evacuation module 26 and/or a suction/irrigation module 28. In various aspects, the imaging module 38 comprises an AR device 66 and the processor module 32 comprises an integrated video processor and an augmented reality modeler (e.g., as shown in FIG. 10). A modular light source may be adapted for use with various imaging devices. In various examples, multiple imaging devices may be placed at different positions in the surgical field to provide multiple views (e.g., non-invasive, minimally invasive, invasive or open surgical procedures). The imaging module 38 can be configured to switch between the imaging devices to provide an optimal view. In various aspects, the imaging module 38 can be configured to integrate the images from the different imaging devices and provide an augmented reality interactive experience during a surgical procedure as described herein.

Figure 4:
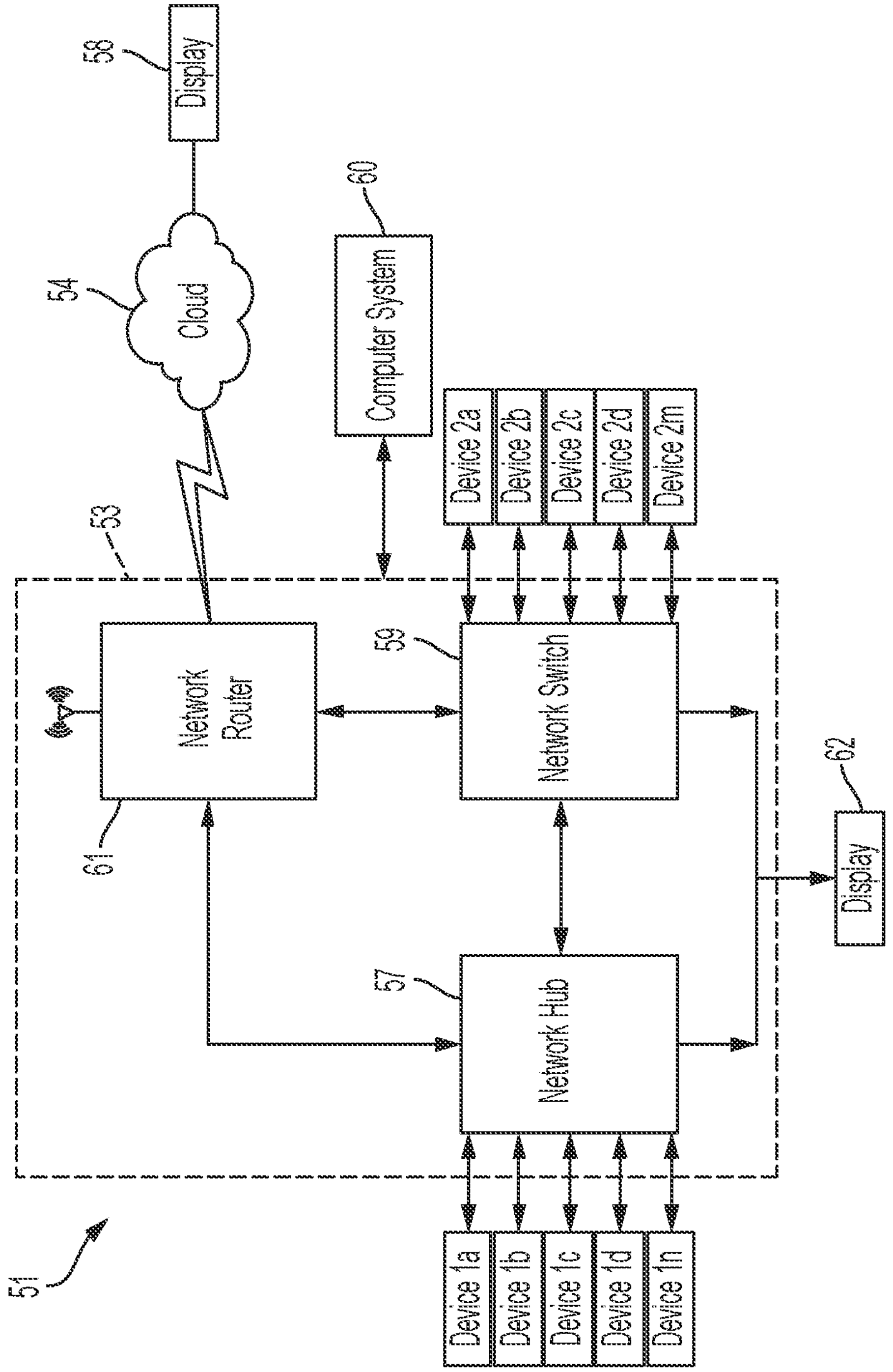
FIG. 4 illustrates a surgical data network comprising a modular communication hub configured to connect modular devices located in one or more operating theaters of a healthcare facility, or any room in a healthcare facility specially equipped for surgical operations, to the cloud, according to one aspect of this disclosure.

FIG. 4 shows a surgical data network 51 comprising a modular communication hub 53 configured to connect modular devices located in one or more operating theaters/rooms of a healthcare facility to a cloud-based system. The cloud 54 may include a remote server 63 (FIG. coupled to a storage device 55. The modular communication hub 53 comprises a network hub 57 and/or a network switch 59 in communication with a network router 61. The modular communication hub 53 is coupled to a local computer system 60 to process data. Modular devices 1*a*-1*n* in the operating theater may be coupled to the modular communication hub 53. The network hub 57 and/or the network switch 59 may be coupled to a network router 61 to connect the devices 1*a*-1*n* to the cloud 54 or the local computer system 60. Data associated with the devices 1*a*-1*n* may be transferred to cloud-based computers via the router for remote data processing and manipulation. The operating theater devices 1*a*-1*n* may be connected to the modular communication hub 53 over a wired channel or a wireless channel. The surgical data network 51 environment may be employed to provide an augmented reality interactive experience during a surgical procedure as described herein and in particular providing augmented images if the surgical field to one or more than one remote display 58.

Figure 5:
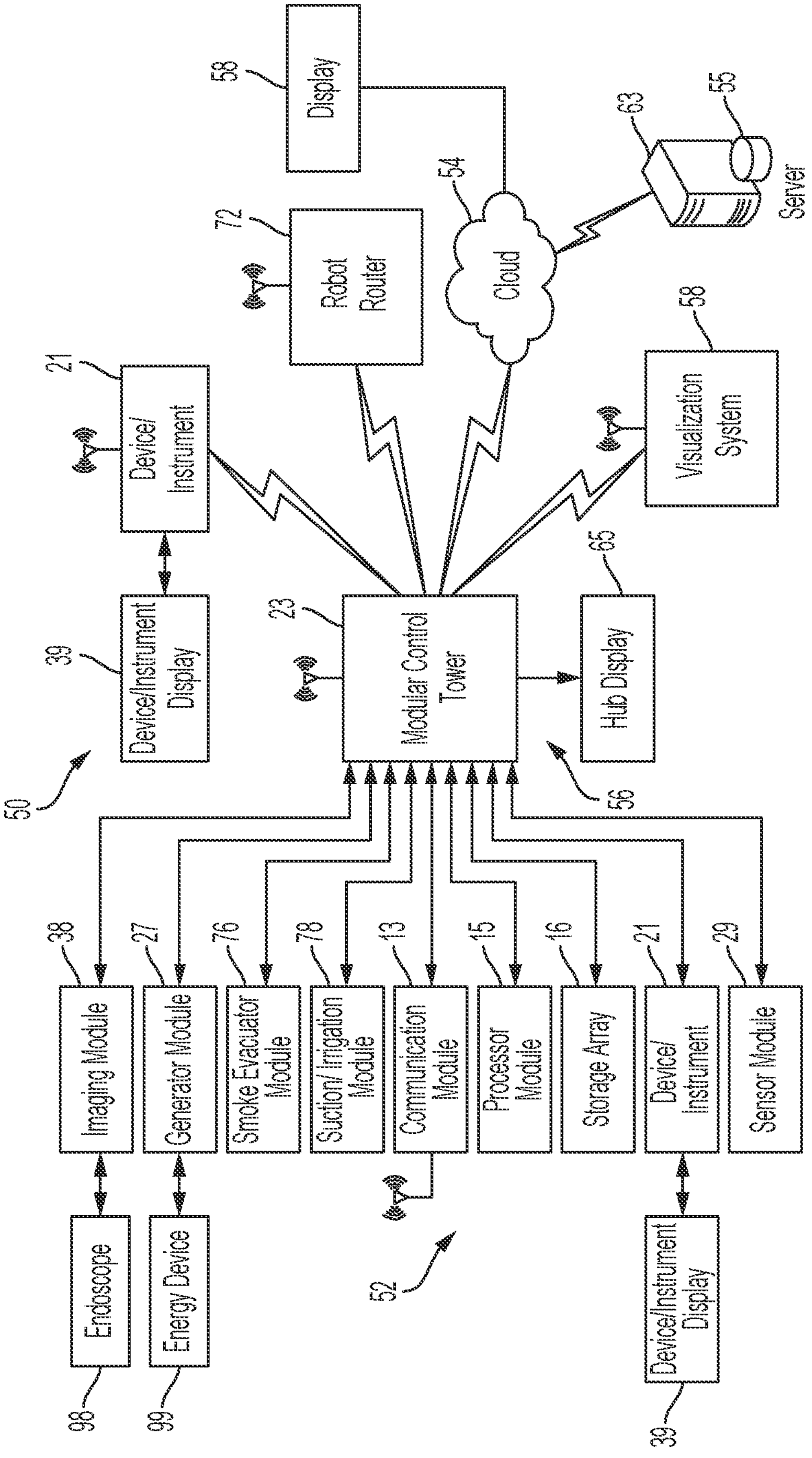
FIG. 5 illustrates a computer-implemented interactive surgical system, according to one aspect of this disclosure.
Figure 6:
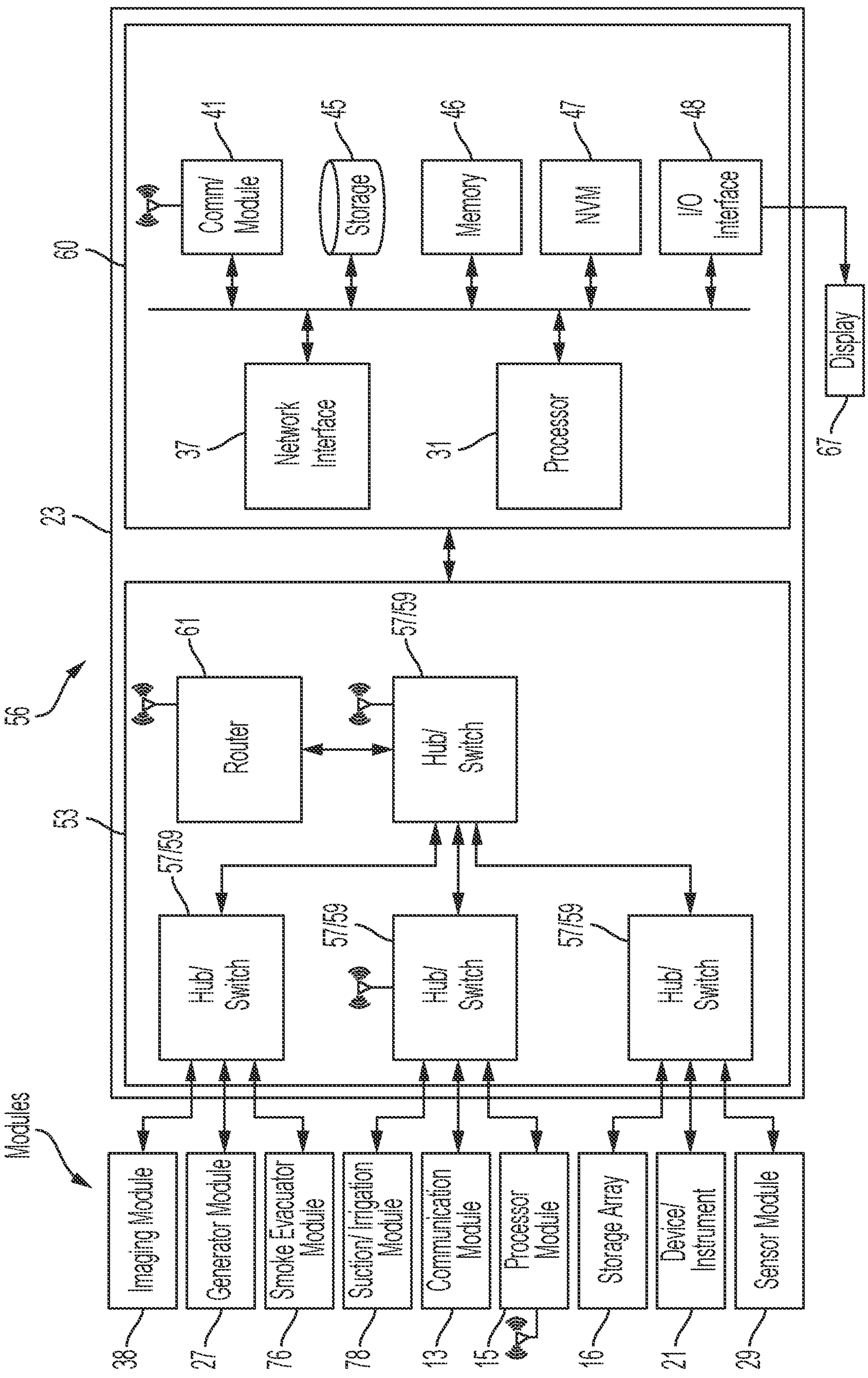
FIG. 6 illustrates a surgical hub comprising a plurality of modules coupled to the modular control tower, according to one aspect of this disclosure.

FIG. 5 illustrates a computer-implemented interactive surgical system 50. The computer-implemented interactive surgical system 50 is similar in many respects to the computer-implemented interactive surgical system 1. The computer-implemented interactive surgical system 50 includes one or more surgical systems 52, which are similar in many respects to the surgical systems 2. Each surgical system 52 includes at least one surgical hub 56 in communication with a cloud 54 that may include a remote server 63. In one aspect, the computer-implemented interactive surgical system 50 comprises a modular control tower 23 connected to multiple operating theater devices such as, for example, intelligent surgical instruments, robots, and other computerized devices located in the operating theater. As shown in FIG. 6, the modular control tower 23 comprises a modular communication hub 53 coupled to a computer system 60.

Back to FIG. 5, the modular control tower 23 is coupled to an imaging module 38 that is coupled to an endoscope 98, a generator module 27 that is coupled to an energy device 99, a smoke evacuator module 76, a suction/irrigation module 78, a communication module 13, a processor module 15, a storage array 16, a smart device/instrument 21 optionally coupled to a display 39, and a sensor module 29. The operating theater devices are coupled to cloud computing resources such as server 63, data storage 55, and displays 58 via the modular control tower 23. A robot hub 72 also may be connected to the modular control tower 23 and to the servers 63, data storage 55, and displays 58. The devices/instruments 21, visualization systems 58, among others, may be coupled to the modular control tower 23 via wired or wireless communication standards or protocols, as described herein. The modular control tower 23 may be coupled to a hub display 65 (e.g., monitor, screen) to display augmented images received comprising overlaid virtual objects on the real surgical field received from the imaging module 38, device/instrument display 39, and/or other visualization systems 58. The hub display also may display data received from devices connected to the modular control tower 23 in conjunction with images and overlaid images.

FIG. 6 illustrates a surgical hub 56 comprising a plurality of modules coupled to the modular control tower 23. The modular control tower 23 comprises a modular communication hub 53, e.g., a network connectivity device, and a computer system 60 to provide local processing, visualization, and imaging of augmented surgical information, for example. The modular communication hub 53 may be connected in a tiered configuration to expand the number of modules (e.g., devices) that may be connected to the modular communication hub 53 and transfer data associated with the modules to the computer system 60, cloud computing resources, or both. Each of the network hubs/switches 57, 59 in the modular communication hub 53 may include three downstream ports and one upstream port. The upstream network hub/switch 57, 59 is connected to a processor 31 to provide a communication connection to the cloud computing resources and a local display 67. Communication to the cloud 54 may be made either through a wired or a wireless communication channel.

The computer system 60 comprises a processor 31 and a network interface 37. The processor 31 is coupled to a communication module 41, storage 45, memory 46, non-volatile memory 47, and input/output interface 48 via a system bus. The system bus can be any of several types of bus structure(s) including the memory bus or memory controller, a peripheral bus or external bus, and/or a local bus using any variety of available bus architectures.

The processor 31 comprises an augmented reality modeler (e.g., as shown in FIG. 10) and may be implemented as a single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 60 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

In various aspects, the computer system 60 of FIG. 6, the imaging module 38 and/or visualization system 58, and/or the processor module 15 of FIGS. 4-6, may comprise an image processor, image-processing engine, graphics processing unit (GPU), media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

Figure 7:
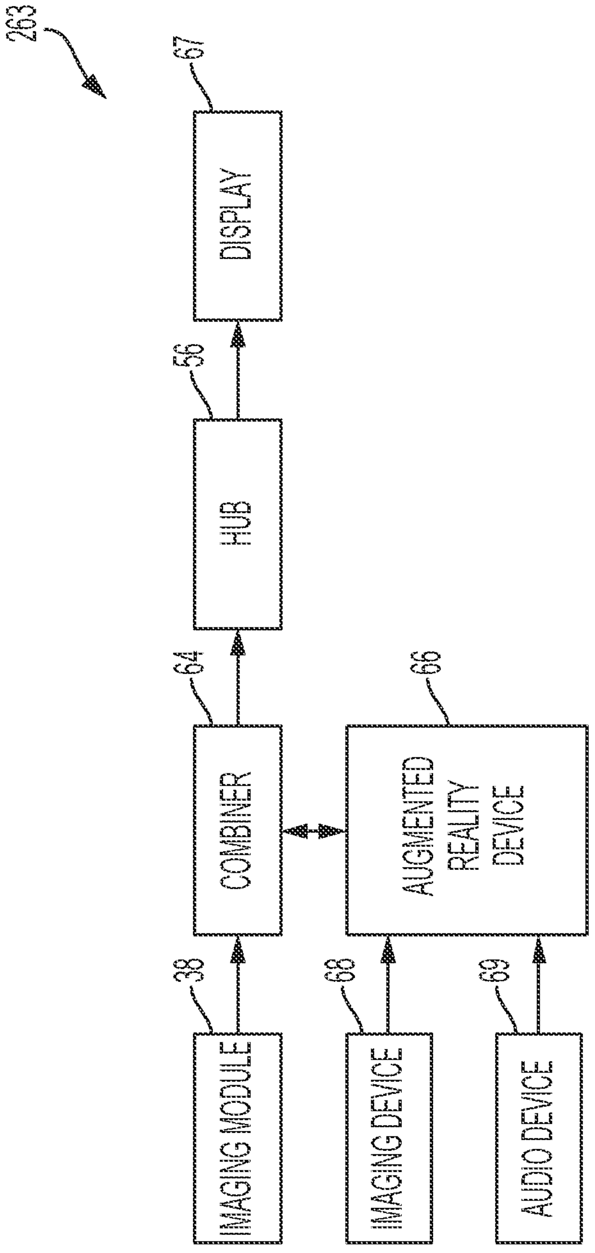
FIG. 7 illustrates an augmented reality (AR) system comprising an intermediate signal combiner positioned in the communication path between an imaging module and a surgical hub display, according to one aspect of this disclosure.

FIG. 7 illustrates an augmented reality system 263 comprising an intermediate signal combiner 64 positioned in the communication path between an imaging module 38 and a surgical hub display 67. The signal combiner 64 combines audio and/or image data received from an imaging module 38 and/or an AR device 66. The surgical hub 56 receives the combined data from the combiner 64 and overlays the data provided to the display 67, where the overlaid data is displayed. The imaging device 68 may be a digital video camera and the audio device 69 may be a microphone. The signal combiner 64 may comprise a wireless heads-up display adapter to couple to the AR device 66 placed into the communication path of the display 67 to a console allowing the surgical hub 56 to overlay data on the display 67.

Figure 8:
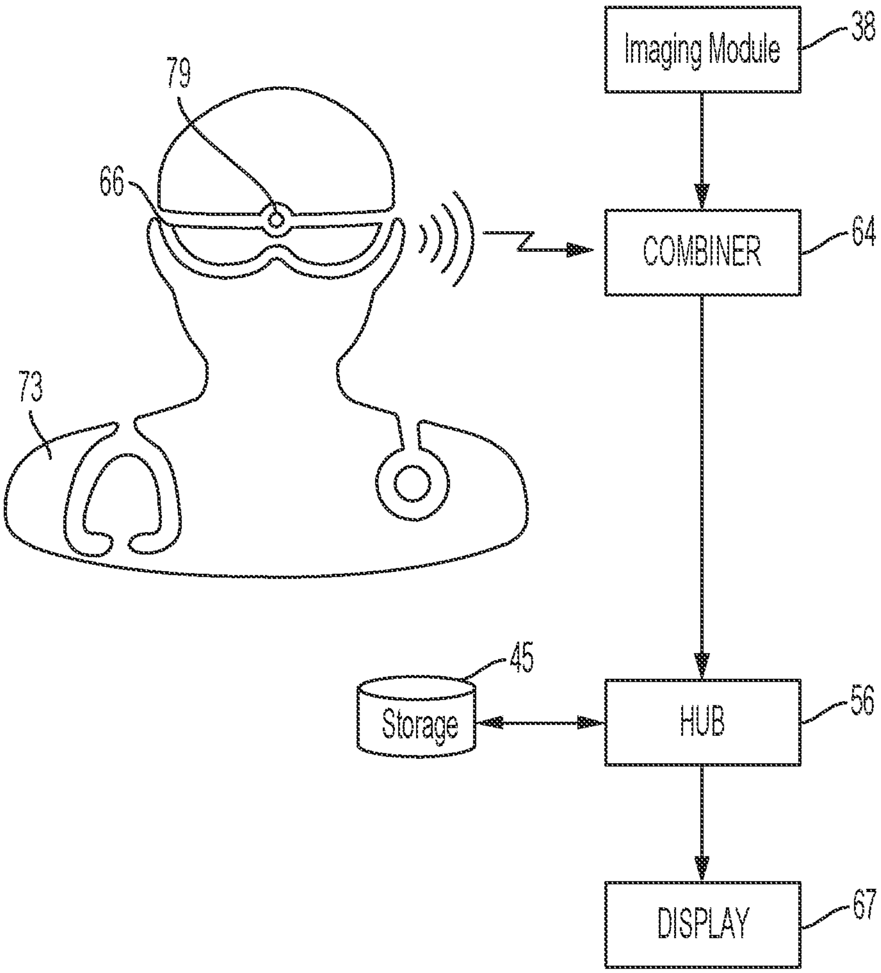
FIG. 8 illustrates an augmented reality (AR) system comprising an intermediate signal combiner positioned in the communication path between an imaging module and a surgical hub display, according to one aspect of this disclosure.

FIG. 8 illustrates an augmented reality (AR) system comprising an intermediate signal combiner positioned in the communication path between an imaging module and a surgical hub display. FIG. 8 illustrates an AR device 66 worn by a surgeon 73 to communicate data to the surgical hub 56. Peripheral information of the AR device 66 does not include active video. Rather, the peripheral information includes only device settings, or signals that do not have same demands of refresh rates. Interaction may augment the surgeon's 73 information based on linkage with preoperative computerized tomography (CT) or other data linked in the surgical hub 56. The AR device 66 can identify structure—ask whether instrument is touching a nerve, vessel, or adhesion, for example. The AR device 66 may include pre-operative scan data, an optical view, tissue interrogation properties acquired throughout procedure, and/or processing in the surgical hub 56 used to provide an answer. The surgeon 73 can dictate notes to the AR device 66 to be saved with patient data in the hub storage 45 for later use in report or in follow up.

The AR device 66 worn by the surgeon 73 links to the surgical hub 56 with audio and visual information to avoid the need for overlays, and allows customization of displayed information around periphery of view. The AR device 66 provides signals from devices (e.g., instruments), answers queries about device settings, or positional information linked with video to identify quadrant or position. The AR device 66 has audio control and audio feedback from the AR device 66. The AR device 66 is able to interact with other systems in the operating theater and have feedback and interaction available wherever the surgeon 73 is viewing. For example, the AR device 66 may receive voice or gesture initiated commands and queries from a surgeon, and the AR device 66 may provide feedback in the form of one or more modalities including audio, visual, or haptic touch.

Figure 9:
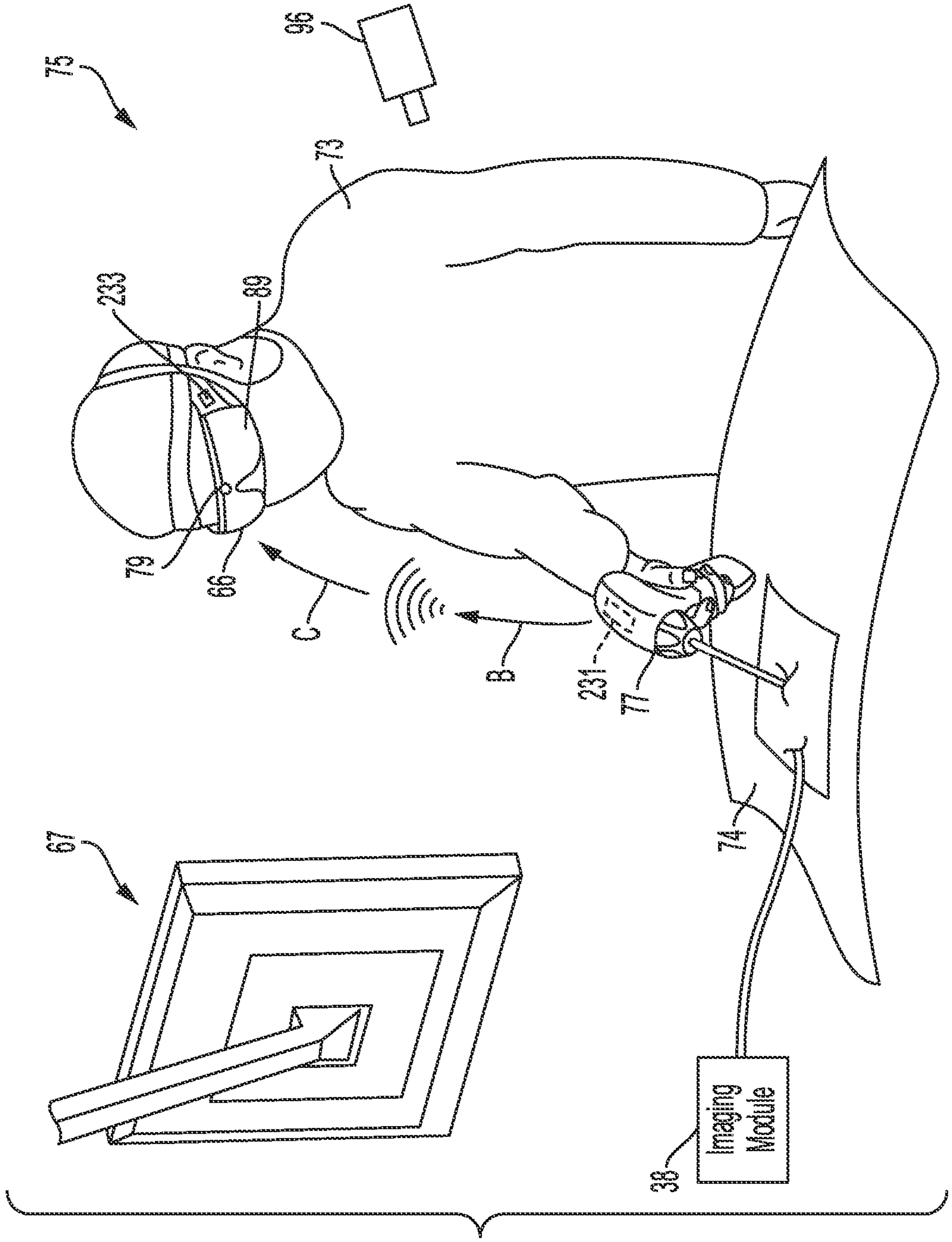
FIG. 9 illustrates an augmented reality (AR) device worn by a surgeon to communicate data to the surgical hub, according to one aspect of this disclosure.

FIG. 9 illustrates a surgeon 73 wearing an AR device 66, a patient 74, and may include a camera 96 in an operating room 75. The AR device 66 worn by the surgeon 73 may be used to present to the surgeon 73 a virtual object overlaid on a real time image of the surgical field through augmented reality display 89 or through the hub connected display 67. The real time image may include a portion of a surgical instrument 77. The virtual object may not be visible to others within the operating room 75 (e.g., surgical assistant or nurse), though they also may wear AR devices 66. Even if another person is viewing the operating room 75 with an AR device 66, the person may not be able to see the virtual object or may be able to see the virtual object in a shared augmented reality with the surgeon 73, or may be able to see a modified version of the virtual object (e.g., according to customizations unique to the surgeon 73) or may see different virtual objects.

A virtual object and/or data may be configured to appear on a portion of a surgical instrument 77 or in a surgical field of view captured by an imaging module 38, an imaging device 68 during minimally invasive surgical procedures, and/or the camera 96 during open surgical procedures. In the illustrated example, the imaging module 38 is a laparoscopic camera that provides a live feed of a surgical area during a minimally invasive surgical procedure. An AR system may present virtual objects that are fixed to a real object without regard to a perspective of a viewer or viewers of the AR system (e.g., the surgeon 73). For example, a virtual object may be visible to a viewer of the AR system inside the operating room 75 and not visible to a viewer of the AR system outside the operating room 75. The virtual object may be displayed to the viewer outside the operating room 75 when the viewer enters the operating room 75. The augmented image may be displayed on the surgical hub display 67 or the augmented reality display 89.

The AR device 66 may include one or more screens or lens, such as a single screen or two screens (e.g., one per eye of a user). The screens may allow light to pass through the screens such that aspects of the real environment are visible while displaying the virtual object. The virtual object may be made visible to the surgeon 73 by projecting light. A virtual object may appear to have a degree of transparency or may be opaque (i.e., blocking aspects of the real environment).

An AR system may be viewable to one or more viewers, and may include differences among views available for the one or more viewers while retaining some aspects as universal among the views. For example, a heads-up display may change between two views while virtual objects and/or data may be fixed to a real object or area in both views. Aspects such as a color of an object, lighting, or other changes may be made among the views without changing a fixed position of at least one virtual object.

A user may see a virtual object and/or data presented in an AR system as opaque or as including some level of transparency. In an example, the user may interact with the virtual object, such as by moving the virtual object from a first position to a second position. For example, the user may move an object with his or her hand. This may be done in the AR system virtually by determining that the hand has moved into a position coincident or adjacent to the object (e.g., using one or more cameras, which may be mounted on the AR device 66, such as AR device camera 79 or separate 96, and which may be static or may be controlled to move), and causing the object to move in response. Virtual aspects may include virtual representations of real world objects or may include visual effects, such as lighting effects, etc. The AR system may include rules to govern the behavior of virtual objects, such as subjecting a virtual object to gravity or friction, or may include other predefined rules that defy real world physical constraints (e.g., floating objects, perpetual motion, etc.). The AR device 66 may include a camera 79 on the AR device 66 (not to be confused with the camera 96, separate from the AR device 66). The AR device camera 79 or the camera 96 may include an infrared camera, an infrared filter, a visible light filter, a plurality of cameras, a depth camera, etc. The AR device 66 may project virtual items over a representation of a real environment, which may be viewed by a user.

The AR device 66 may be used in the operating room 75 during a surgical procedure, for example performed by the surgeon 73 on the patient 74. The AR device 66 may project or display virtual objects, such as a virtual object during the surgical procedure to augment the surgeon's vision. The surgeon 73 may view a virtual object using the AR device 66, a remote controller for the AR device 66, or may interact with a virtual object, for example, using a hand to "interact" with a virtual object or a gesture recognized by the camera 79 of the AR device 66. A virtual object may augment a surgical tool such as the surgical instrument 77. For example, the virtual object may appear (to the surgeon 73 viewing the virtual object through the AR device 66) to be coupled with or remain a fixed distance from the surgical instrument 77. In another example, the virtual object may be used to guide the surgical instrument 77, and may appear to be fixed to the patient 74. In certain examples, a virtual object may react to movements of other virtual or real-world objects in the surgical field. For example, the virtual object may be altered when a surgeon is manipulating a surgical instrument in proximity to the virtual object.

The augmented reality display system imaging device 38 capture a real image of a surgical area during a surgical procedure. An augmented reality display 89, 67 presents an overlay of an operational aspect of the surgical instrument 77 onto the real image of the surgical area. The surgical instrument 77 includes communications circuitry 231 to communicate operational aspects and functional data from the surgical instrument 77 to the AR device 66 via communication communications circuitry 233 on the AR device 66. Although the surgical instrument 77 and the AR device 66 are shown in RF wireless communication between circuits 231, 233 as indicated by arrows B, C, other communication techniques may employed (e.g., wired, ultrasonic, infrared, etc.). The overlay is related to the operational aspect of the surgical instrument 77 being actively visualized. The overlay combines aspects of tissue interaction in the surgical area with functional data from the surgical instrument 77. A processor portion of the AR device 66 is configured to receive the operational aspects and functional data from the surgical instrument 77, determine the overlay related to the operation of the surgical instrument 77, and combine the aspect of the tissue in the surgical area with the functional data from the surgical instrument 77. The augmented images indicate alerts relative to device performance considerations, alerts of incompatible usage, alerts on incomplete capture. Incompatible usage includes tissue out range conditions and tissue incorrectly balanced within the jaws of the end effector. Additional augmented images provide an indication of collateral events including indication of tissue tension and indication of foreign object detection. Other augmented images indicate device status overlays and instrument indication.

FIG. 10 illustrates a system 83 for augmenting images of a surgical field with information using an AR display 89, according to one aspect of this disclosure. The system 83 may be used to perform the techniques described hereinbelow, for example, by using the processor 85. The system 83 includes one aspect of an AR device 66 that may be in communication with a database 93. The AR device 66 includes a processor 85, memory 87, an AR display 89, and a camera 79. The AR device 66 may include a sensor 90, a speaker 91, and/or a haptic controller 92. The database 93 may include image storage 94 or preoperative plan storage 95.

The processor 85 of the AR device 66 includes an augmented reality modeler 86. The augmented reality modeler 86 may be used by the processor 85 to create the augmented reality environment. For example, the augmented reality modeler 86 may receive images of the instrument in a surgical field, such as from the camera 79 or sensor 90, and create the augmented reality environment to fit within a display image of the surgical field of view. In another example, physical objects and/or date may be overlaid on the surgical field of view and/or the surgical instruments images and the augmented reality modeler 86 may use physical objects and data to present the augmented reality display of virtual object s and/or data in the augmented reality environment. For example, the augmented reality modeler 86 may use or detect an instrument at a surgical site of the patient and present a virtual object and/or data on the surgical instrument and/or an image of the surgical site in the surgical field of view captured by the camera 79. The AR display 89 may display the AR environment overlaid on a real environment. The display 89 may show a virtual object and/or data, using the AR device 66, such as in a fixed position in the AR environment.

The AR device 66 may include a sensor 90, such as an infrared sensor. The camera 79 or the sensor 90 may be used to detect movement, such as a gesture by a surgeon or other user, that may be interpreted by the processor 85 as attempted or intended interaction by the user with the virtual target. The processor 85 may identify an object in a real environment, such as through processing information received using the camera 79. In other aspects, the sensor 90 may be a tactile, audible, chemical, or thermal sensor to generate corresponding signals that may combined with various data feeds to create the augmented environment. The sensor 90 may include binaural audio sensors (spatial sound), inertial measurement (accelerometer, gyroscope, magnetometer) sensors, environmental sensors, depth camera sensors, hand and eye tracking sensors, and voice command recognition functions.

The AR display 89, for example during a surgical procedure, may present, such as within a surgical field while permitting the surgical field to be viewed through the AR display 89, a virtual feature corresponding to a physical feature hidden by an anatomical aspect of a patient. The virtual feature may have a virtual position or orientation corresponding to a first physical position or orientation of the physical feature. In an example, the virtual position or orientation of the virtual feature may include an offset from the first physical position or orientation of the physical feature. The offset may include a predetermined distance from the augmented reality display, a relative distance from the augmented reality display to the anatomical aspect, or the like.

In one example, the AR device 66 may be an individual AR device. In one aspect, the AR device 66 may be a HoloLens 2 AR device manufactured by Microsoft of Redmond, Wash. This AR device 66 includes a visor with lenses and binaural audio features (spatial sound), inertial measurement (accelerometer, gyroscope, magnetometer), environmental sensors, depth camera, and video camera, hand and eye tracking, and voice command recognition functions. It provides an improved field of view with high resolution by using mirrors to direct waveguides in front of wearer's eyes. Images can be enlarged by changing angles of mirrors. It also provides eye tracking to recognize users and adjust lens widths for specific users.

In another example, the AR device 66 may be a Snapchat Spectacles 3 AR device. This AR device provides the ability to capture paired images and recreate 3D depth mapping, add in virtual effects, and replay 3D videos. The AR device includes two HD cameras to capture 3D photos and videos at 60 fps—while four built-in microphones record immersive, high-fidelity audio. Images from both cameras combine to build out a geometric map of the real world around the user to provide a new sense of depth perception. Photos and videos may be wirelessly synchronized to external display devices.

In yet another example, the AR device 66 may be a Glass 2 AR device by Google. This AR device provides inertial measurement (accelerometer, gyroscope, magnetometer) information overlaid on lens (out of view) to supplement information.

In another example, the AR device 66 may be an Echo Frames AR device by Amazon. This AR device does not have cameras/displays. A microphone and speaker are linked to Alexa. This AR device provides less functionality than a heads-up display.

In yet another example, the AR device 66 may be a Focals AR device by North (Google). This AR device provides notification pusher/smartwatch analog; inertial measurement, screen overlay of information (weather, calendar, messages), voice control (Alexa) integration. This AR device provides basic heads-up display functionality.

In another example, the AR device 66 may be an Nreal AR device. This AR device includes spatial sound, two environmental cameras, a photo camera, IM U (accelerometer, gyroscope), ambient light sensor, proximity sensor functionality. A nebula projects application information on lenses.

In various other examples, the AR device 66 may be any one of the following commercially available AR devices: Magic Leap 1, Epson Moverio, Vuzix Blade AR, ZenFone AR, Microsoft AR glasses prototype, EyeTap to create collinear light to that of the environment directly into the retina. A beam splitter makes the same light seen by the eye available to the computer to process and overlay information, for example. AR visualization systems include HUD, contact lenses, glasses, virtual reality (VR) headsets, virtual retinal display, on in operating room displays, and/or smart contact lenses (bionic lenses).

Multi-user interfaces for the AR device 66 include virtual retinal displays such as raster displays drawn directly on retinas instead of on a screen in front of the eye, smart televisions, smart phones, and/or spatial displays such as Sony spatial display systems.

Other AR technology may include, for example, AR capture devices and software applications, AR creation devices and software applications, and AR cloud devices and software applications. AR capture devices and software applications include, for example, Apple Polycam app, Ubiquity 6 (Mirrorworld using Display.land app)—users can scan and get 3d image of real world (to create 3D model). AR creation devices and software applications include, for example, Adobe Aero, Vuforia, ARToolKit, Google ARCore, Apple ARKit, MAXST, Aurasma, Zappar, Blippar. AR cloud devices and software applications include, for example, Facebook, Google (world geometry, objection recognition, predictive data), Amazon AR Cloud (commerce), Microsoft Azure, Samsung Project Whare, Niantic, Magic Leap.

Situational awareness is the ability of some aspects of a surgical system to determine or infer information related to a surgical procedure from data received from databases and/or instruments. The information can include the type of procedure being undertaken, the type of tissue being operated on, or the body cavity that is the subject of the procedure. With the contextual information related to the surgical procedure, the surgical system can, for example, improve the manner in which it controls the modular devices (e.g., a robotic arm and/or robotic surgical tool) that are connected to it and provide contextualized information or suggestions to the surgeon during the course of the surgical procedure.

Figure 11:
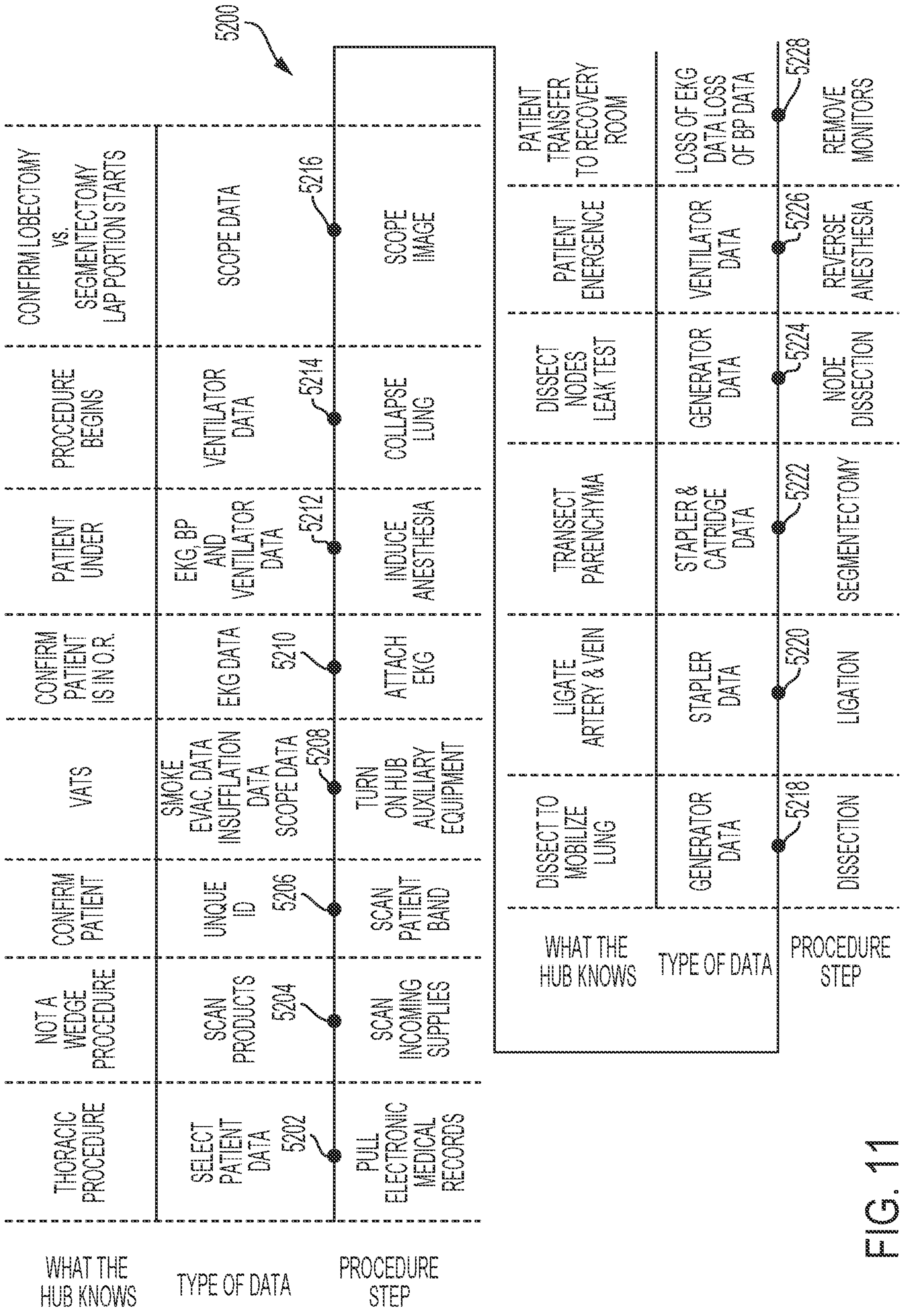
FIG. 11 illustrates a timeline of a situational awareness surgical procedure, according to one aspect of this disclosure.

FIG. 11 illustrates a timeline of a situational awareness surgical procedure. FIG. 11 illustrates a timeline 5200 of an illustrative surgical procedure and the contextual information that a surgical hub 5104 can derive from the data received from the data sources 5126 at each step in the surgical procedure. The timeline 5200 depicts the typical steps that would be taken by the nurses, surgeons, and other medical personnel during the course of a lung segmentectomy procedure, beginning with setting up the operating theater and ending with transferring the patient to a post-operative recovery room. The situationally aware surgical hub 5104 receives data from the data sources 5126 throughout the course of the surgical procedure, including data generated each time medical personnel utilize a modular device 5102 that is paired with the surgical hub 5104. The surgical hub 5104 can receive this data from the paired modular devices 5102 and other data sources 5126 and continually derive inferences (i.e., contextual information) about the ongoing procedure as new data is received, such as which step of the procedure is being performed at any given time. The situational awareness system of the surgical hub 5104 is able to, for example, record data pertaining to the procedure for generating reports, verify the steps being taken by the medical personnel, provide data or prompts (e.g., via a display screen) that may be pertinent for the particular procedural step, adjust modular devices 5102 based on the context (e.g., activate monitors, adjust the FOV of the medical imaging device, or change the energy level of an ultrasonic surgical instrument or RF electrosurgical instrument), and take any other such action described above.

First 5202, the hospital staff members retrieve the patient's EMR from the hospital's EMR database. Based on select patient data in the EMR, the surgical hub 5104 determines that the procedure to be performed is a thoracic procedure.

Second 5204, the staff members scan the incoming medical supplies for the procedure. The surgical hub 5104 cross-references the scanned supplies with a list of supplies that are utilized in various types of procedures and confirms that the mix of supplies corresponds to a thoracic procedure. Further, the surgical hub 5104 is also able to determine that the procedure is not a wedge procedure (because the incoming supplies either lack certain supplies that are necessary for a thoracic wedge procedure or do not otherwise correspond to a thoracic wedge procedure).

Third 5206, the medical personnel scan the patient band via a scanner 5128 that is communicably connected to the surgical hub 5104. The surgical hub 5104 can then confirm the patient's identity based on the scanned data.

Fourth 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices 5102 can automatically pair with the surgical hub 5104 that is located within a particular vicinity of the modular devices 5102 as part of their initialization process. The surgical hub 5104 can then derive contextual information about the surgical procedure by detecting the types of modular devices 5102 that pair with it during this pre-operative or initialization phase. In this particular example, the surgical hub 5104 determines that the surgical procedure is a VATS procedure based on this particular combination of paired modular devices 5102. Based on the combination of the data from the patient's EMR, the list of medical supplies to be used in the procedure, and the type of modular devices 5102 that connect to the hub, the surgical hub 5104 can generally infer the specific procedure that the surgical team will be performing. Once the surgical hub 5104 knows what specific procedure is being performed, the surgical hub 5104 can then retrieve the steps of that procedure from a memory or from the cloud and then cross-reference the data it subsequently receives from the connected data sources 5126 (e.g., modular devices 5102 and patient monitoring devices 5124) to infer what step of the surgical procedure the surgical team is performing.

Fifth 5210, the staff members attach the EKG electrodes and other patient monitoring devices 5124 to the patient. The EKG electrodes and other patient monitoring devices 5124 are able to pair with the surgical hub 5104. As the surgical hub 5104 begins receiving data from the patient monitoring devices 5124, the surgical hub 5104 thus confirms that the patient is in the operating theater.

Sixth 5212, the medical personnel induce anesthesia in the patient. The surgical hub 5104 can infer that the patient is under anesthesia based on data from the modular devices 5102 and/or patient monitoring devices 5124, including EKG data, blood pressure data, ventilator data, or combinations. Upon completion of the sixth step 5212, the pre-operative portion of the lung segmentectomy procedure is completed and the operative portion begins.

Seventh 5214, the patient's lung that is being operated on is collapsed (while ventilation is switched to the contralateral lung). The surgical hub 5104 can infer from the ventilator data that the patient's lung has been collapsed. The surgical hub 5104 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth 5216, the medical imaging device 5108 (e.g., a scope) is inserted and video from the medical imaging device is initiated. The surgical hub 5104 receives the medical imaging device data (i.e., still image data or live streamed video in real time) through its connection to the medical imaging device. Upon receipt of the medical imaging device data, the surgical hub 5104 can determine that the laparoscopic portion of the surgical procedure has commenced. Further, the surgical hub 5104 can determine that the particular procedure being performed is a segmentectomy, as opposed to a lobectomy (note that a wedge procedure has already been discounted by the surgical hub 5104 based on data received at the second step 5204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 5104), and monitoring the types of visualization devices utilized.

For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device 5108, the surgical hub 5104 can thereby determine the specific type of surgical procedure being performed and/or the technique being used for a particular type of surgical procedure.

Ninth 5218, the surgical team begins the dissection step of the procedure. The surgical hub 5104 can infer that the surgeon is in the process of dissecting to mobilize the patient's lung because it receives data from the RF or ultrasonic generator indicating that an energy instrument is being fired. The surgical hub 5104 can cross-reference the received data with the retrieved steps of the surgical procedure to determine that an energy instrument being fired at this point in the process (i.e., after the completion of the previously discussed steps of the procedure) corresponds to the dissection step.

Tenth 5220, the surgical team proceeds to the ligation step of the procedure. The surgical hub 5104 can infer that the surgeon is ligating arteries and veins because it receives data from the surgical stapling and cutting instrument indicating that the instrument is being fired. Similarly to the prior step, the surgical hub 5104 can derive this inference by cross-referencing the receipt of data from the surgical stapling and cutting instrument with the retrieved steps in the process.

Eleventh 5222, the segmentectomy portion of the procedure is performed. The surgical hub 5104 infers that the surgeon is transecting the parenchyma based on data from the surgical instrument, including data from a staple cartridge. The cartridge data may correspond to size or type of staple being fired by the instrument. The cartridge data can indicate the type of tissue being stapled and/or transected for different types of staples utilized in different types of tissues. The type of staple being fired is utilized for parenchyma or other tissue types to allow the surgical hub 5104 to infer that the segmentectomy procedure is being performed.

Twelfth 5224, the node dissection step is then performed. The surgical hub 5104 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 5104 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Upon completion of the twelfth step 5224, the incisions and closed up and the post-operative portion of the procedure begins.

Thirteenth 5226, the patient's anesthesia is reversed. The surgical hub 5104 can infer that the patient is emerging from the anesthesia based on the ventilator data (i.e., the patient's breathing rate begins increasing), for example.

Lastly, fourteenth 5228, the medical personnel remove the various patient monitoring devices 5124 from the patient. The surgical hub 5104 can thus infer that the patient is being transferred to a recovery room when the hub loses EKG, BP, and other data from the patient monitoring devices 5124. The surgical hub 5104 can determine or infer when each step of a given surgical procedure is taking place according to data received from the various data sources 5126 that are communicably coupled to the surgical hub 5104.

In addition to utilizing the patient data from EMR database(s) to infer the type of surgical procedure that is to be performed, as illustrated in the first step 5202 of the timeline 5200 depicted in FIG. 11, the patient data can also be utilized by a situationally aware surgical hub 5104 to generate control adjustments for the paired modular devices 5102.

Figure 12:
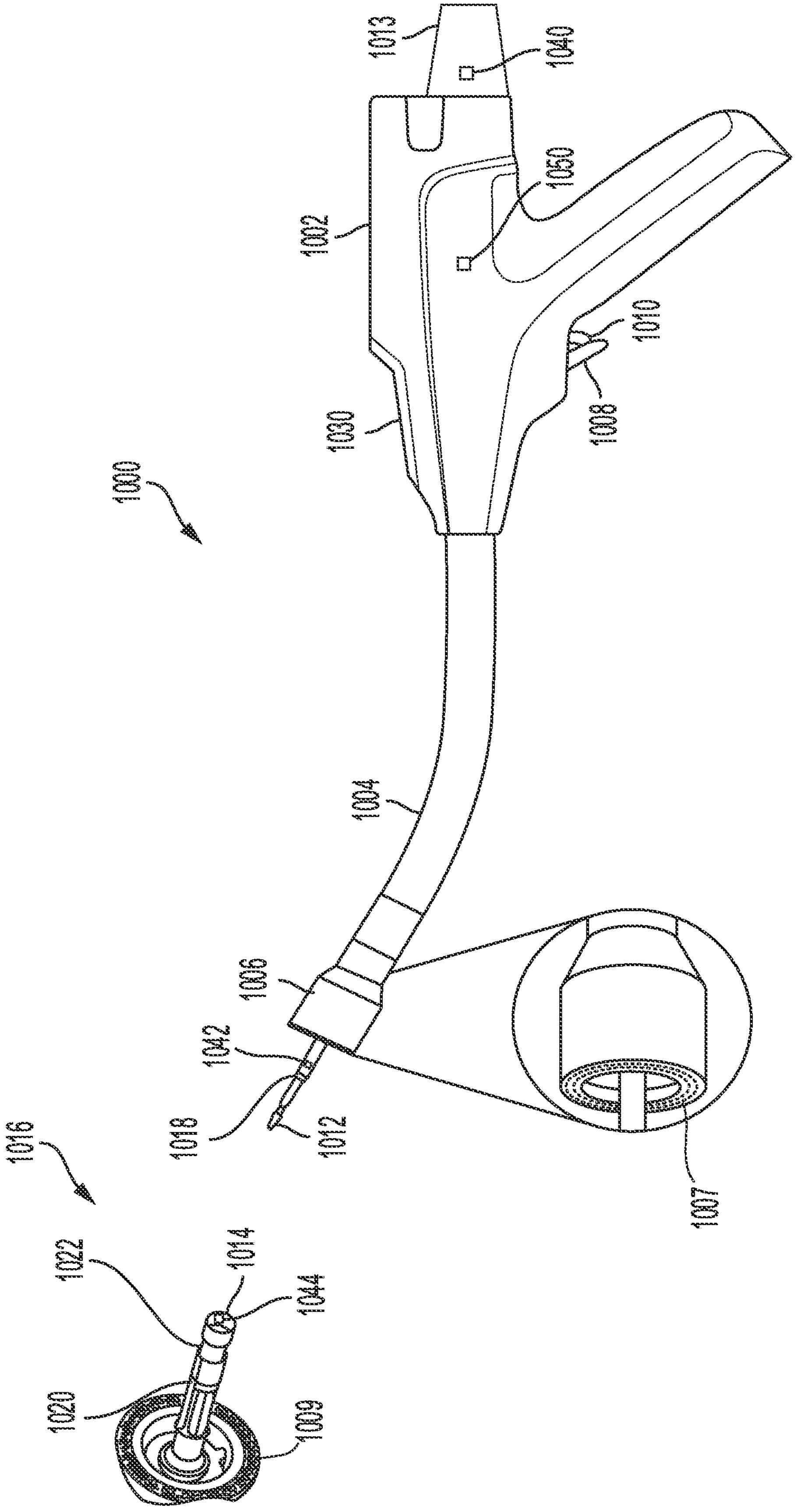
FIG. 12 illustrates a circular stapler, according to at least one aspect of the present disclosure.

Referring now to FIG. 12, a circular stapler 1000 is provided according to at least one aspect of the present disclose. The circular stapler 1000 comprises a housing 1002, a shaft 1004 extending from the housing 1002, and an end effector 1006 extending from the shaft 1004. In various embodiments, the housing 1002 comprises a handle that is grasped by a user of the circular stapler 1000. The end effector 1006 is sized to receive a staple cartridge 1007 therein that includes staples that are deployable from the staple cartridge 1007 into tissue. In various embodiments, the stapler cartridge 1007 comprises a cartridge body, an annular array of staple cavities defined in the cartridge body, and staples removably stored in the annular array of staple cavities. The circular stapler 1000 further includes a firing drive that is configured to drive the staples from the staple cavities into tissue and drive a knife into the stapled tissue, based on actuation of a firing trigger 1008 on the housing 1002. The housing 1002 further includes a safety 1010 configured to prevent inadvertent actuation of the firing trigger 1008 by engaging the firing trigger 1008 until the safety 1010 is manually moved away from the firing trigger 1008.

The circular stapler 1000 further includes a trocar 1012 that is sized and configured to couple to an anvil shaft 1014 of an anvil 1016. In some embodiments, the trocar 1012 is manually extendable and retractable relative to the end effector 1006 by a manual adjustment knob, or rotary actuator, 1013 on the proximal end of the housing 1002. In some embodiments, the trocar 1012 is extendable and retractable relative to the end effector 1006 by a motor-driven system. The trocar 1012 includes a band 1018 thereon for providing visual feedback regarding the trocar 1012, such as a visual indication of the location of the trocar 1012 or for visually determining if the anvil 1016 is coupled to the trocar 1012, as explained below.

Figure 19:
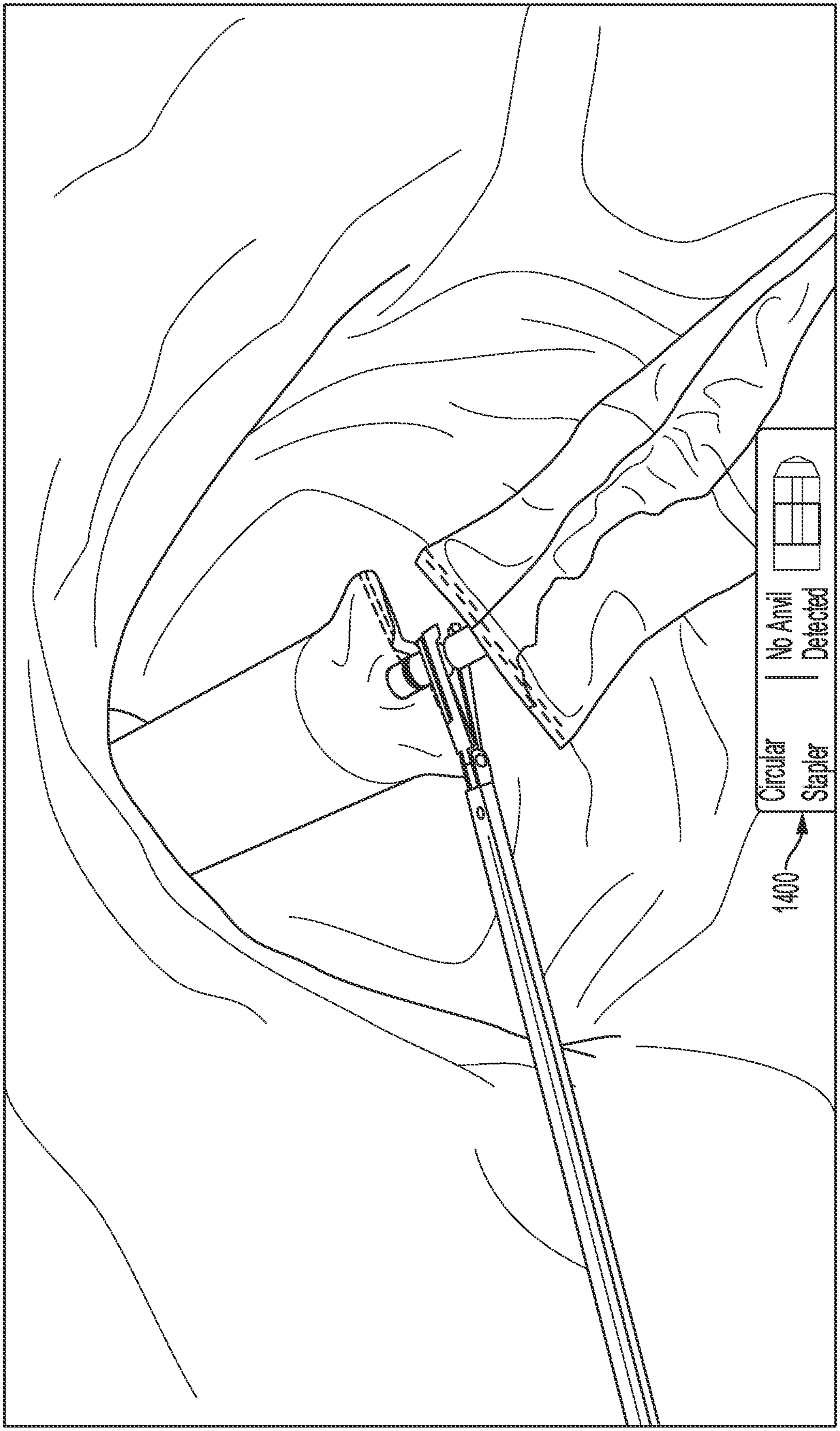

In operation, the trocar 1012 is inserted into the anvil shaft 1014 until locking springs 1020 of the anvil 1016 lock onto the trocar 1012, thereby releasably coupling the anvil 1016 to the trocar 1012. In one aspect, the anvil 1016 is coupled to the trocar 1012 by grasping a grasping area 1022 of the anvil 1016 with a grasping tool and moving the anvil 1016 toward the trocar 1012, as can be seen in FIG. 19, as an example. In the coupled state, the anvil shaft 1014 covers the band 1018, providing visual confirmation to a user that the anvil 1016 is coupled to the trocar 1012. Once the anvil 1016 is coupled to the trocar 1012, a user can adjust the position of the anvil 1016 relative to the staple cartridge 1007. For instance, in some embodiments, the user can move/rotate the manually adjustable knob 1013 on the housing 1002, which moves the trocar 1012, and therefore, the anvil 1016. A user can rotate the knob 1013 a first direction to move the anvil 1016 toward the staple cartridge 1007 and end effector 1006 by way of trocar 1012 to capture tissue between the anvil 1016 and the staple cartridge 1007. Similarly, a user can rotate the knob 1013 in a second direction opposite the first direction to move the anvil 1016 away from the staple cartridge 1007 and the end effector 1006 by way of trocar 1012. Other embodiments are envisioned in which the user adjusts the position of the anvil 1016 relative to the staple cartridge 1007 using the motor drive system, referenced above.

Once the user is satisfied with the position of the anvil 1016, the user can move the safety 1010 out of engagement with the firing trigger 1008 and actuate the firing trigger 1008. Based on the actuation of the firing trigger 1008, the firing drive drives the staples from the staple cartridge 1007 through tissue captured between the anvil 1016 and staple cartridge 1007 and into staple pockets 1009 defined in the anvil 1016 to form the staples. In addition, the knife cuts the stapled tissue, based on the actuation of the firing trigger. In many instances, the circular stapler 1000 includes a display 1030 to provide visual feedback to the user, as will be described in more detail below.

In various embodiments, the rotary actuator 1013 comprises a sensor 1040 that is configured to sense various parameters associated with the circular stapler 1000. In some embodiments, the sensor 1040 senses rotational motion of the rotary actuator 1013, which is indicative of the longitudinal position of the trocar 1012 and the anvil 1016 relative to the end effector 1006. In various embodiments, the sensor 1040 senses a torque a user applies to the rotary actuator 1013, which is indicative of the force the anvil 1016 is applying to tissue captured between the anvil 1016 and the end effector 1006.

In various embodiments, the trocar 1012 comprises a sensor 1042 that is configured to sense various parameters associated with the circular stapler 1000. In some embodiments, the sensor 1042 senses a longitudinal position of the trocar 1012 relative to the end effector 1006, and thus, a relative position of the anvil 1016 relative to the end effector 1006. In various embodiments, the sensor 1042 senses a force that the trocar 1012 is experiencing, which is indicative of the force the anvil 1016 is applying to tissue captured between the anvil 1016 and the end effector 1006. In some embodiments, the sensor 1042 senses when the anvil 1016 is connected to the trocar 1012.

In various embodiments, the anvil 1016 comprises a sensor 1044 that is configured to sense various parameters associated with the circular stapler 1000. In some embodiments, the sensor 1044 senses when the anvil 1016 has been connected to the trocar 1012. In some embodiments, the anvil 1016 senses a position thereof relative to the end effector. In some embodiments, the anvil 1016 senses a force that is being applied to tissue captured between the anvil 1016 and the end effector 1006.

In various embodiments, the circular stapler further comprises a control system 1050 that is configured to control various aspects of the circular stapler 1000. In some embodiments, the control system 1030 is in wired or wireless communication with the various sensors 1040, 1042, 1044 and can interrogate the sensors 1040, 1042, 1042 to determine what is being sensed. Based on the determination, the control system 1050 controls various aspects of the circular stapler 1000. In some embodiments, based on the determination, the control system adjusts the display 1030. For instance, based on the determination, the control system 1050 displays a representation of the determined parameters on the display 1030, as will be explained in greater detail below.

Various other circular staplers are described in U.S. Pat. Nos. 8,066,167, 8,353,438, 8,672,207, 8,801,734, 8,801,735, 8,827,903, 8,622,275, 8,899,466, 8,978,955, 9,033,204, 9,113,883, 9,125,654, 10,426,476, 10,980,538, 11,284,890, 10,675,021, 10,682,136, which are hereby incorporated by reference in their entireties herein.

Embodiment A: Indicator Position Feedback

Figure 13E:
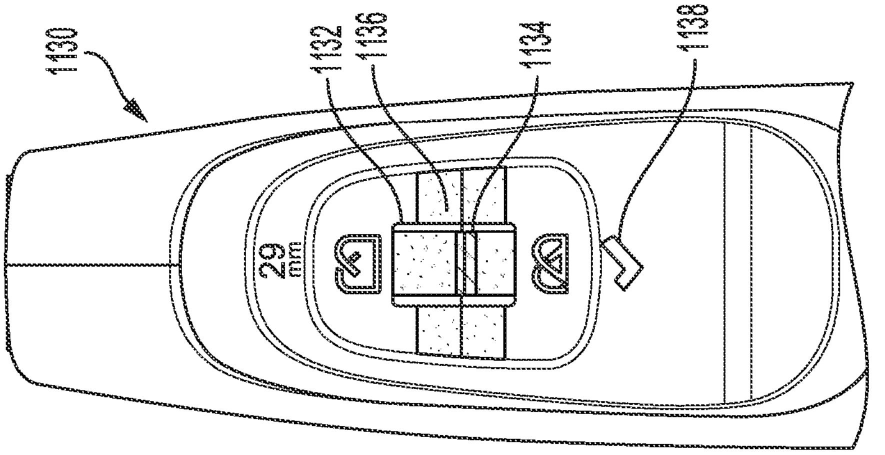
FIG. 13E illustrates a display on a housing of a circular stapler, according to at least one aspect of the present disclosure.
Figure 13A:
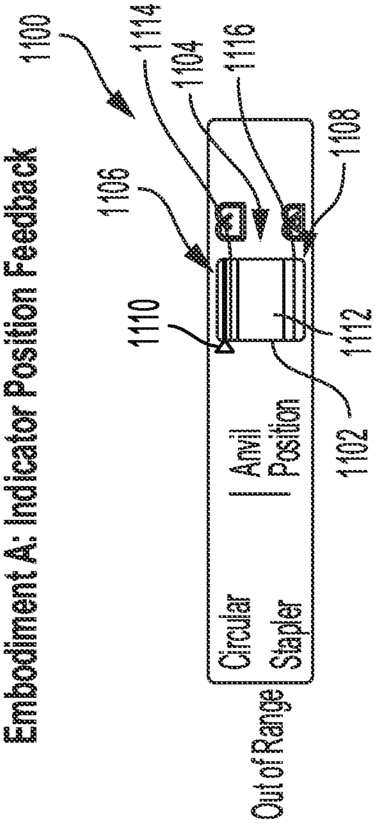
FIG. 13A illustrates a vertically-oriented display indicating that an anvil is out of range, according to at least one aspect of the present disclosure.
Figure 13B:
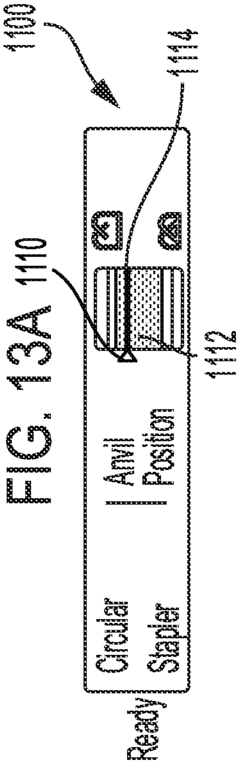
FIG. 13B illustrates the vertically oriented display of FIG. 13A indicating that the anvil is within range and ready to fire, according to at least one aspect of the present disclosure.

FIGS. 13A and 13B illustrate a display 1100 for providing visual feedback to a user of a circular stapler, according to at least one aspect of the present disclosure. In various embodiments, the display 1100 is incorporated into the housing 1002 of the circular stapler 1000. In various embodiments, the display 1100 is shown on display 1030. In various other embodiments, the display 1100 is visually displayed on a display, such as display 7, display 9, display 19, within a display of the surgeon console 18, on AR device 66, or any other suitable location described herein that is configured to convey visual information to a user. In various embodiments, the display 1100 is in operable communication with a control system, such as control system 1030, that controls various aspects of the display 1100, as described herein below. In various embodiments, the control system comprises a processor and a memory storing instructions that are executable by the processor. In various embodiments, the control system is any suitable controller, control circuit, hub, or the like described herein.

The display 1100 provides visual feedback to a user indicative of the position of the anvil, such as anvil 1016, relative to the staple cartridge, such as staple cartridge 1007. In various embodiments, the display 1100 includes a vertically extending bar 1102 that defines an acceptable zone 1104 and unacceptable zones 1106, 1108 surrounding the acceptable zone 1104. As shown in FIG. 13A, the unacceptable zone 1106 and the acceptable zone 1104 are separated by threshold boundary 1114 that is visible to the user. Similarly, the unacceptable zone 1108 and the acceptable zone 1104 are separated by threshold boundary 1116 that is visible to the user. In one aspect, the acceptable zone 1104 corresponds to positions of the anvil relative to the staple cartridge that are suitable for firing staples from the staple cartridge. In one aspect, the unacceptable zone 1106 corresponds to positions of the anvil that are too far, such as over a threshold limit, away from the staple cartridge, and thus, is not suitable for firing staples from the staple cartridge. In one aspect, the unacceptable zone 1108 corresponds to positions of the anvil that are too close, such as under a threshold limit, to the staple cartridge, and thus, is not suitable for firing staples from the staple cartridge. In various embodiments, the size of the zones 1104, 1106, 1108 are be predefined, stored in a memory, and are be retrievable by the control system. Various other embodiments are envisioned where the size of the zones 1104, 1106, 1108 and the positions of threshold boundaries 1114, 1116 are set by a user at a user interface.

In some embodiments, when the anvil is initially coupled to the trocar of the surgical instrument, the control system detects the attached of the anvil and generates an indicator 1110 on the display 1100 to identify a position on the bar 1102. As seen in FIG. 13A, when the anvil is initially attached, the control system detects the position of the anvil and positions indicator 1110 within unacceptable zone 1106 as the detected position of the anvil is too far away from the staple cartridge. The control system detects the attachment of the anvil utilizing any suitable sensors, detectors, or the like, as described elsewhere herein. In various embodiments, the control system detects the attachment of the anvil utilizing an anvil connectivity sensor integrated with the anvil, such as sensor 1044. Accordingly, the control system communicates with various sensors within the anvil, such as force and/or position sensors, as examples, such that the control circuit can receive, process, and/or wirelessly transmit data from the anvil sensors to other pieces of equipment in the OR for display to users. The indicator 1110 pointing to the unacceptable zone 1106 indicates to a user that the anvil is positioned too far away from the staple cartridge, i.e., 'out of range', and that the anvil should be moved closer to the staple cartridge, such as utilizing the manually retraction knob 1013 on the housing or the motorized system. When the anvil is within one of unacceptable zones 1106, 1108, a portion 1112 of the bar 1102 is displayed, or illuminated, a first color, such as gray, to indicate that the stapler is not ready for firing. In some embodiments, the control system prevents actuation of the firing drive to deploy the staples from the staple cartridge 1007 based on the determination of the indicator 1110 being positioned within one of the unacceptable zones 1106, 1108.

When the display 1100 indicates that the anvil is within the unacceptable zone 1106, the user can utilize the retraction knob 1013 or motorized system to move the anvil toward the staple cartridge (via trocar). As the user retracts the anvil, the control system detects the movement of the anvil (using any number of position sensors or the like, described elsewhere herein) to cause the indicator 1110 to move along bar 1102, relative to the zones 1104, 1106, 1108, to visually communicate to the user that the anvil is approaching acceptable zone 1104. In various embodiments, the circular stapler includes a rotational position sensor, such as sensor 1040, that measures the rotations of the retraction knob 1013 to determine a position of the anvil relative to the staple cartridge. In various embodiments, the circular stapler includes a linear position sensor, such as sensor 1042, to measure movement of various components of the stapler, such as the trocar itself, to determine a position of the anvil relative to the staple cartridge. Once the indicator 1110 has reached the acceptable zone 1104, indicating that the circular stapler is in a 'ready-to-fire' state (FIG. 13B), the control system causes the portion 1112 of the bar 1102 to illuminate, or display, a second color different than the first color, such as green, indicating to a user that the anvil is within the acceptable zone 1104, and thus, the stapler can be fired. In various other embodiments, the control system actuates a haptic feedback module to inform the user that the anvil is within the acceptable zone 1104. In various other embodiments, the control system actuates an auditory module to provide auditory feedback to inform the user that the anvil is within the acceptable zone 1104. In various embodiments, the circular stapler includes a lockout that prevent the user from actuating the firing drive unless the control system determines that the anvil is within the acceptable zone 1104.

Figure 13C:
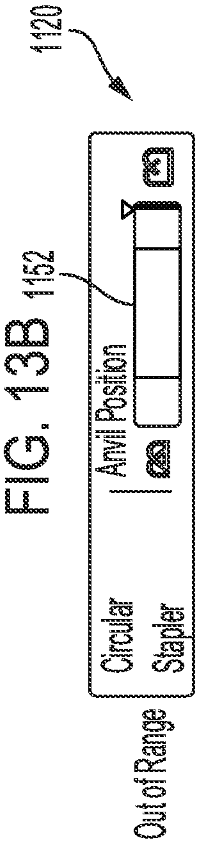
FIG. 13C illustrates a horizontally-oriented display indicating that an anvil is out of range, according to at least one aspect of the present disclosure.
Figure 13D:
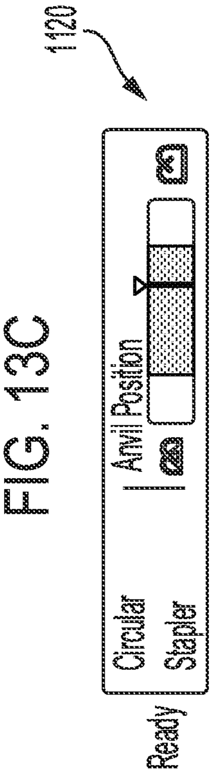
FIG. 13D illustrates the horizontally-oriented display of FIG. 13C indicating that the anvil is within range and ready to fire, according to at least one aspect of the present disclosure.

FIGS. 13C and 13D illustrate another display 1120 for providing visual feedback to a user of a circular stapler, according to at least one aspect of the present disclosure. The display 1120 is substantially the same as display 1100, except that the display 1120 includes a horizontally extending bar 1152, as opposed to a vertically extending bar 1102. The use of a horizontally extending bar 1152 utilizes more area of the display 1120 when compared to the horizontally extending bar 1102, which may make tracking the position of the indicator along the bar 1152 easier.

FIG. 13E illustrates another display 1130 for providing visual feedback to a user of a circular stapler, according to at least one aspect of the present disclosure. Display 1130 includes a vertically extending bar 1132, an indicator 1134 that visually represents a position of the anvil relative to the staple cartridge, a first feedback portion 1136 that surrounds at least a portion of the bar 1132, and a second feedback portion 1138. In one aspect, the first feedback portion 1136 displays, or illuminates, a first color, such as gray, when the anvil is within an unacceptable zone, similar to unacceptable zones 1106, 1108, for firing and displays, or illuminates, a second color, such as green, when the anvil is within the acceptable zone, similar to acceptable zone 1104, for firing. In one aspect, the second feedback portion 1138 is a visual cue, such as a checkmark or any other suitable symbol, that displays, or illuminates, a first color, such as gray, when the anvil is within one of the unacceptable zones for firing and displays, or illuminates, a second color, such as green, when the anvil is within the acceptable zone for firing. Other embodiments are envisioned where the second feedback portion 1138 is deluminated when the anvil is within the unacceptable zone for firing and illuminated when the anvil is within the acceptable zone for firing. In the embodiment shown in FIG. 13E, the control system detects that the anvil is within the acceptable zone, and thus, the control system controls the first feedback portion 1136 to illuminate the second color and the second feedback portion 1138 to illuminate the checkmark the second color.

Figure 14:
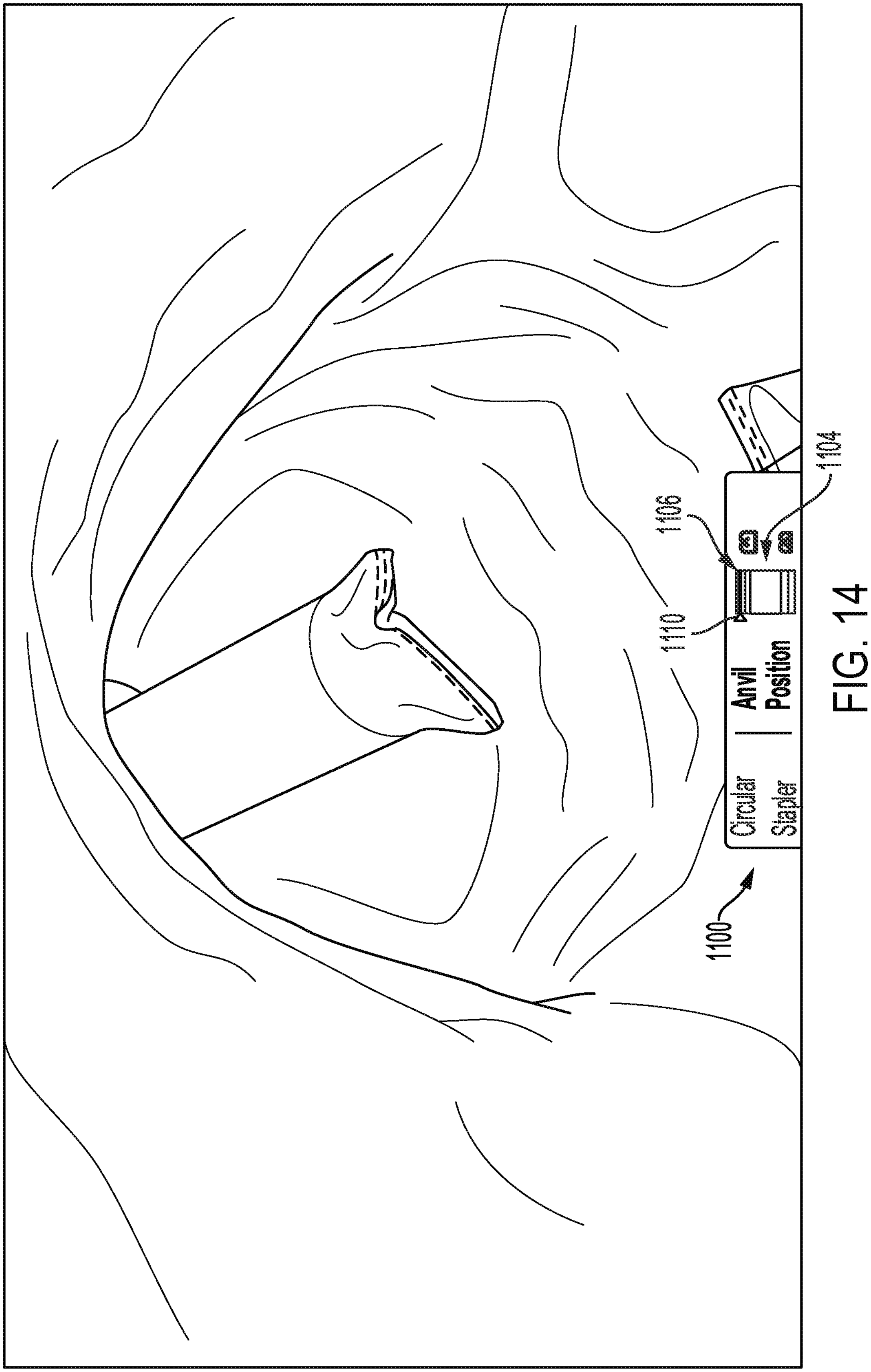
FIGS. 14 and 15 illustrate an example implementation of the display of FIGS. 13A and 13B, according to at least one aspect of the present disclosure.
Figure 15:
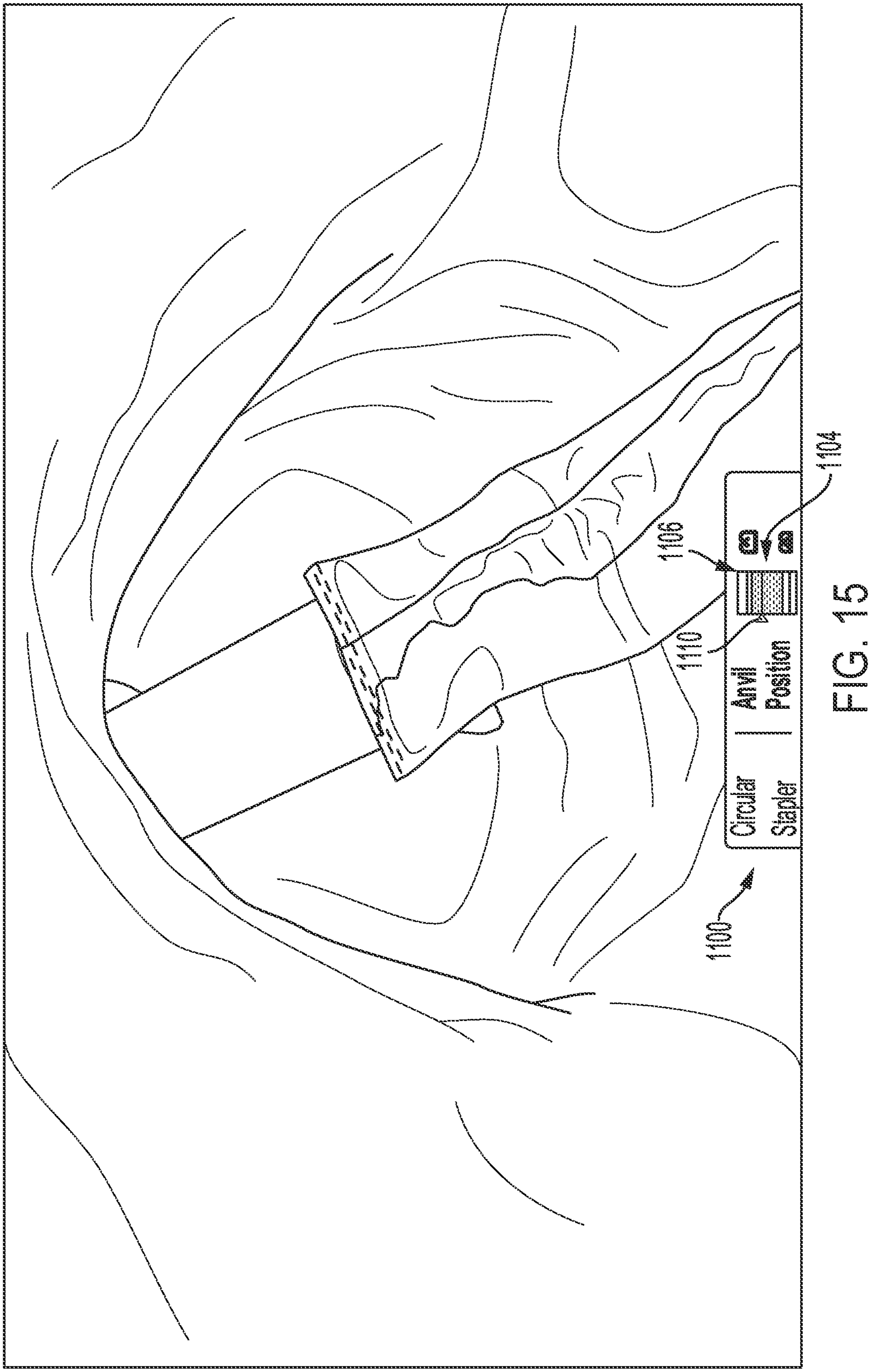
Figures 17A, 17B, 17C, 17D, 17E, 17F:
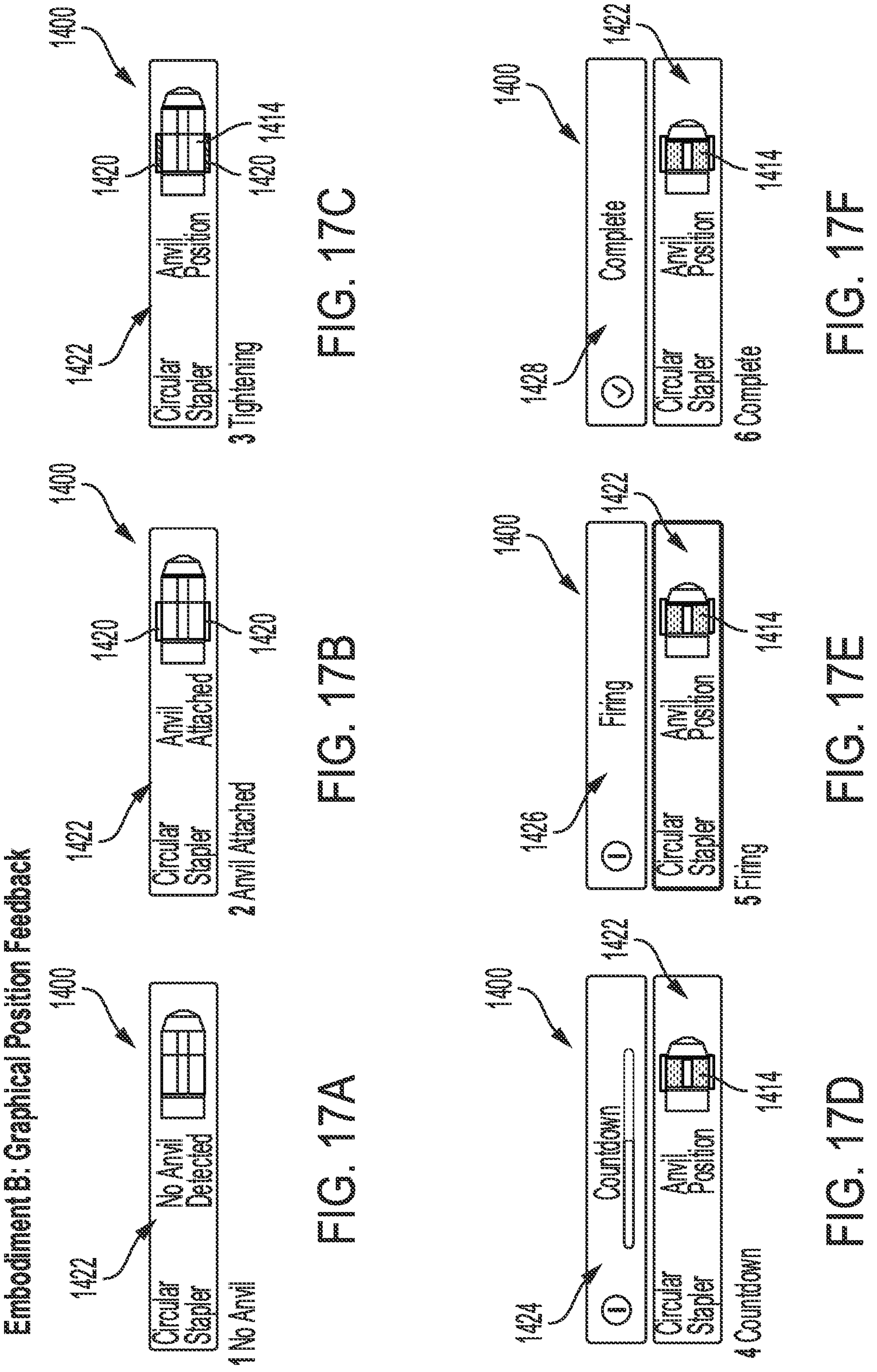
FIGS. 17A-17F illustrates various states of the display of FIGS. 16A and 16B, according to at least one aspect of the present disclosure.

FIGS. 14 and 15 illustrate an example implementation of display 1100. Display 1100 is displayed on a display, such as any number of the displays described elsewhere herein. In FIG. 14, the anvil and trocar have not yet been coupled, and thus, display 1100 defaults to show indicator 1110 within the unacceptable zone 1106. In various other embodiments, when the anvil is not coupled to the trocar, the indicator 1110 is absent from the display 1100, indicating to a user that the anvil has not yet been coupled to the trocar. In various other embodiments, when the anvil is not coupled to the trocar, the display 1100 provides any number of textual or visual feedback to indicate that the anvil isn't coupled to the trocar, such as is shown in FIG. 17A or FIG. 46A, as examples. In FIG. 15, the anvil has been coupled to the trocar and the anvil has been moved to within the acceptable firing range relative to the staple cartridge, and thus, the control system controls the indicator 1110 to point to within acceptable zone 1104 and illuminate portion 1112 green, indicating to a user that the stapler is ready to be fired.

Embodiment B: Graphical Position Feedback

Figure 16A:
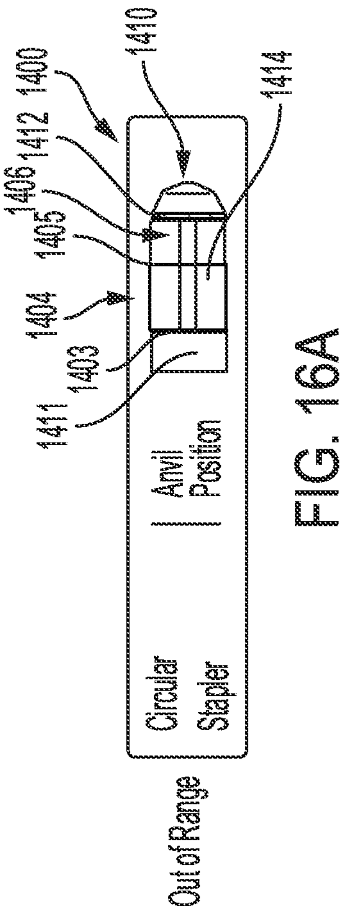
FIG. 16A illustrates a display indicating that an anvil is out of range, according to at least one aspect of the present disclosure.
Figure 16B:
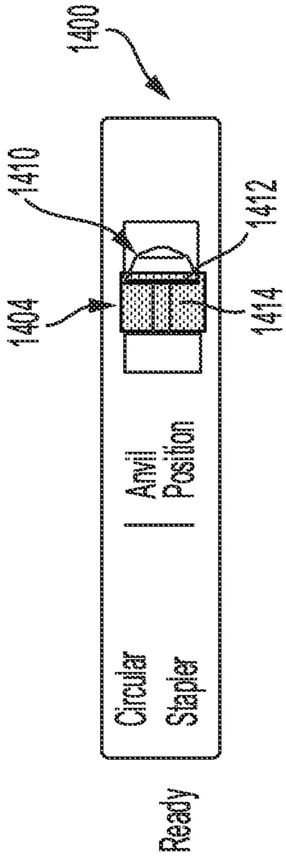
FIG. 16B illustrates the display of FIG. 16A indicating that the anvil is within range and ready to fire, according to at least one aspect of the present disclosure.

FIGS. 16A and 16B illustrate a display 1400 for providing visual feedback to a user of a circular stapler according to at least one aspect of the present disclosure. In various instances, the display 1400 is incorporated into the housing 1002 of the circular stapler 1000. In various embodiments, the display 1400 is shown on display 1030. In various other embodiments, the display 1400 is visually displayed on a display, such as display 7, display 9, display 19, within a display of the surgeon console 18, on AR device 66, or any other suitable location described herein that is configured to convey visual information to a user. In various embodiments, the display 1400 is in operable communication with a control system, such as control system 1030, that controls various aspects of the display 1400, as described herein below. In various embodiments, the control system comprises a processor and a memory storing instructions that are executable by the processor. In various embodiments, the control system is any suitable controller, control circuit, hub, or the like described herein.

The display 1400 provides visual feedback to a user indicative of the position of the anvil, such as anvil 1016, relative to the staple cartridge, such as staple cartridge 1007. In one aspect, the display 1400 is similar to display 1100. In various embodiments, the display 1400 is a graphical feedback mechanism that includes a movable indicator 1410 that is a graphical depiction of the anvil and an indicator 1411 that is a graphical depiction of the staple cartridge. In one aspect, the indicator 1410 includes an indicator line 1412 that is a graphic representation of the tissue-contacting surface of the anvil. The display 1400 also includes an acceptable zone 1404 that is defined by a threshold boundary 1403 and threshold boundary 1405, both of which are visible to the user. In one aspect, the acceptable zone 1404 corresponds to positions of the anvil relative to the staple cartridge that are suitable for firing staples from the staple cartridge. In one aspect, threshold boundary 1403 is aligned with the boundary of the indicator 1411. Other embodiments are envisioned where the threshold boundary 1403 is offset the boundary of the indicator 1411. In some embodiments, the size of the acceptable zone 1404 and the positions of the threshold boundaries 1403, 1405 are predefined, stored in a memory, and retrievable by the control system. Various other embodiments are envisioned where the size of the acceptable zone 1404 and the positions of the threshold boundaries 1403, 1405 are set by a user at a user interface.

In some embodiments, when the anvil is initially coupled to the trocar of the surgical instrument, the indicator 1410 on the display 1400 indicates that the anvil is outside acceptable zone 1404, in an unacceptable zone 1406. The control system detects the attachment of the anvil utilizing any suitable sensors, detectors, or the like, as described elsewhere herein. In various embodiments, the control system detects the attachment of the anvil utilizing an anvil connectivity sensor integrated with the anvil, such as sensor 1044. Accordingly, the control system communicates with various sensors within the anvil, such as force and/or position sensors, as examples, such that the control circuit can receive, process, and/or wirelessly transmit data from the anvil sensors to other pieces of equipment in the OR for display to users. In one aspect, the control system displays, or illuminates, the indicator line 1412 a first color, such as gray, when the anvil is not coupled to the trocar and displays, or illuminates, the indicator line 1412 a second color different than the first color, such as orange, when the anvil is coupled to the trocar. When the indicator line 1412 of indicator 1410 is within unacceptable zone 1406 (FIG. 16A), this indicates to a user that the anvil is positioned too far away from the staple cartridge, i.e., 'out of range', and that the anvil should be moved closer to the staple cartridge, such as utilizing the manually retraction knob 1013 or the motorized system. When the anvil is within the unacceptable zone 1406, the control system causes a portion 1414 of display 1400 to illuminate a first color, such as gray. In various embodiments, the size of the portion 1414 is defined by boundary lines 1403, 1405. In some embodiments, the control system prevents actuation of the firing drive to deploy the staples from the staple cartridge 1007 based on the determination of the indicator line 1412 being positioned within the unacceptable zone 1406.

When the display 1400 indicates that the anvil is within the unacceptable zone 1406, the user can utilize the retraction knob 1013 or motorized system to move the anvil toward the staple cartridge (via trocar). As the user retracts the anvil, the control system detects the movement of the anvil (using any number of position sensors or the like, described elsewhere herein) to cause the indicator 1410, and thus, indicator line 1412, to move toward indicator 1411 to visually communicate to the user that the anvil is approaching acceptable zone 1404. In various embodiments, the circular stapler includes a rotational position sensor, such as sensor 1040, that measures the rotations of the retraction knob 1013 to determine a position of the anvil relative to the staple cartridge. In various embodiments, the circular stapler includes a linear position sensor, such as sensor 1042, to measure movement of various components of the stapler, such as the trocar itself, to determine a position of the anvil relative to the staple cartridge. Once the indicator line 1412 reaches or crosses threshold boundary 1405, indicative of the anvil reaching the acceptable zone 1404 (FIG. 16B), the control system causes the portion 1414 to illuminate a second color different than the first color, such as green, indicating to a user that the anvil is within the acceptable zone 1404, and thus, the stapler is ready to be fired.

FIGS. 17A-17F illustrate various states of the display 1400 to visually communicate information to the user. The states of the display 1400 include when the anvil isn't attached to the trocar (FIG. 17A), when the anvil is initially attached to the trocar (FIG. 17B), when the anvil is moving toward the staple cartridge (FIG. 17C), when the user has reached the desired location of the anvil and a countdown is initiated to allow the tissue to relax prior to firing the staple cartridge (FIG. 17D), when the circular stapler is firing (FIG. 17E), and when firing has been completed (FIG. 17F). In one aspect, the countdown in FIG. 17D is initiated by a user by providing an input to the control system indicating that the anvil is in the desired position and that the user desires to fire the stapler. In various embodiments, the input includes actuating a button on the housing, such as housing 1002, of the circular stapler. In various embodiments, the input includes moving the safety, such as safety 1010, out of engagement with the firing trigger, such as firing trigger 1008, of the circular stapler.

In one aspect, as can be seen in FIGS. 17B and 17C, the display further 1400 includes a feedback portion 1420 defined on the upper and lower boundaries of the acceptable zone 1404. When the anvil is not moving relative to the staple cartridge (FIG. 17B), the feedback portion 1420 is illuminated a color, such as green, at a first brightness by the control system, or not luminated at all. When the anvil is moving relative to the staple cartridge (FIG. 17C), the feedback portion 1420 is illuminated the color, such as green, at a second brightness greater than the first brightness by the control system, or illuminated in the embodiments where the feedback portion 1420 wasn't illuminated when the anvil was stationary. Accordingly, feedback portion 1420 provides visual feedback regarding whether or not the anvil is moving.

In one aspect, the control system displays, or illuminates, the portion 1414 of the display 1400 a first color, such as green, with a first brightness, indicating to a user that the anvil is within the acceptable zone 1404, but is not firing (FIGS. 17D and 17F). When the stapler is firing (FIG. 17E), the control system displays, or illuminates, the portion 1414 the first color with a second brightness greater than a first brightness, indicating that the stapler is firing (FIG. 17E). In addition, the control system displays, or illuminates, the portion 1414 a second color, such as gray, when the anvil is not within the acceptable zone 1404 (FIG. 17C), or not illuminate portion 1414 at all (FIG. 17A). In some embodiments, when the stapler is not firing, the control system displays, or illuminates, a portion 1422 of the display 1400 a first color, such as gray, to indicate to a user that the stapler is not firing (FIGS. 17A-17D and 17F). When the stapler is firing (FIG. 17E), the control system displays, or illuminates, the portion 1422 a second color different than the first color, such as white, to indicate to the user that the stapler is firing. Accordingly, the portion 1422 provides another visual indicator of when the stapler is firing.

In some embodiments, as can be seen in FIG. 17A, when the anvil isn't attached to the trocar, various, or all, of the display 1400 is deluminated, indicating to a user that the anvil isn't attached to the trocar. When the anvil is coupled to the trocar (FIG. 17B), the control system displays, or illuminates, various portions of the display 1400 to visually communicate to the user that the anvil is connected to the trocar. In one aspect, when the anvil isn't coupled to the trocar, the control system displays, or illuminates, the border of the graphical representation 1410 of the anvil a first color, such as gray or does not illuminate the border of the graphical representation 1410 of the anvil at all. In one aspect, when the anvil isn't coupled to the trocar, the control system displays, or illuminates, the feedback portion 1420 a first color, such as gray or does not illuminate the feedback portion 1420 at all. In one aspect, when the anvil isn't coupled to the trocar, the control system displays, or illuminates, the indicator line 1412 a first color, such as gray or does not illuminate the indicator line 1412 at all. When the anvil is coupled to the trocar (FIG. 17B), the border of the graphical representation 1410 of the anvil is illuminated a color, such as white, the feedback portion 1420 is illuminated a color at a first brightness, as described above, and the indicator line 1412 is illuminated the first color, such as orange, as described above. Accordingly, the display 1400 provides numerous visual cues to a user of the state of the surgical stapler.

In various embodiments, the display 1400 displays notifications 1424, 1426, 1428 that provide textual information to a user. In one aspect, the control system causes display 1400 to display a notification 1424 (FIG. 17D) when the countdown has been initiated. The notification 1424 includes a bar that visually illustrates the time remaining in the countdown. In one aspect, the control system causes display 1400 to display a notification 1426 (FIG. 17E) when the stapler is firing. In one aspect, the control system causes display 1400 to display a notification 1438 (FIG. 17F) when the firing has completed.

Figure 18:
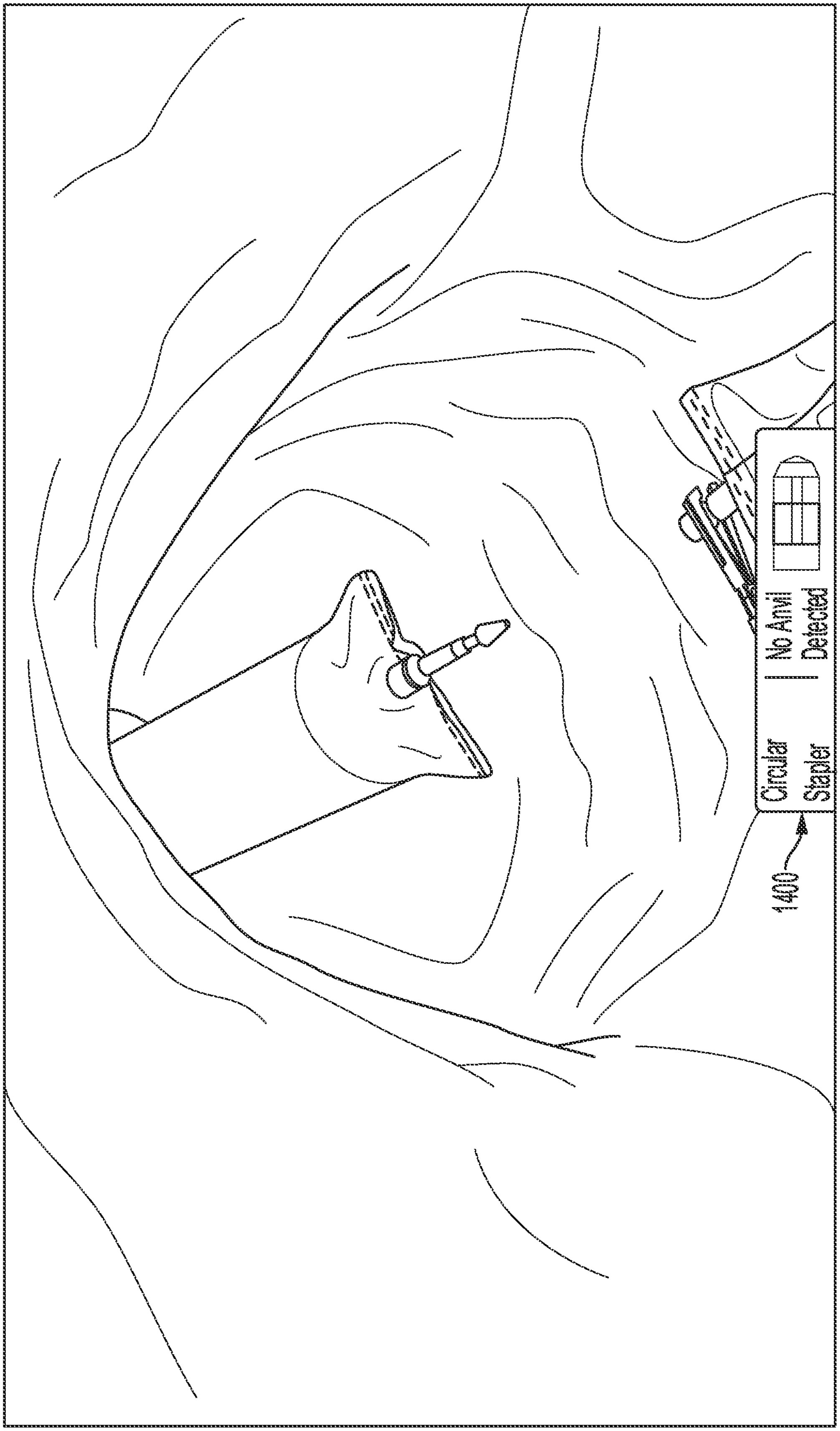
FIGS. 18-25 illustrate an example implementation of the display of FIGS. 16A and 16B, according to at least one aspect of the present disclosure.
Figure 20:
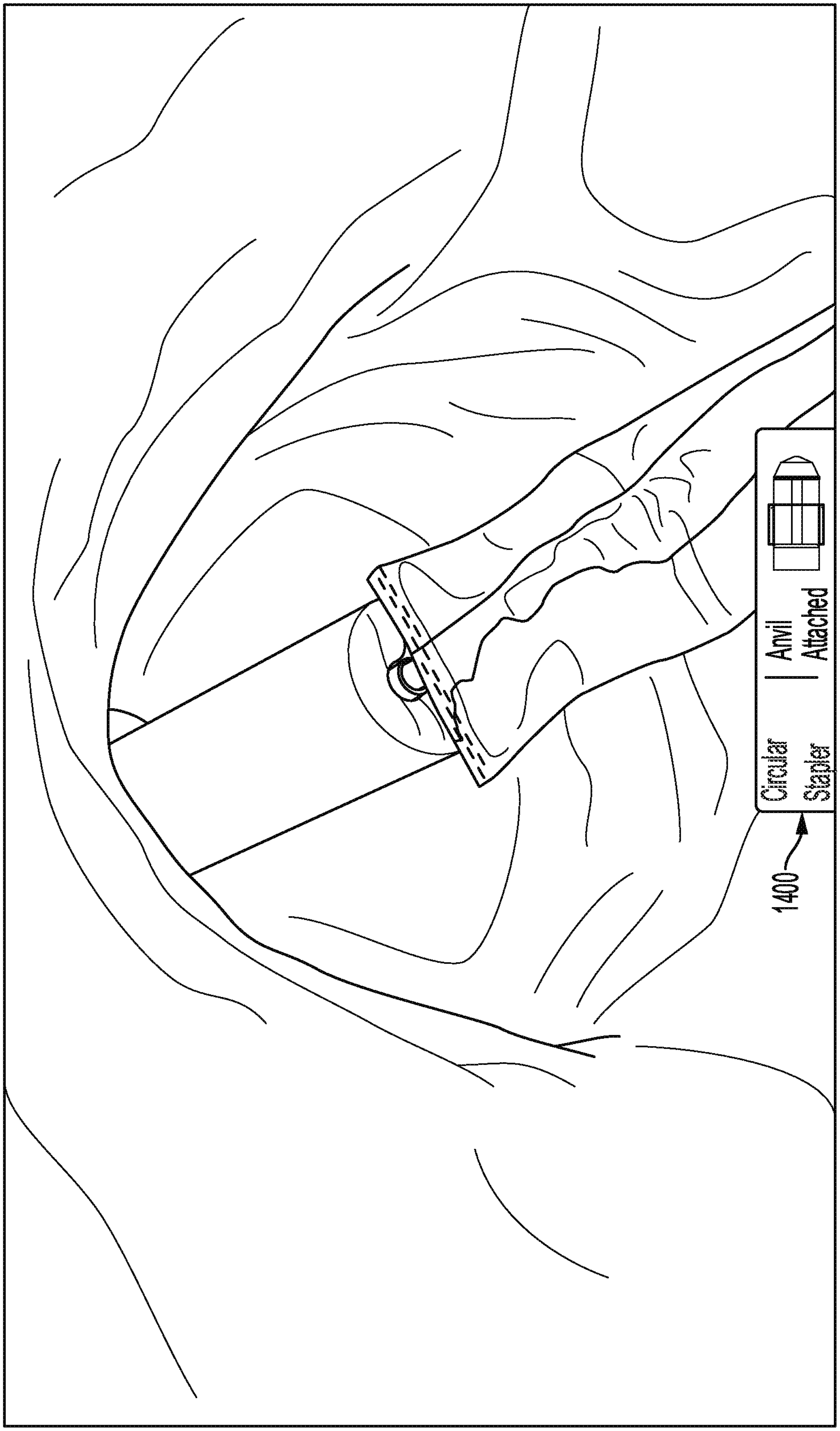
Figure 21:
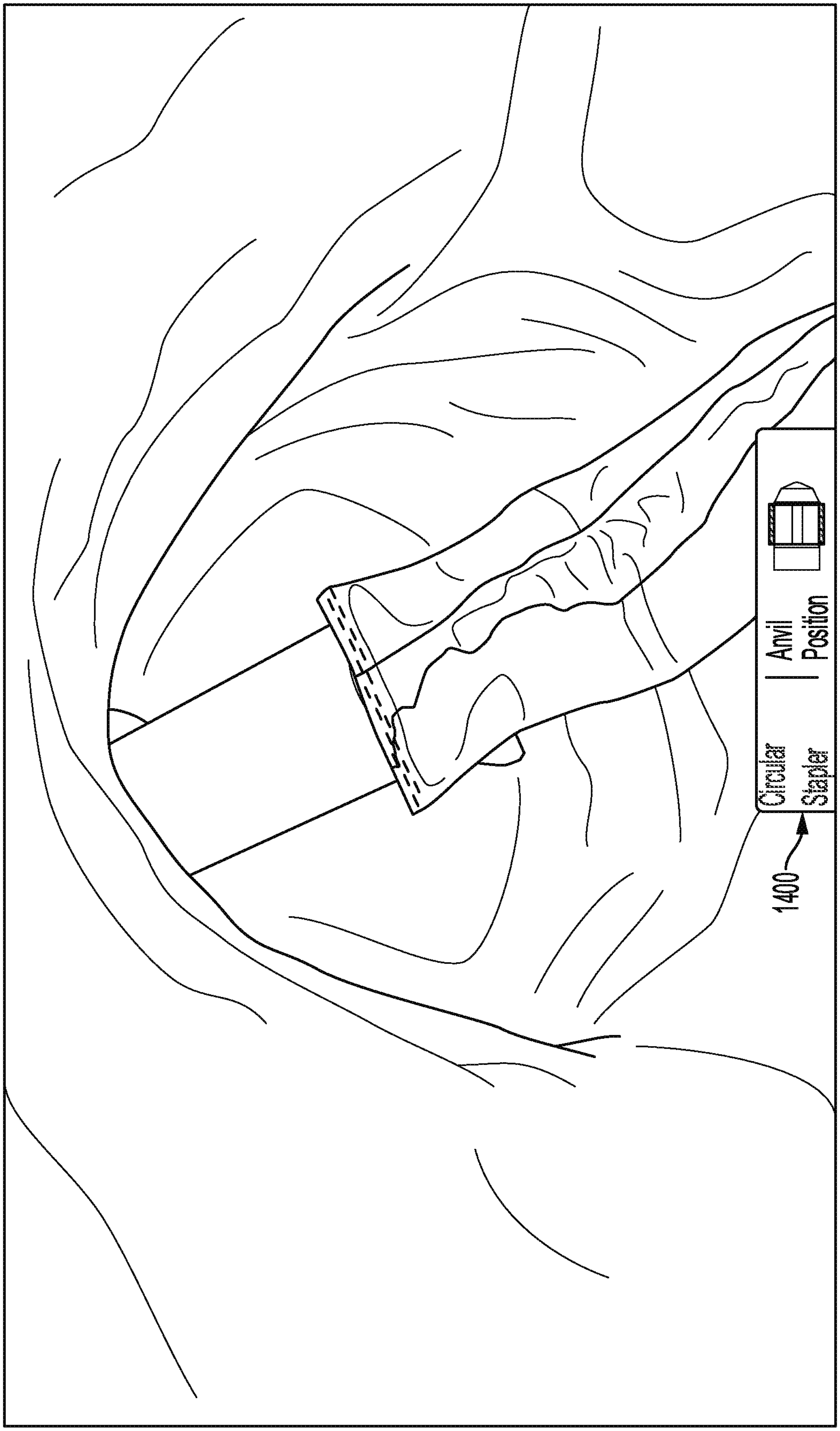
Figure 22:
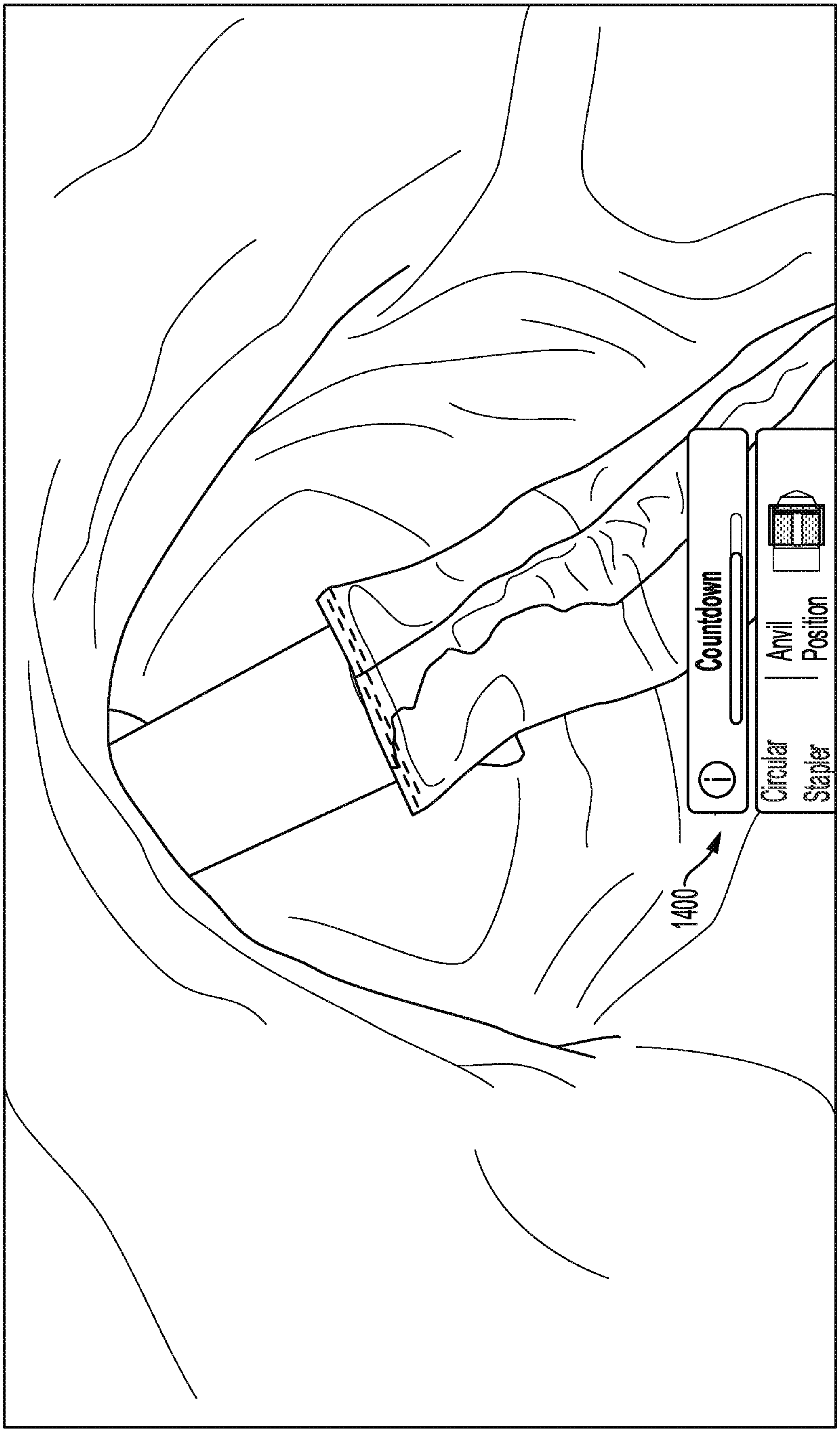
Figure 23:
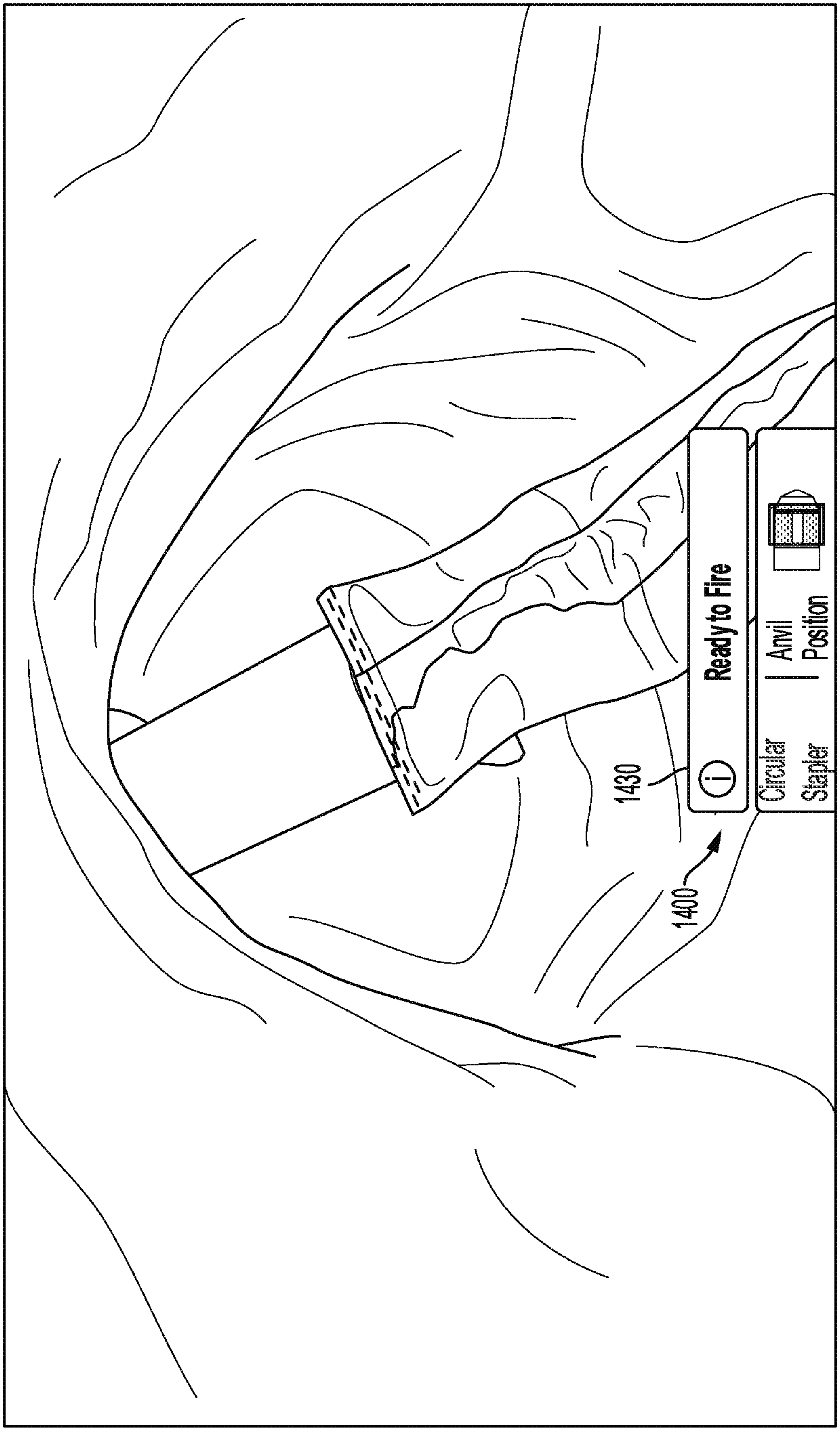
Figure 24:
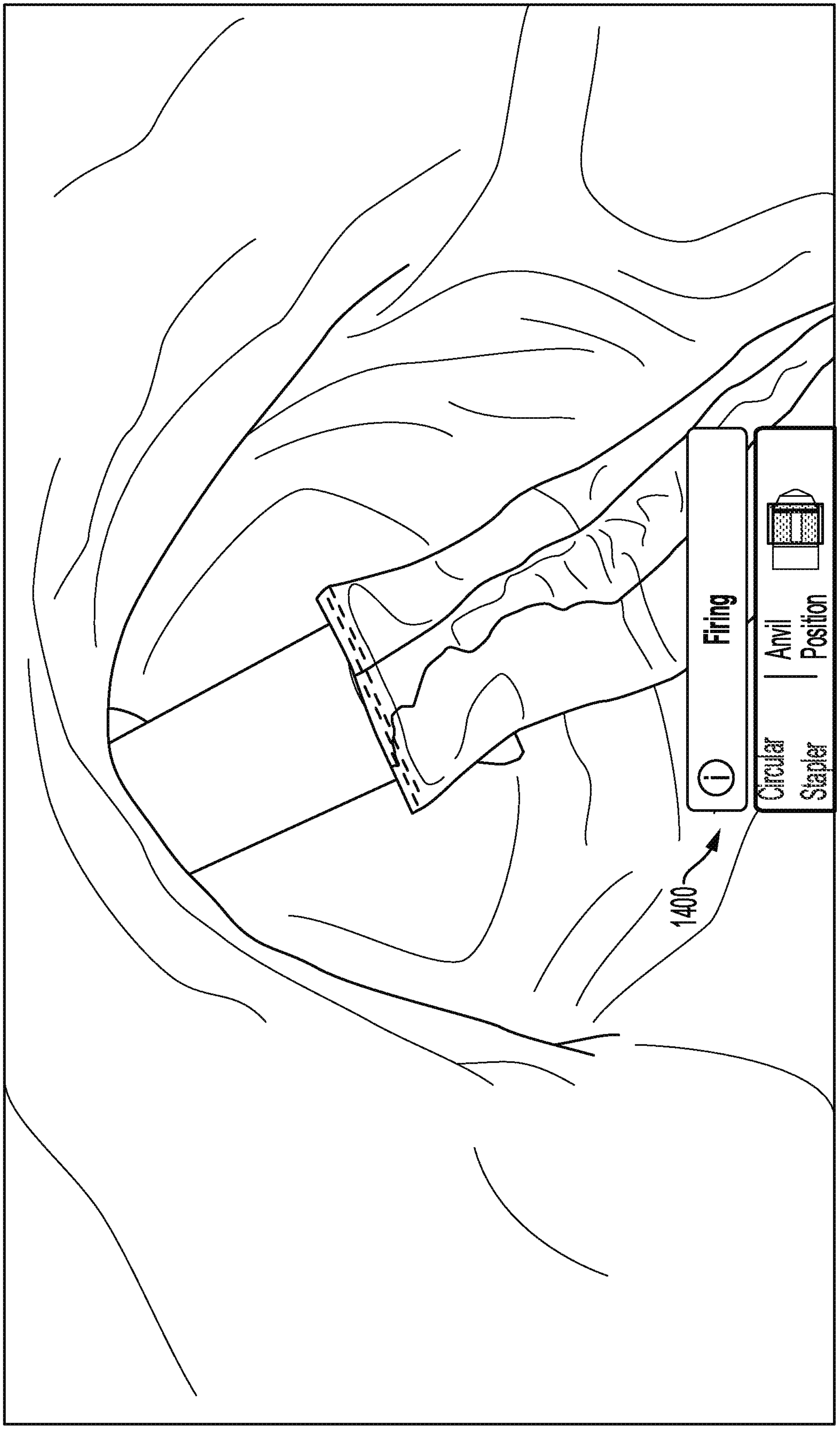
Figure 25:
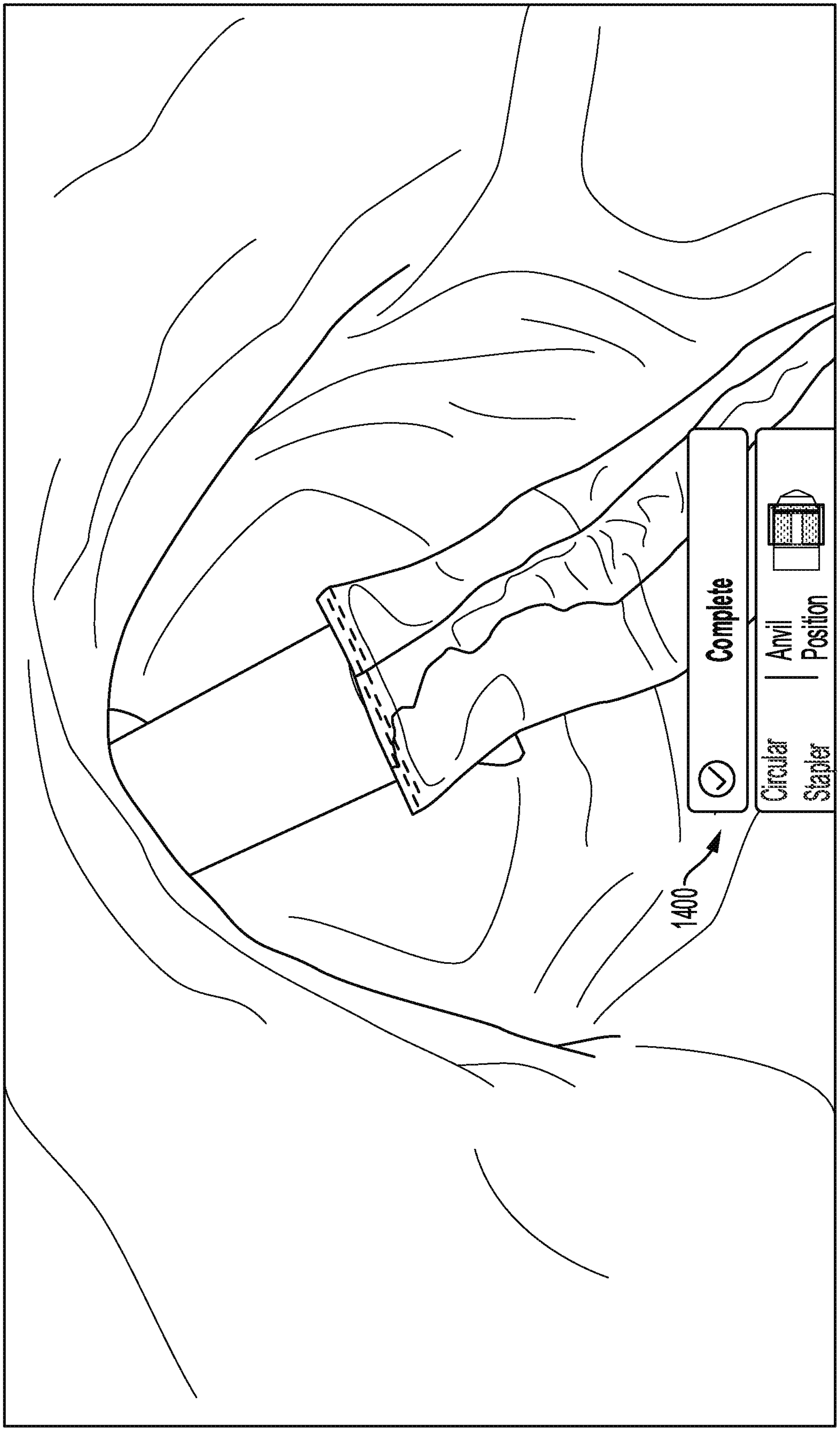

FIGS. 18-25 illustrate an example implementation of the display 1400. Display 1400 is displayed on a display, such as any number of the displays described elsewhere herein. FIG. 18 illustrates the anvil not yet coupled to the trocar, and thus, the display 1400 displays the state of FIG. 17A. FIG. 19 illustrates grasping tool moving the anvil toward trocar, but not yet coupled to the trocar, and thus, the display 1400 displays the state of FIG. 17A. FIG. 20 illustrates the anvil coupled to the trocar, and thus, the display 1400 displays the state of FIG. 17B. FIG. 21 illustrates the anvil having moved to within the acceptable zone 1404. FIG. 22 illustrates the anvil having reached the desired position and a countdown initiated to allow the tissue to relax before firing, and thus, the display 1400 displays the state of FIG. 17D. FIG. 23 illustrates the stapler being in a ready to fire state after the conclusion of the countdown. As can be seen in FIG. 23, the control system causes display 1400 to display notification 1430, indicating that the device is ready to be fired. FIG. 24 illustrates the stapler being fired, and thus, the display 1400 displays the state of FIG. 17E. FIG. 25 illustrates the stapler having completed firing, and thus, the display 1400 displays the state of FIG. 17F.

Embodiment C: Numerical Gap and Force Feedback

Figure 26A:
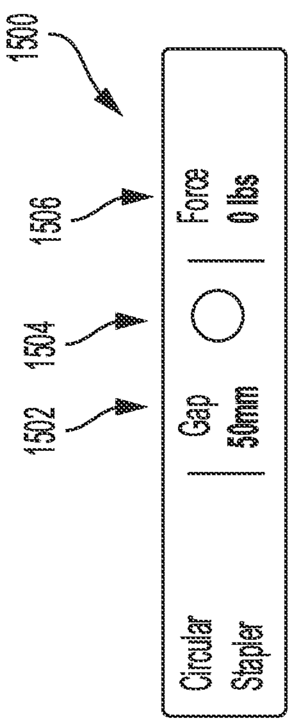
FIG. 26A illustrates a display indicating an unacceptable staple gap and no force applied to tissue, according to at least one aspect of the present disclosure.
Figure 26B:
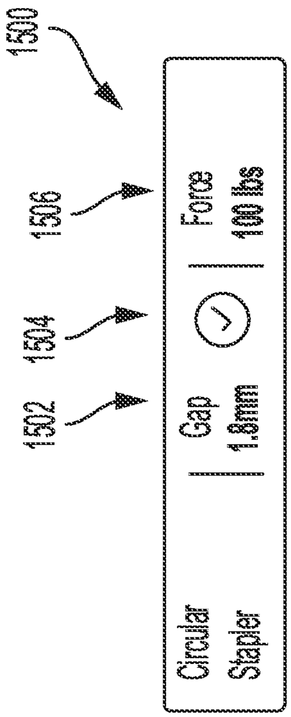
FIG. 26B illustrates the display of FIG. 26A indicating an acceptable staple gap and an amount of force applied to the tissue, according to at least one aspect of the present disclosure.

FIGS. 26A and 26B illustrate a display 1500 for providing visual feedback to a user of a circular stapler, according to at least one aspect of the present disclosure. In various embodiments, the display 1500 is incorporated into the housing 1002 of the circular stapler 1000. In various embodiments, the display 1500 is shown on display 1030. In various other embodiments, the display 1500 is visually displayed on a display, such as display 7, display 9, display 19, within a display of the surgeon console 18, on AR device 66, or any other suitable location described herein that is configured to convey visual information to a user. In various embodiments, the display 1500 is in operable communication with a control system, such as control system 1030, that controls various aspects of the display 1500, as described herein below. In various embodiments, the control system comprises a processor and a memory storing instructions that are executable by the processor. In various embodiments, the control system is any suitable controller, control circuit, hub, or the like described herein.

In one aspect, the display 1500 includes a first feedback portion 1502, a second feedback portion 1504, and a third feedback portion 1506. In one aspect, the first feedback portion 1502 numerically provides a gap distance between the anvil and the staple cartridge. In various embodiments, the gap distance is determined in any suitable manner known in the art, such as with a position sensor, a Hall-effect sensor, an encoder incorporated into the manual adjustment knob 1013, an optical feedback sensor, or any other suitable sensor described elsewhere herein. In various embodiments, the circular stapler includes a rotational position sensor, such as sensor 1040, that measures the rotations of the retraction knob 1013 to determine a position of the anvil relative to the staple cartridge. In various embodiments, the circular stapler includes a linear position sensor, such as sensor 1042, to measure movement of various components of the stapler, such as the trocar itself, to determine a position of the anvil relative to the staple cartridge.

In one aspect, the second feedback portion 1504 is a visual indicator of whether the anvil is within an acceptable zone for firing. In one aspect, the second feedback portion 1504 can be in a first state (FIG. 26A) where the second feedback portion 1504 depicts a circle filled with a first color, such as grey, or a second state (FIG. 26B) where the second feedback portion 1504 depicts a symbol, such as a checkmark, and/or a second color different than the first color, such as green, indicating that the anvil is within an acceptable zone for firing the surgical stapler. In various instances, the second feedback portion 1504 depicts the first state when the anvil is within an unacceptable zone, indicating to a user that the anvil is not in a suitable position for firing the stapler. In some embodiments, the control system prevents actuation of the firing drive to deploy the staples from the staple cartridge 1007 based on the determination of the second feedback portion 1504 being in the first state.

In one aspect, the third feedback portion 1506 is a numerical representation of the amount of force that the anvil is applying to the tissue positioned between the anvil and the staple cartridge. In various embodiments, the force is determined in any suitable manner known in the art, such as with a force sensor, a strain gauge, or any other suitable sensors, as described elsewhere herein. In various embodiments, a torque sensor is integrated with the rotation knob 1013 of the circular stapler to measure the torque a user applies. In various embodiment, a force sensor is integrated with the internal shaft of the stapler that drives the trocar, or within the trocar itself, for measuring the force the shaft experiences. In various embodiments, the anvil includes a force sensor for measuring the force applied to the tissue. In one aspect, the control system communicates with the anvil utilizing an anvil connectivity sensor integrated with the anvil, such as sensor 1044 such that the control system can interrogate and receive data from the force sensor.

Figure 27A:
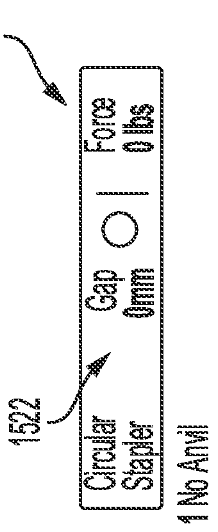
FIGS. 27A-27F illustrate various states of the display of FIGS. 26A and 26B, according to at least one aspect of the present disclosure.
Figure 27B:
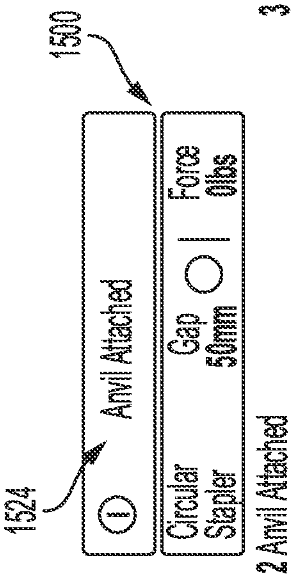
Figure 27C:
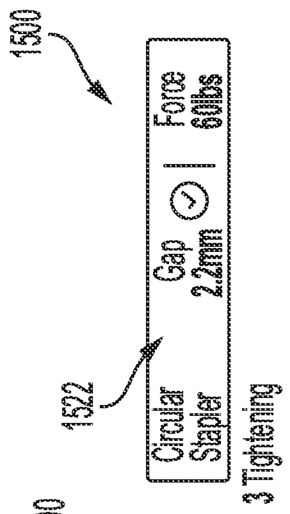
Figure 27D:
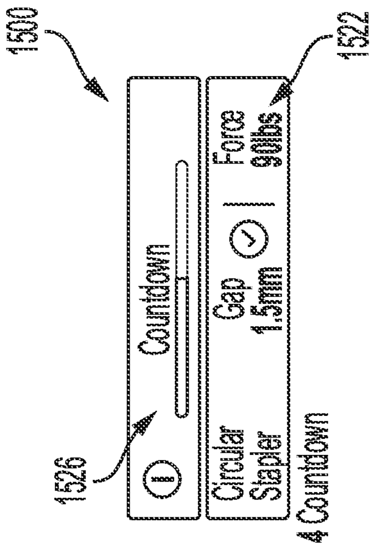
Figure 27E:
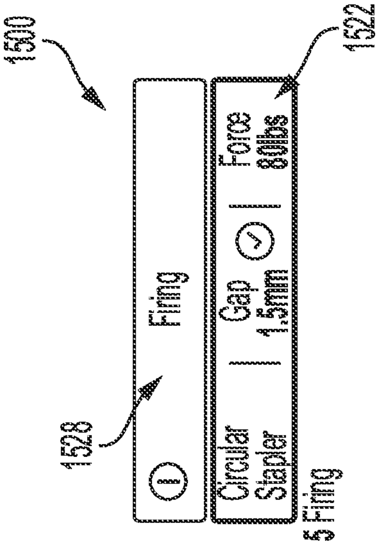
Figure 27F:
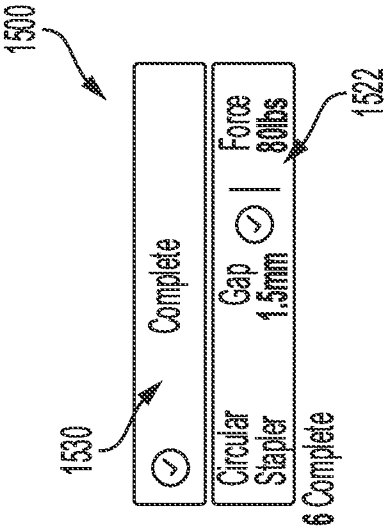

FIG. 27A-27F illustrate various states of the display 1500 to visually communicate information to the user. The states of the display 1500 include when the anvil isn't attached to the trocar (FIG. 27A), when the anvil is attached to the trocar (FIG. 27B), when the anvil is within an acceptable zone for firing the stapler, as indicated by second feedback portion 1504 (FIG. 27C), when the user has reached the desired location of the anvil and a countdown is initiated to allow the tissue to relax prior to firing the staple cartridge (FIG. 27D), when the circular stapler is firing (FIG. 27E), and when firing has been completed (FIG. 27F).

In one aspect, when the stapler is not firing, the control system causes a portion 1522 of the display 1500 to illuminate a first color, such as gray, to indicate to a user that the stapler is not firing (FIGS. 27A-27D and 27F), or not illuminate the portion 1522 at all. When the stapler is firing (FIG. 27E), the control system causes the portion 1522 to illuminate a second color, such as white, to indicate to the user that the stapler is firing.

In various embodiments, the display 1500 displays notifications 1524, 1526, 1528, 1530 that provide textual information to a user. In one aspect, the control system causes display 1500 to display a notification 1524 (FIG. 27B) that the anvil has been attached. In various embodiments, the control system detects that the anvil has been attached to the trocar using sensors described elsewhere herein. In one aspect, the control system causes the display 1500 to display a notification 1526 (FIG. 27D) when the countdown has been initiated. The notification 1526 also includes a bar that visually illustrates the time remaining in the countdown. In one aspect, the control system causes the display 1500 to display a notification 1528 (FIG. 27E) when the stapler is firing. In one aspect, the control system causes the display 1500 to display a notification 1530 (FIG. 27F) when the firing has completed.

Figure 28:
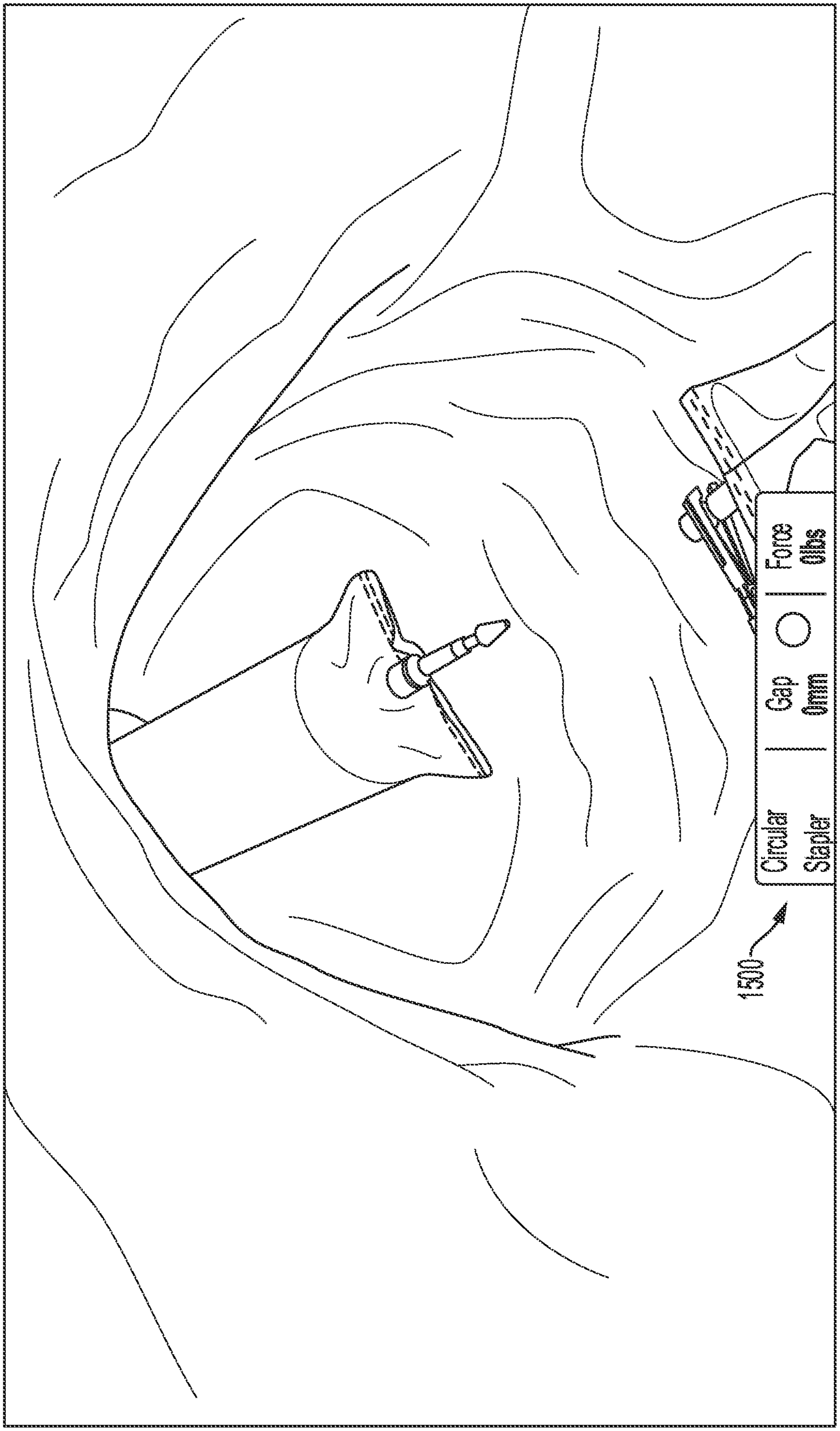
FIGS. 28-36 illustrate an example implementation of the display of FIG. 26, according to at least one aspect of the present disclosure.
Figure 29:
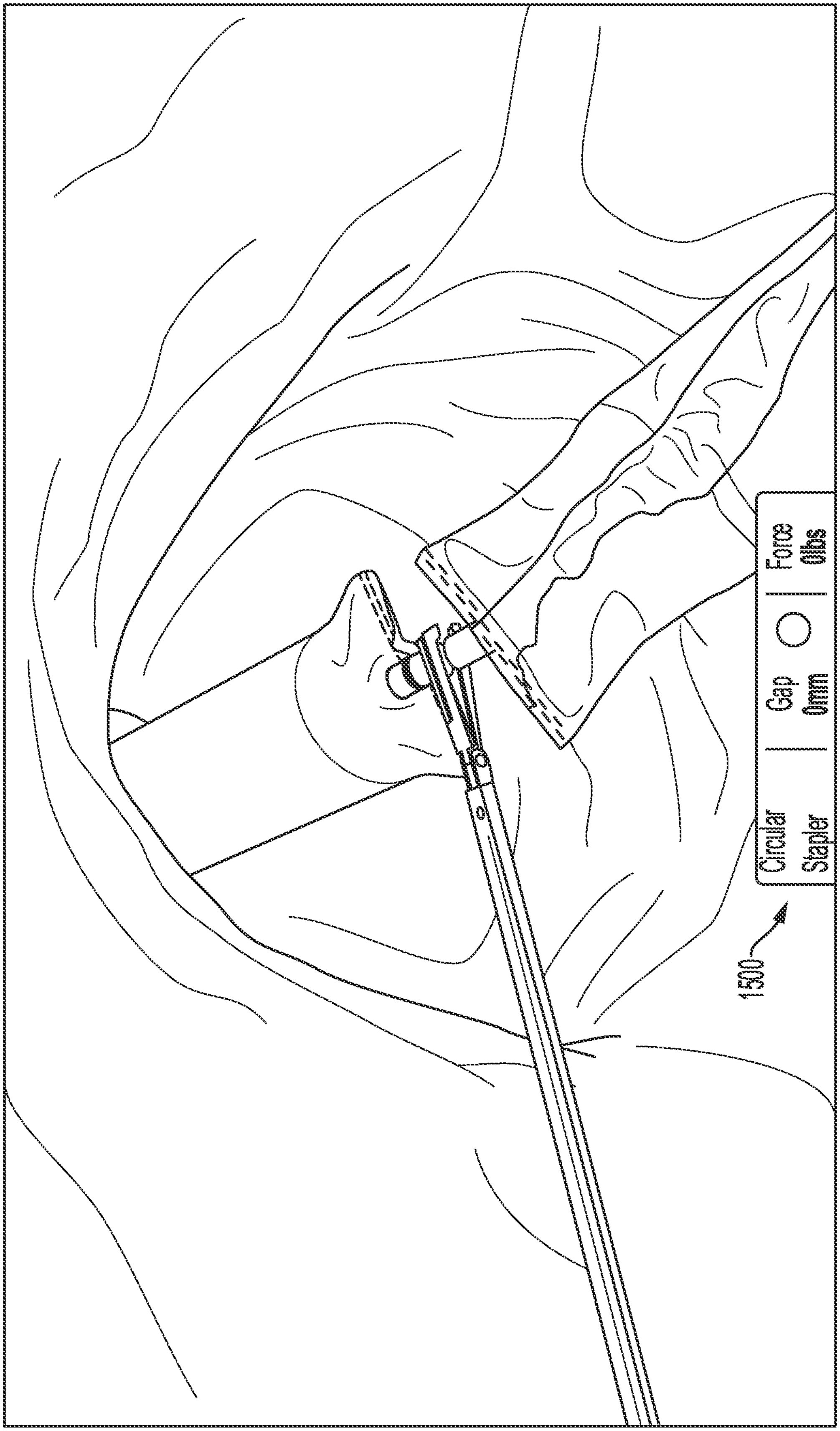
Figure 30:
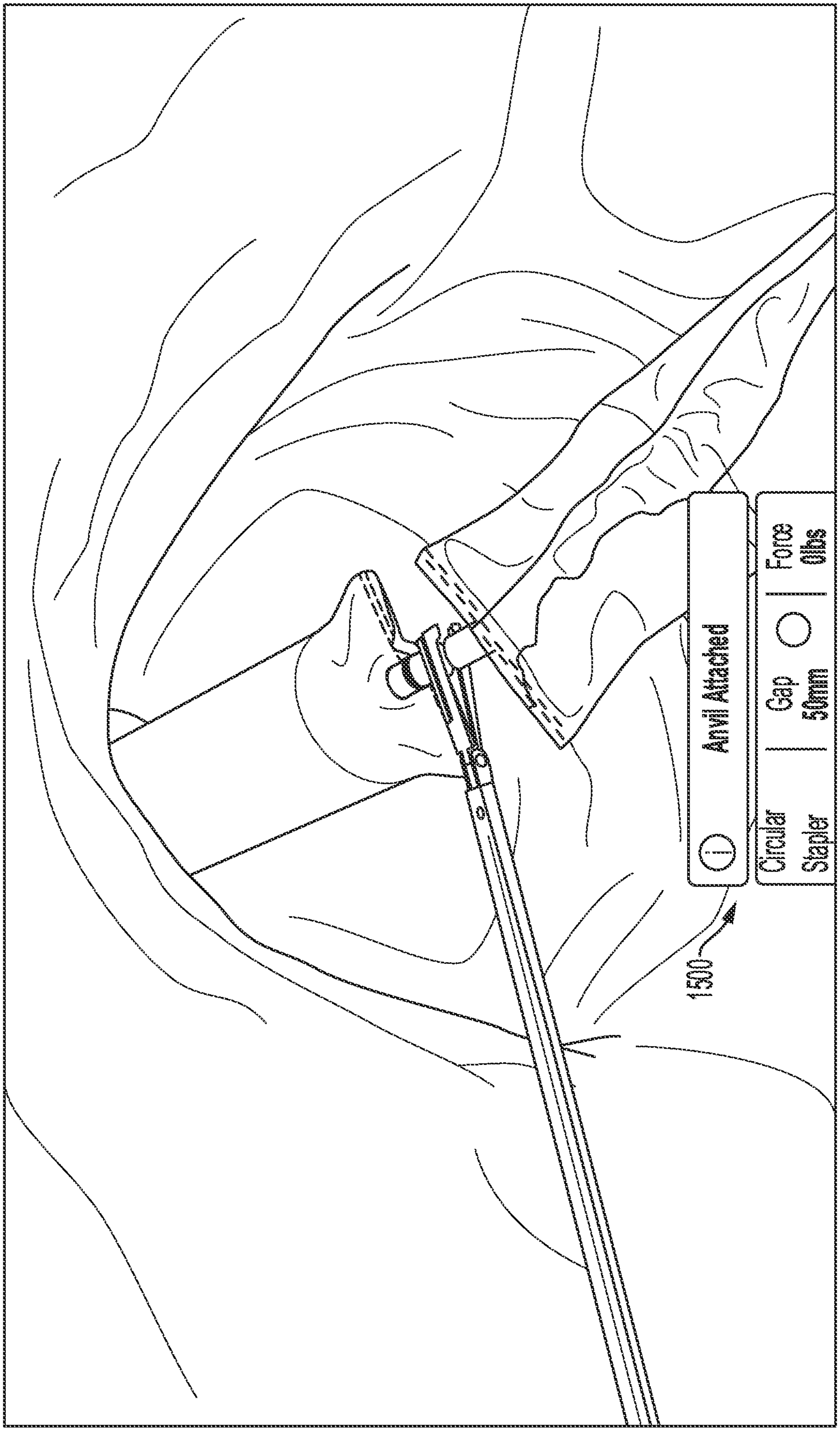
Figure 31:
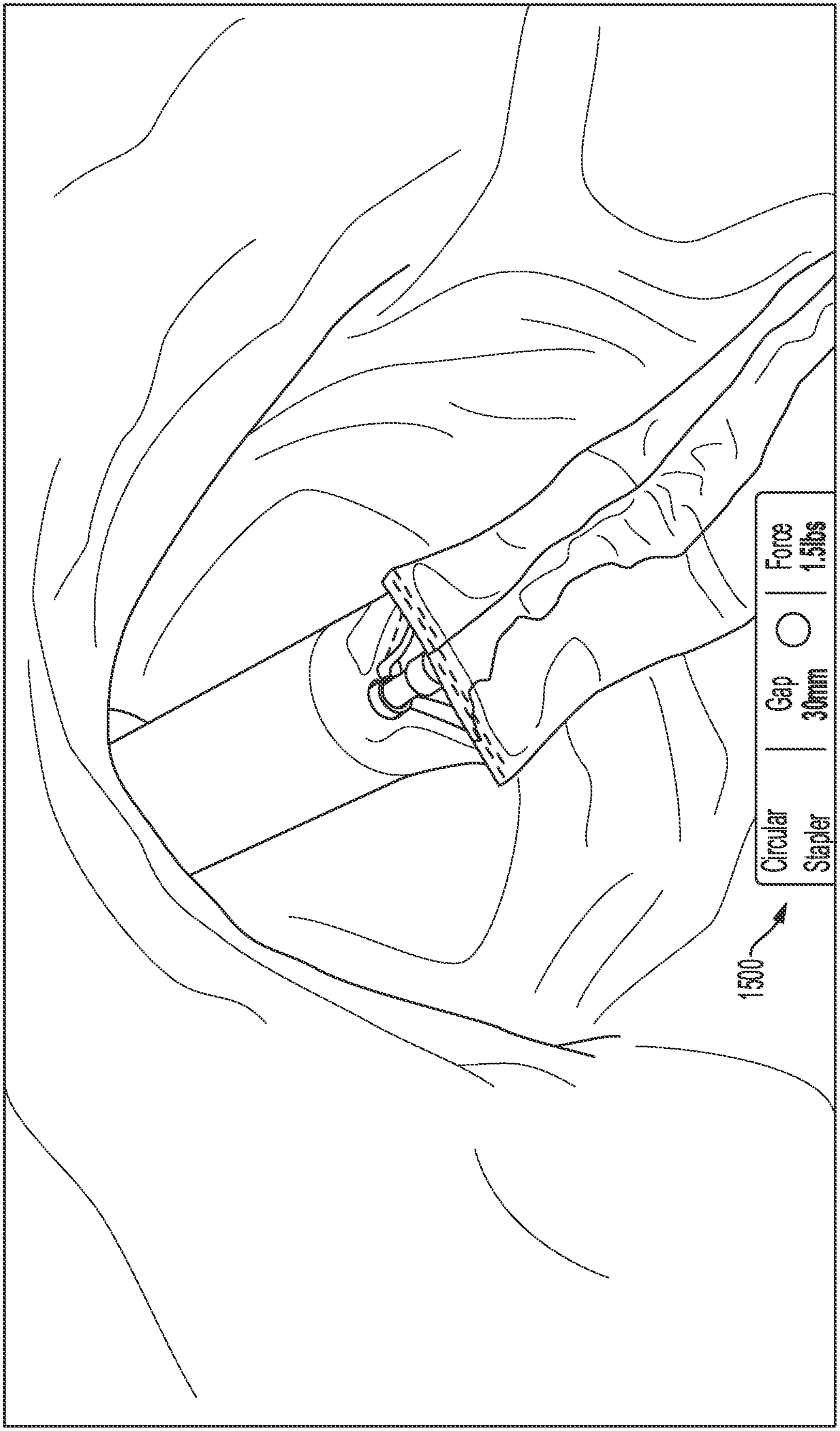
Figure 32:
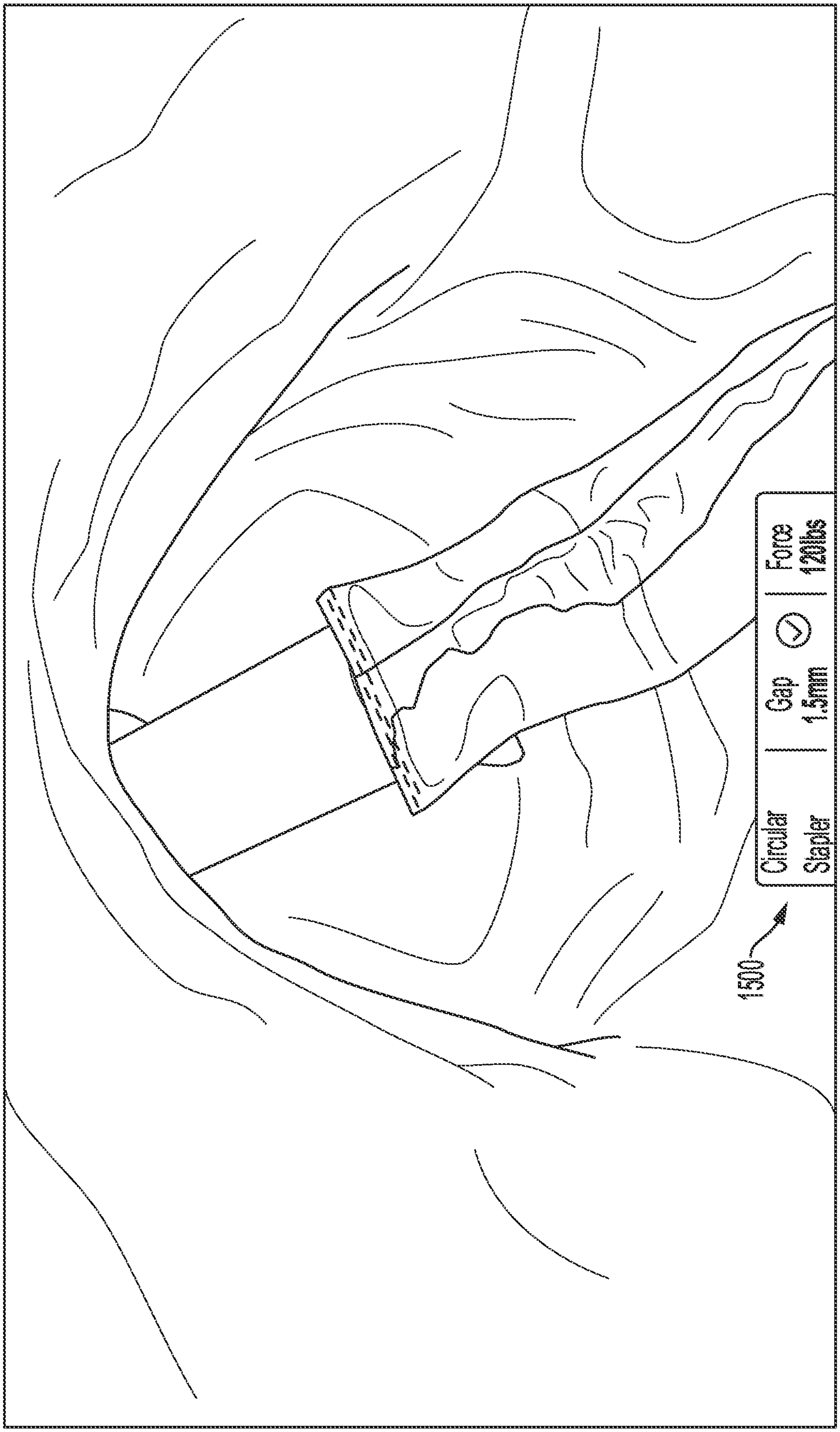
Figure 33:
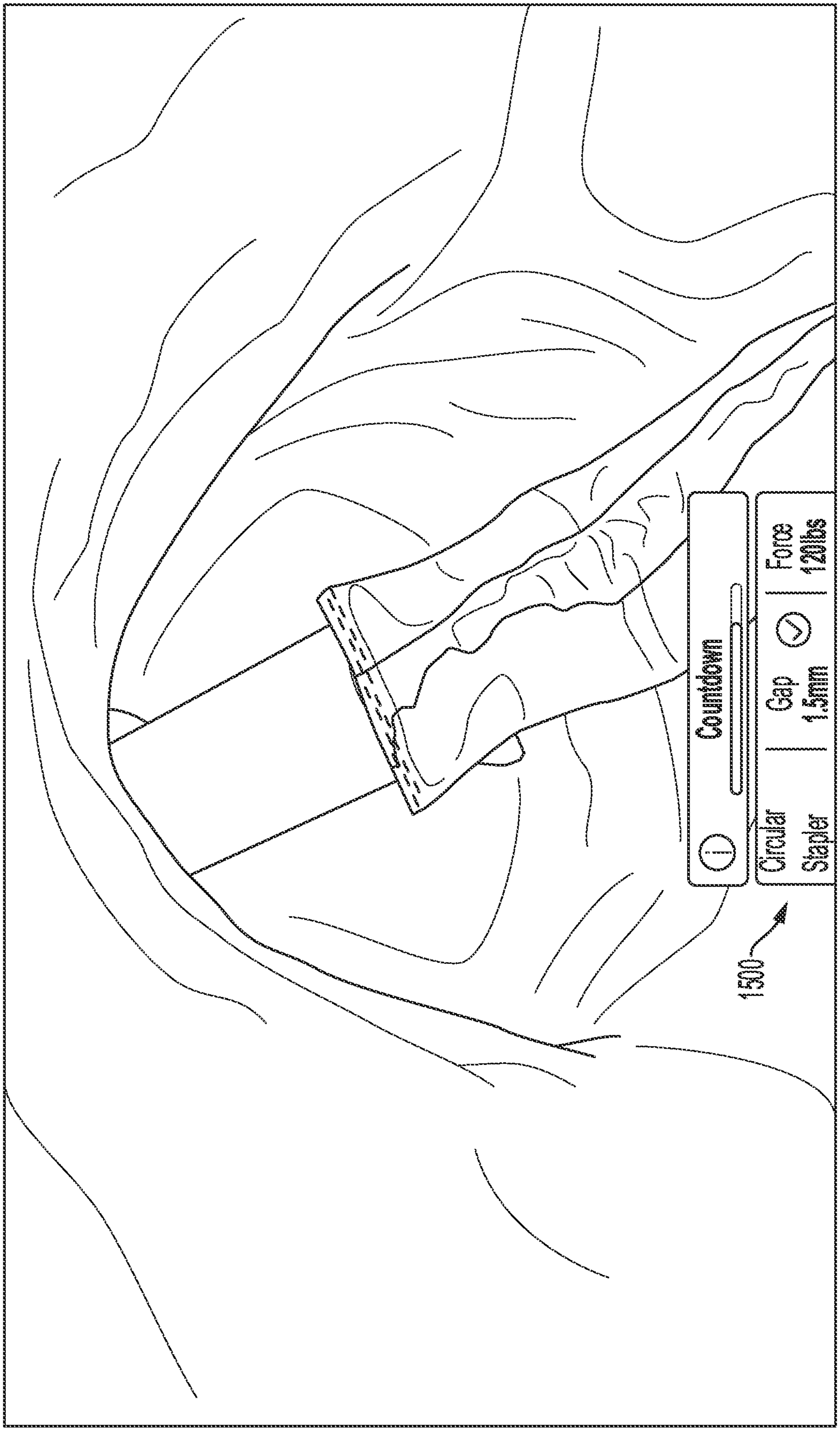
Figure 34:
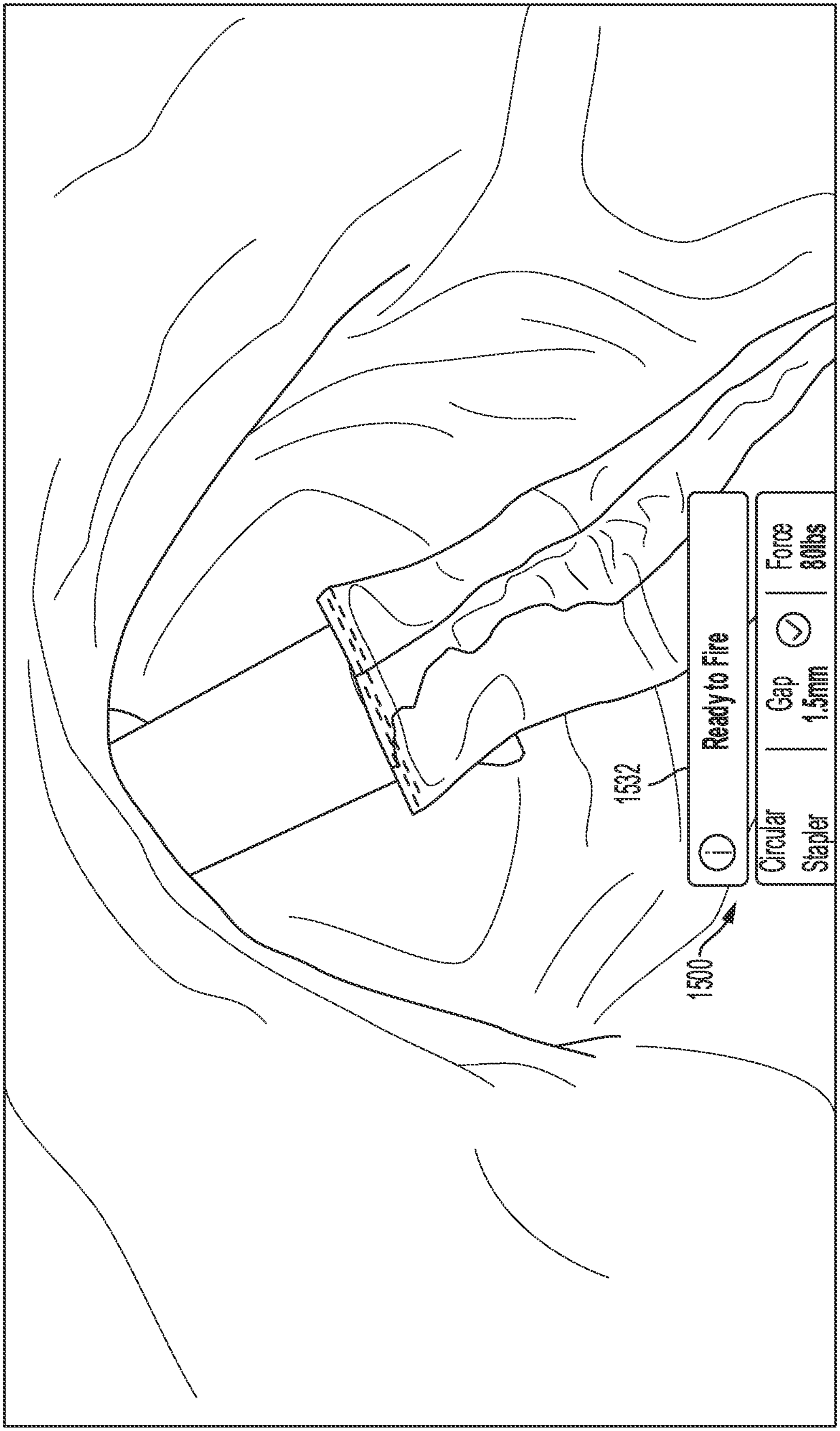
Figure 35:
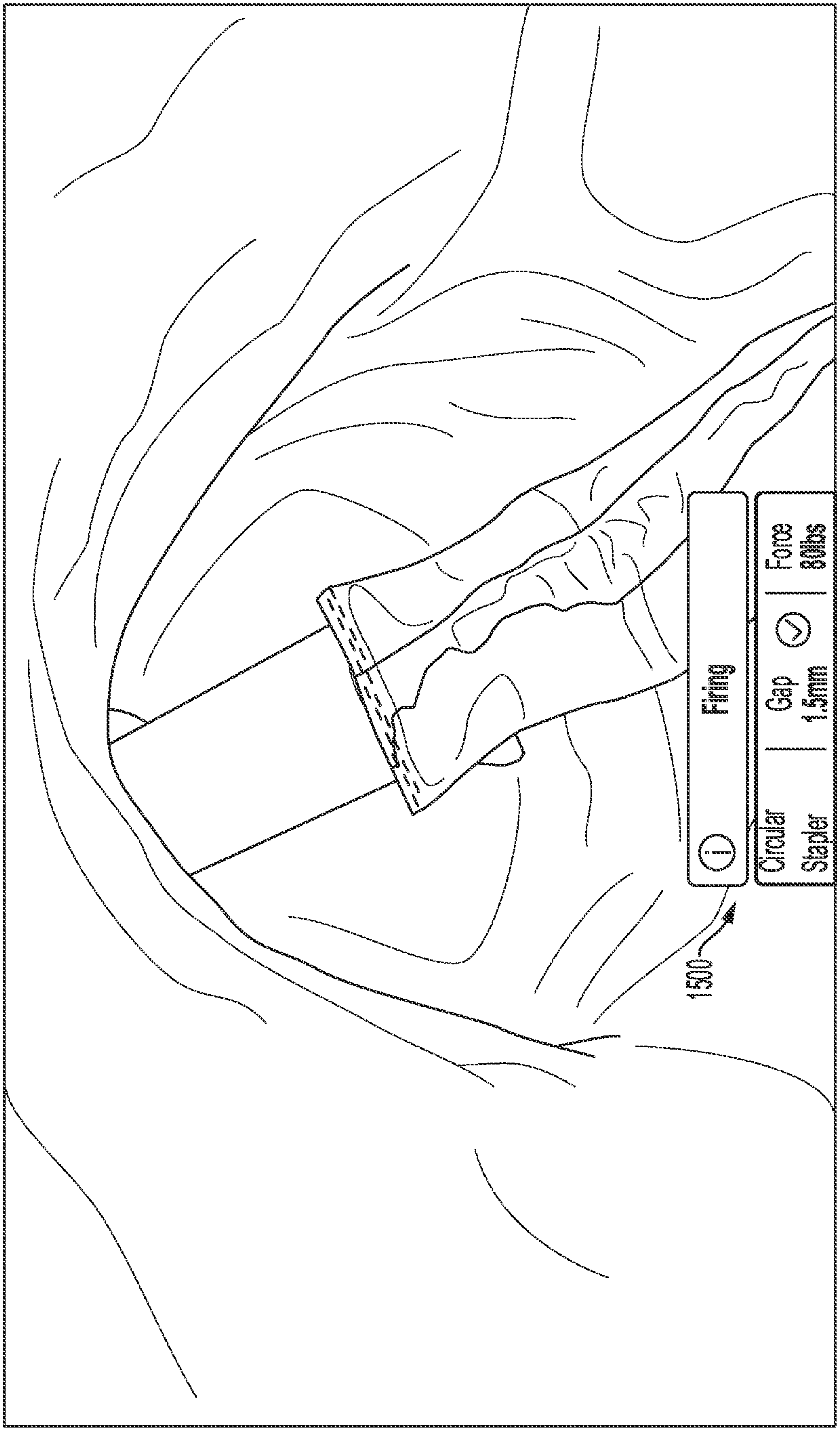
Figure 36:
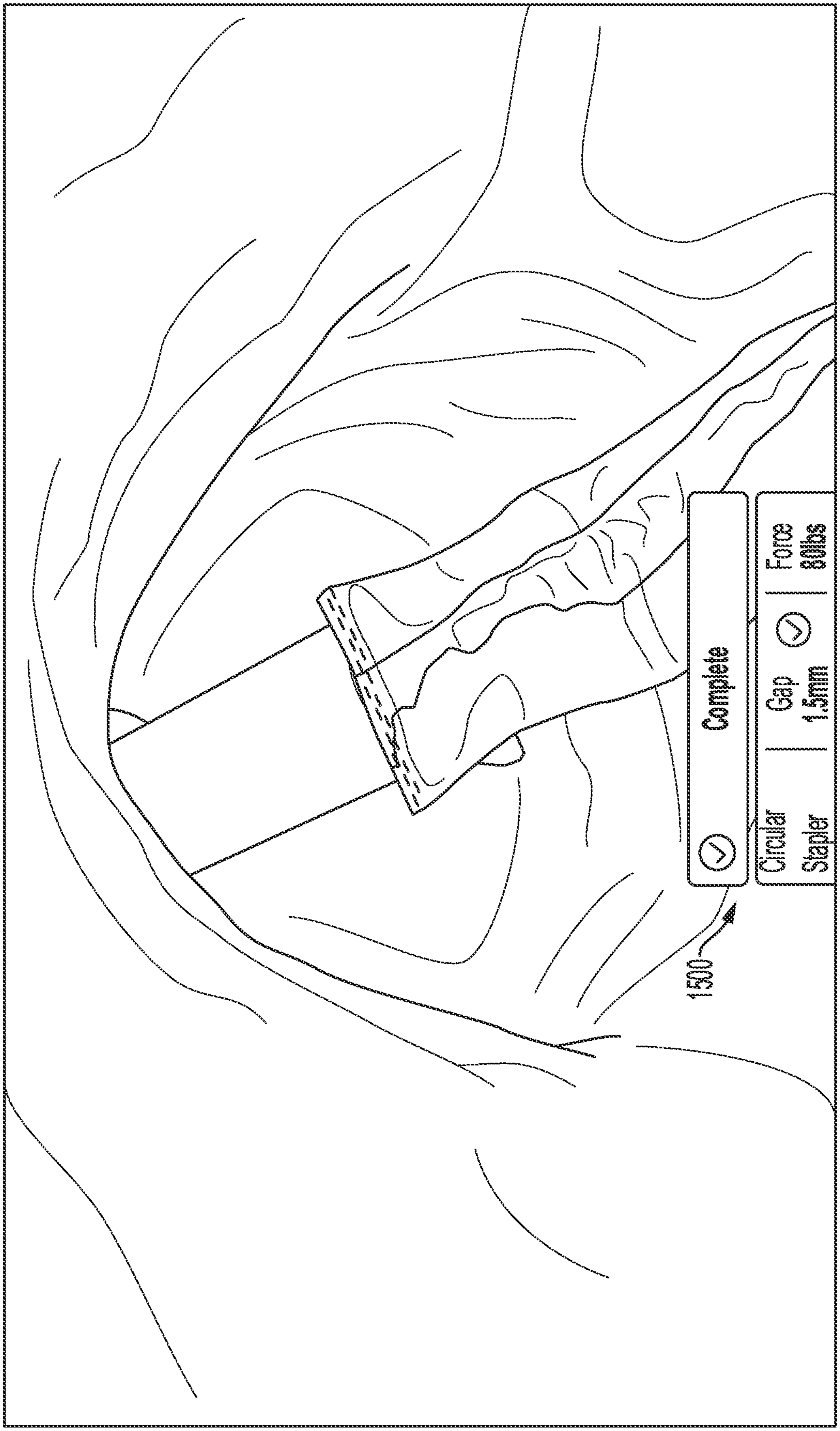

FIGS. 28-36 illustrate an example implementation of the display 1500. Display 1500 is displayed on a display, such as any number of the displays described elsewhere herein. FIG. 28 illustrates the anvil not yet coupled to the trocar, and thus, the display 1500 displays the state of FIG. 27A. FIG. 29 illustrates a grasping tool moving the anvil toward trocar, but not yet coupled to the trocar, and thus, the display 1500 displays the state of FIG. 27A. FIG. 30 illustrates the anvil coupled to the trocar, and thus, the display 1500 displays the state of FIG. 27B. FIG. 31 illustrates the anvil moving relative to the staple cartridge, but not yet within an acceptable zone, as indicated by the second feedback portion 1504. FIG. 32 illustrates the anvil having reached the acceptable zone for firing, as indicated by the second feedback portion 1504, and thus, the display 1500 displays the state of FIG. 27C. FIG. 33 illustrates the anvil having reached the desired position and a countdown initiated to allow the tissue to relax before firing, and thus, the display 1500 displays the state of FIG. 27D. FIG. 34 illustrates the stapler being in a ready to fire state. As can be seen in FIG. 34, the control system causes display 1500 to display notification 1532, indicating that the device is ready to be fired. FIG. 35 illustrates the stapler being fired, and thus, the display 1500 displays the state of FIG. 27E. FIG. 36 illustrates the stapler having completed firing, and thus, the display 1500 displays the state of FIG. 27F.

Embodiment D: Graphic Gap and Force Feedback

Figure 37A:
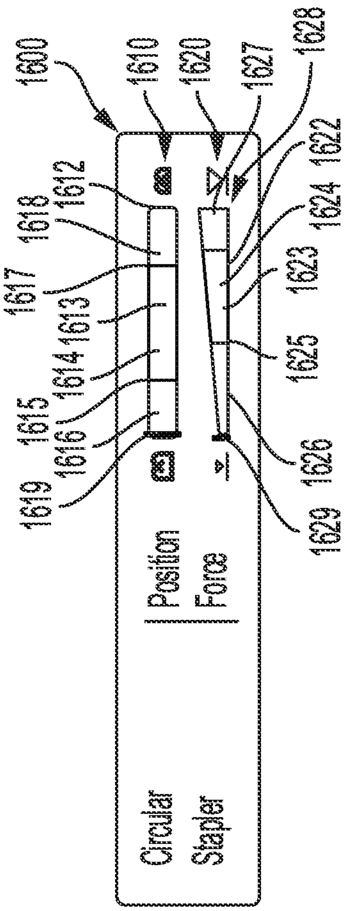
FIG. 37A illustrates a display indicating that an anvil is out of range and that an unacceptable amount of force is being applied to tissue by the anvil, according to at least one aspect of the present disclosure.
Figure 37B:
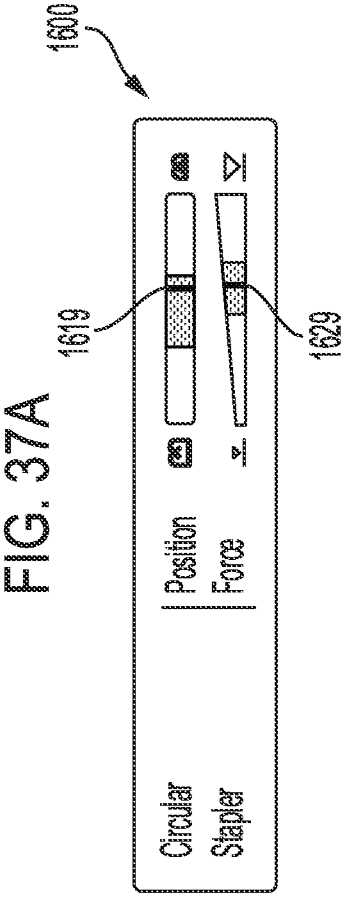
FIG. 37B illustrates the display of FIG. 37A indicating that the anvil is within range and that an acceptable amount of force is being applied to tissue by the anvil, according to at least one aspect of the present disclosure.

FIGS. 37A and 37B illustrate a display 1600 for providing visual feedback to a user of a circular stapler, according to at least one aspect of the present disclosure. In various instances, the display 1600 is incorporated into the housing 1002 of the circular stapler 1000. In various embodiments, the display 1600 is shown on display 1030. In various other embodiments, the display 1600 is visually displayed on a display, such as display 7, display 9, display 19, within a display of the surgeon console 18, on AR device 66, or any other suitable location described herein that is configured to convey visual information to a user. In various embodiments, the display 1600 is in operable communication with a control system, such as control system 1030, that controls various aspects of the display 1600, as described herein below. In various embodiments, the control system comprises a processor and a memory storing instructions that are executable by the processor. In various embodiments, the control system is any suitable controller, control circuit, hub, or the like described herein.

The display 1600 provides visual feedback to a user indicative of the position of the anvil relative to the staple cartridge and a force being applied to tissue captured by the anvil and staple cartridge. In various embodiments, the display 1600 includes a first feedback portion 1610 and a second feedback portion 1620. In one aspect, the first feedback portion 1610 provides visual feedback regarding the relative positioning between the anvil, such as anvil 1016, and the staple cartridge, such as staple cartridge 1007. The first feedback portion 1610 includes a bar 1612 that defines an acceptable zone 1614 and unacceptable zones 1616, 1618 surrounding the acceptable zone 1614. The unacceptable zone 1616 and the acceptable zone 1614 are separated by a threshold boundary 1615 that is visible to the user. Similarly, the unacceptable zone 1618 and the acceptable zone 1614 are separated by a threshold boundary 1617 that is visible to the user. In one aspect, the acceptable zone 1614 corresponds to positions of the anvil relative to the staple cartridge that are suitable for firing staples from the staple cartridge. In one aspect, the unacceptable zone 1616 corresponds to positions of the anvil that are too far, such as over a threshold limit, away from the staple cartridge, and thus, is not suitable for firing staples from the staple cartridge. In one aspect, the unacceptable zone 1618 corresponds to positions of the anvil that are too close, such as under a threshold limit, to the staple cartridge, and thus, is not suitable for firing staples from the staple cartridge. In various embodiments, the size of the zones 1614, 1616, 1618 and positions of threshold boundaries 1615, 1617 are predefined, stored in a memory, and are retrievable by the control system. Various other embodiments are envisioned where the size of the zones 1614, 1616, 1618 and the positions of threshold boundaries 1615, 1617 are set by a user at a user interface.

The first feedback portion 1610 also include an indicator 1619 that moves along bar 1612 to visually illustrate which of the zones 1614, 1616, 1618 the anvil is positioned within, as determined by the control system. As described elsewhere herein, the position of the anvil is detected by the control system using any suitable sensor or the like. In various embodiments, the circular stapler includes a rotational position sensor, such as sensor 1040, that measures the rotations of the retraction knob 1013 to determine a position of the anvil relative to the staple cartridge. In various embodiments, the circular stapler includes a linear position sensor, such as sensor 1042, to measure movement of various components of the stapler, such as the trocar itself, to determine a position of the anvil relative to the staple cartridge. With the determined position, the control system controls a position of the indicator 1619 along the bar 1612 to visually illustrate which zone 1614, 1616 1618 the anvil is within.

In some embodiments, when the anvil is initially coupled to the trocar of the surgical instrument, the control system detects the attached of the anvil and causes the indicator 1619 on the first feedback portion 1610 to point to a position on the bar 1612 to indicate that the anvil is within unacceptable zone 1616, as shown in FIG. 37A. In various embodiments, the control system detects the attachment of the anvil utilizing any suitable sensors, detectors, or the like, as described elsewhere herein. In various embodiments, the control system detects the attachment of the anvil utilizing an anvil connectivity sensor integrated with the anvil, such as sensor 1044. Accordingly, the control system can communicate with various sensors within the anvil, such as force and/or position sensors, as examples, such that the control circuit can receive, process, and/or wirelessly transmit data from the anvil sensors to other pieces of equipment in the OR for display to users. The indicator 1619 being positioned within the unacceptable zone 1616 indicates to a user that the anvil is positioned too far away from the staple cartridge, i.e., 'out of range', and that the anvil should be moved closer to the staple cartridge, such as utilizing the manually retraction knob 1013 on the housing or the motorized system. When the anvil is within one of unacceptable zones 1616, 1618, the control system displays, or illuminates, a portion 1613 of the bar 1612 a first color, such as gray, to indicate that the stapler is not ready for firing. In various other embodiments, when the anvil is within one of unacceptable zones 1616, 1618, the portion 1613 of the bar 1612 is deluminated to indicate that the stapler is not ready for firing. In some instances, the size of the portion 1613 is defined by boundaries 1615, 1617. In some embodiments, the control system prevents actuation of the firing drive to deploy the staples from the staple cartridge 1007 based on the determination of the indicator 1619 being positioned within one of the unacceptable zones 1616, 1618.

When the control system indicates that the anvil is within the unacceptable zone 1616 using indicator 1619, the user can utilize the retraction knob 1013 or motorized system to move the anvil toward the staple cartridge (via trocar). As the user retracts the anvil, the control system detects the movement of the anvil to cause the indicator 1619 to move along bar 1612 to visually communicate to the user that the anvil is approaching acceptable zone 1614. Once the indicator 1619 has reached the acceptable zone 1614 (FIG. 37B), the control system displays, or illuminates, the portion 1613 of the bar 1612 a second color different than the first color, such as green, indicating to a user that the anvil is within the acceptable zone 1614, and thus, the stapler can be fired.

As referenced above, the display 1600 also includes a second feedback portion 1620. In one aspect, the second feedback portion 1620 provides visual feedback regarding the amount of force applied to the tissue positioned between the anvil and the staple cartridge. The second feedback portion 1620 includes a bar 1622 that defines an acceptable zone 1624 and unacceptable zones 1626, 1628 surrounding the acceptable zone 1624. The unacceptable zone 1626 and the acceptable zone 1624 are separated by a threshold boundary 1625 that is visible to the user. Similarly, the unacceptable zone 1628 and the acceptable zone 1624 are separated by a threshold boundary 1627 that is visible to the user. In one aspect, the acceptable zone 1624 corresponds to forces that are suitable for firing staples from the staple cartridge. In one aspect, the unacceptable zone 1626 corresponds to forces that are too low, such as under a threshold limit, and thus, is unacceptable for firing staples. For instance, the anvil may not be applying a sufficient force to the tissue to enable to staples to properly form and seal the tissue. In one aspect, the unacceptable zone 1628 corresponds to forces that are too high, such as over a threshold limit, and thus, is unacceptable for firing staples. For instance, the anvil may be applying too much force to the tissue and thus, may damage the tissue.

In various embodiments, the size of the zones 1624, 1626, 1628 and the positions of threshold boundaries 1625, 1627 are predefined, stored in a memory, and are be retrievable by the control system. Various other embodiments are envisioned where the size of the zones 1624, 1626, 1628 and the positions of threshold boundaries 1625, 1627 are set by a user at a user interface.

The second feedback portion 1620 also includes an indicator 1629 that moves along bar 1622 to visually illustrate how much force is being applied to the staples via zones 1624, 1626, 1628. As described elsewhere herein, the force being applied to the tissue is detected by the control system using any suitable sensor, such as with a force sensor, a strain gauge, or any other suitable means of sensing the force, as described elsewhere herein. In various embodiments, a torque sensor is integrated with the rotation knob 1013 of the circular stapler to measure the torque a user applies. In various embodiment, a force sensor is integrated with the internal shaft of the stapler that drives the trocar, or within the trocar itself, for measuring the force the shaft experiences. In various embodiments, the anvil includes a force sensor for measuring the force applied to the tissue. In one aspect, the control system communicates with the anvil utilizing an anvil connectivity sensor integrated with the anvil, such as sensor 1044 such that the control system can interrogate and receive data from the force sensor. With the determined force, the control system controls a position of the indicator 1629 to visually illustrate which force zone 1624, 1626 1628 to position the indicator 1629 within.

In some embodiments, when the anvil is initially coupled to the trocar of the surgical instrument, the control system detects that the anvil is not yet applying a force to the tissue, and thus, causes the indicator 1629 on the second feedback portion 1620 to point to the unacceptable zone 1616, as shown in FIG. 37A. The indicator 1629 pointing to the unacceptable zone 1626 indicates to a user that the anvil should be moved closer to the staple cartridge to apply additional force to the tissue, such as utilizing the manually retraction knob 1013 on the housing or the motorized system. When the anvil is within one of unacceptable zones 1626, 1628, a portion 1623 of the bar 1622 displays, or illuminates, a first color, such as gray, to indicate that the stapler is not ready for firing. In some instances, the size of the portion 1623 is defined by the boundaries 1625, 1627. In some embodiments, the control system prevents actuation of the firing drive to deploy the staples from the staple cartridge 1007 based on the determination of the indicator 1629 being positioned within one of the unacceptable zones 1626, 1628.

When the second feedback portion 1620 indicates that too little force is being applied to the tissue, by way of indicator 1629 being positioned within unacceptable zone 1626, the user can utilize the retraction knob 1013 to move the anvil toward the staple cartridge (via trocar) to apply additional force to the tissue. As the user retracts the anvil, the control system detects the increase in force (using any number of force sensors or the like, described elsewhere herein) to cause the indicator 1629 to move along bar 1622 to visually communicate to the user that the force applied to the tissue is approaching acceptable zone 1624. Once the indicator 1629 has reached the acceptable zone 1624 (FIG. 37B), the portion 1623 of the bar 1622 displays, or illuminates, a second color different than the first color, such as green, indicating to a user that a sufficient amount of force is being applied to the tissue, and thus, the stapler can be fired.

Figures 38A, 38B, 38C, 38D, 38E, 38F:
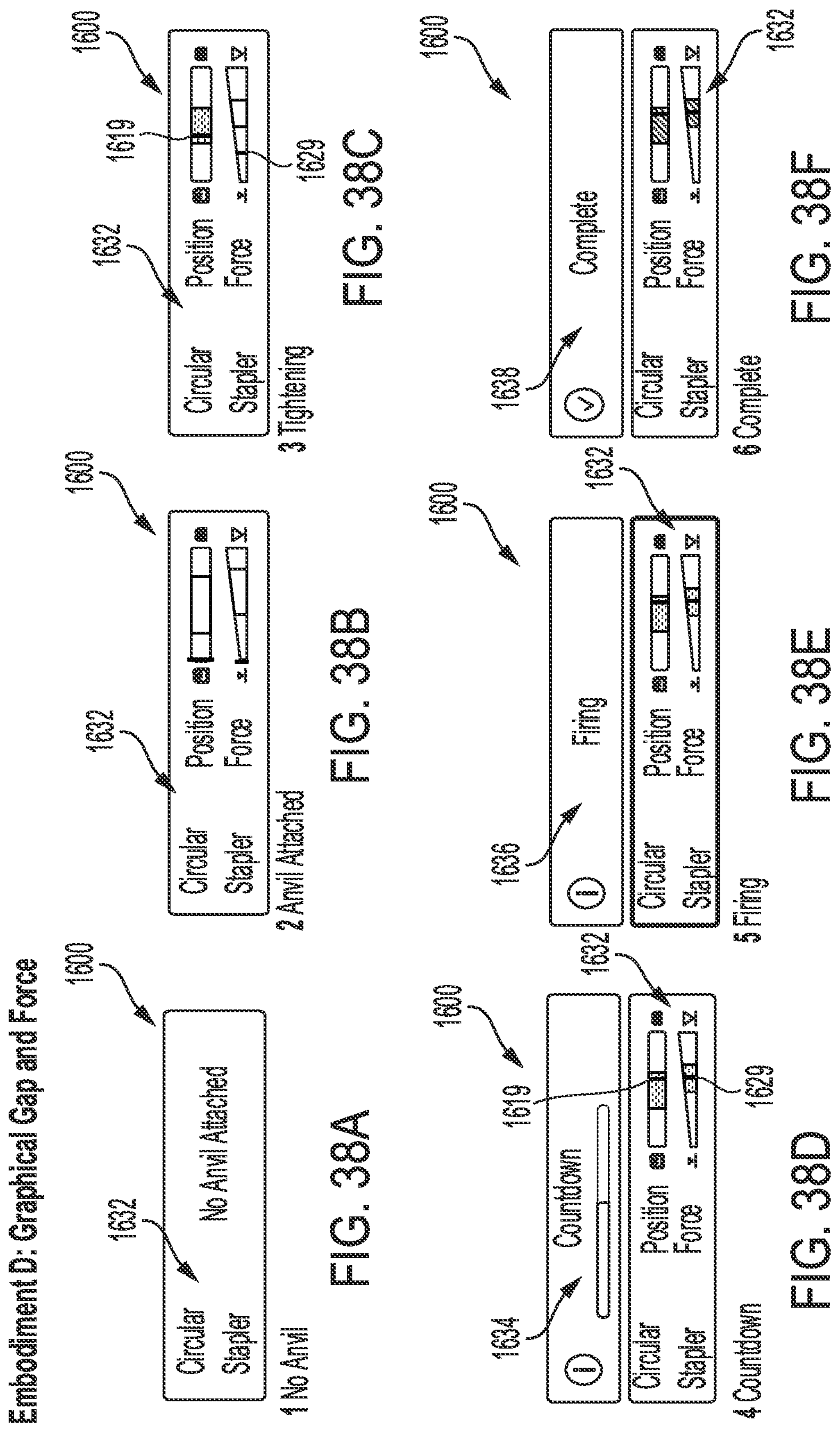
FIGS. 38A-38F illustrate various states of the display of FIGS. 37A and 37B, according to at least one aspect of the present disclosure.

FIG. 38A-38F illustrate various states of the display 1600 to visually communicate information to the user. The states of the display 1600 include when the anvil isn't attached to the trocar (FIG. 38A), when the anvil is attached to the trocar (FIG. 38B), when the position of the anvil is within an acceptable zone for firing the stapler, but the force applied to the tissue is not within an acceptable zone for firing (FIG. 38C), when the user has reached the desired location of the anvil, sufficient force has been applied to the tissue, and a countdown is initiated to allow the tissue to relax prior to firing the staple cartridge (FIG. 38D), when the circular stapler is firing (FIG. 38E), and when firing has been completed (FIG. 38F).

As shown in FIG. 38A, prior to attachment of the anvil 1016 to the trocar 1012, the control system controls the display 1600 into a first state to visually indicate to a user that no anvil 1016 is attached to the trocar 1012, as determined by an anvil connectivity sensor, described elsewhere herein. Upon detecting the connection of the anvil 1016 to the trocar 1012 (via the connectivity sensor, as an example), the control system transitions the display 1600 to a second state to indicate to the user that the anvil 1016 is attached to the trocar 1012. For instance, in some embodiments, in the second state, the control system can display a visual indication of the position of the anvil 1016 relative to the staple cartridge 1017 and/or a visual indication of the force the anvil 1016 is applying to tissue, as described elsewhere herein and also shown in FIG. 38B. Accordingly, the control system does not provide visual feedback with respect to various sensed parameters until the control system detects attachment of the anvil 1016 to the trocar 1012.

In one aspect, when the stapler is not firing, the control system causes a portion 1632 of the display 1600 to illuminate a first color, such as gray, to indicate to a user that the stapler is not firing (FIGS. 38A-38D and 38F). When the stapler is firing (FIG. 38E), the control system causes the portion 1632 to illuminate a second color different than the first color, such as white, to indicate to the user that the stapler is firing.

In various embodiments, the display 1600 displays notifications 1634, 1636, 1638 that provide textual information to a user. In one aspect, the control system causes display 1600 to display a notification 1634 (FIG. 38D) that the countdown has been initiated. In various embodiments, the notification 1634 also includes a bar that visually illustrates the time remaining in the countdown. In one aspect, the control system causes the display 1600 to display a notification 1636 (FIG. 38E) when the stapler is firing. In one aspect, the control system causes the display 1600 to display a notification 1638 (FIG. 38F) when the firing has completed.

Figure 39:
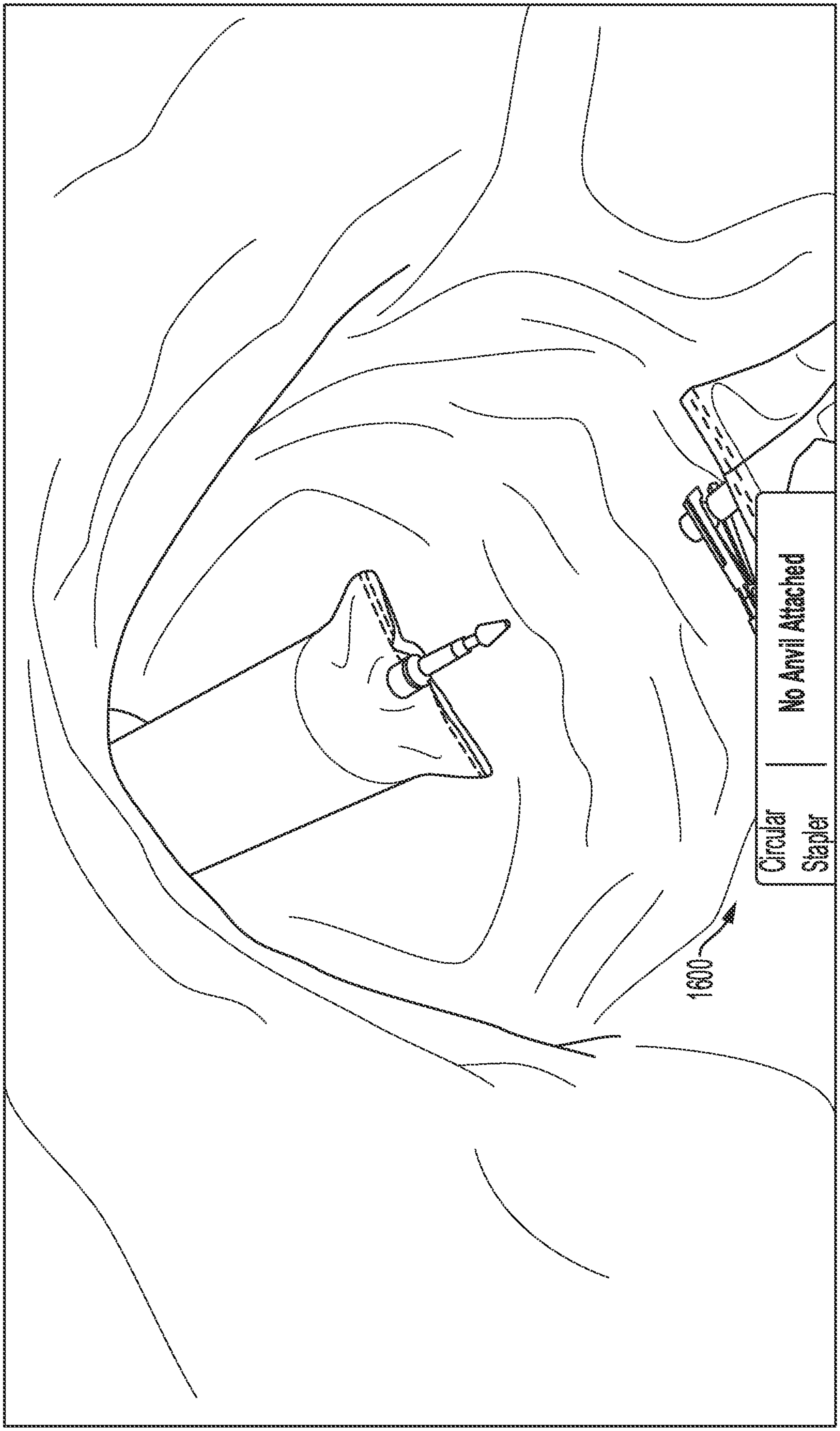
FIGS. 39-45 illustrate an example implementation of the display of FIG. 37, according to at least one aspect of the present disclosure.
Figure 40:
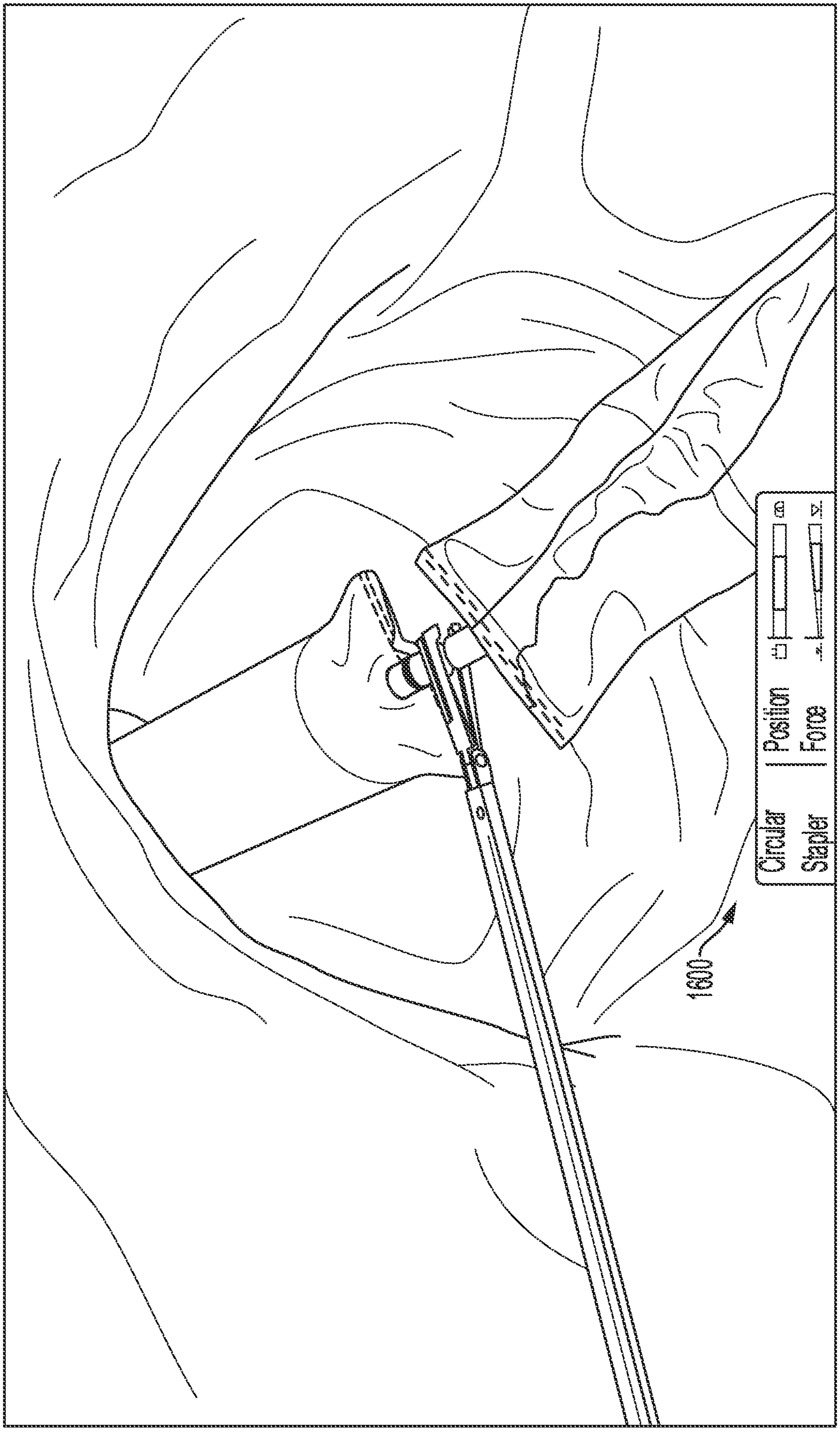
Figure 41:
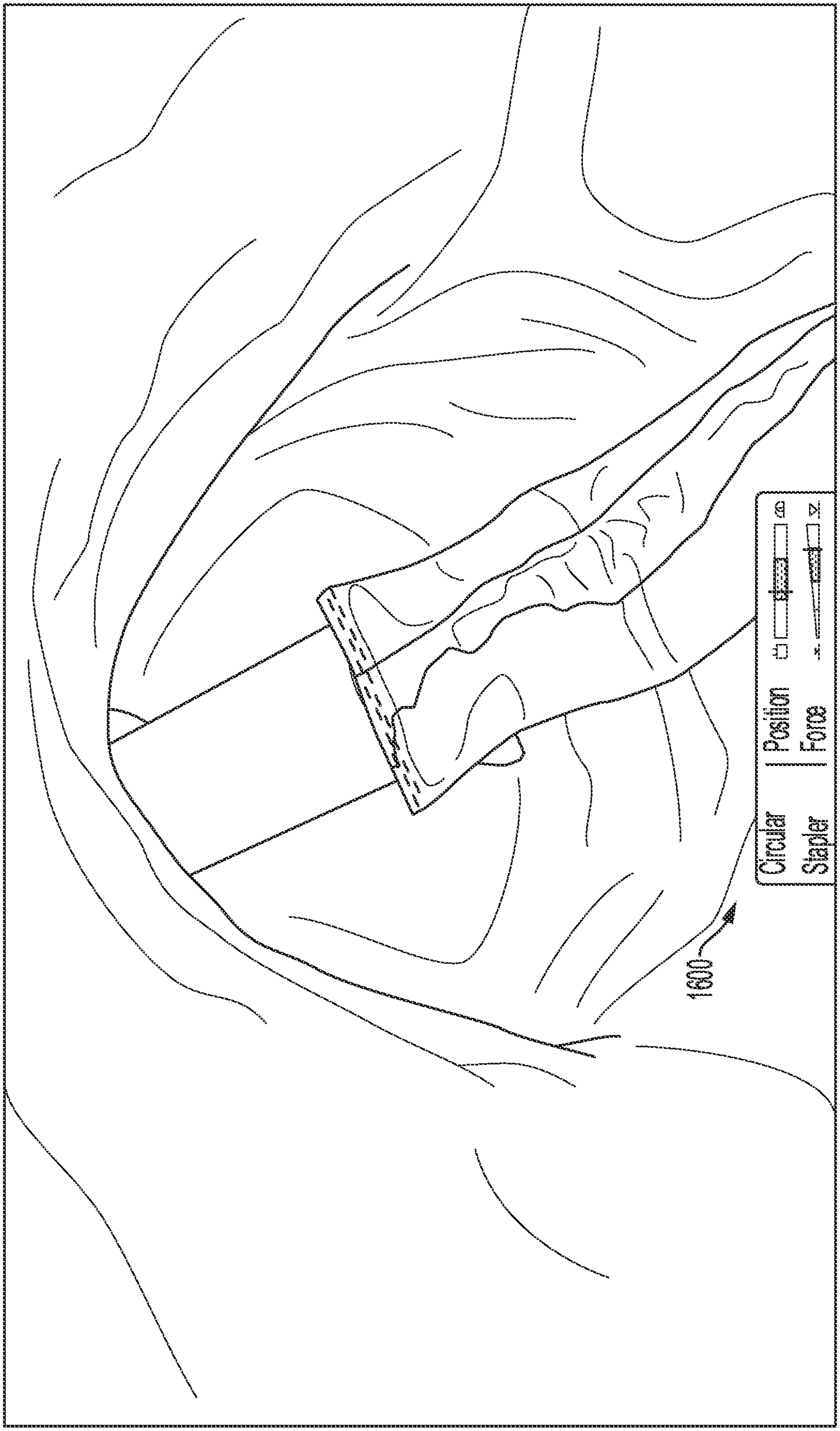
Figure 42:
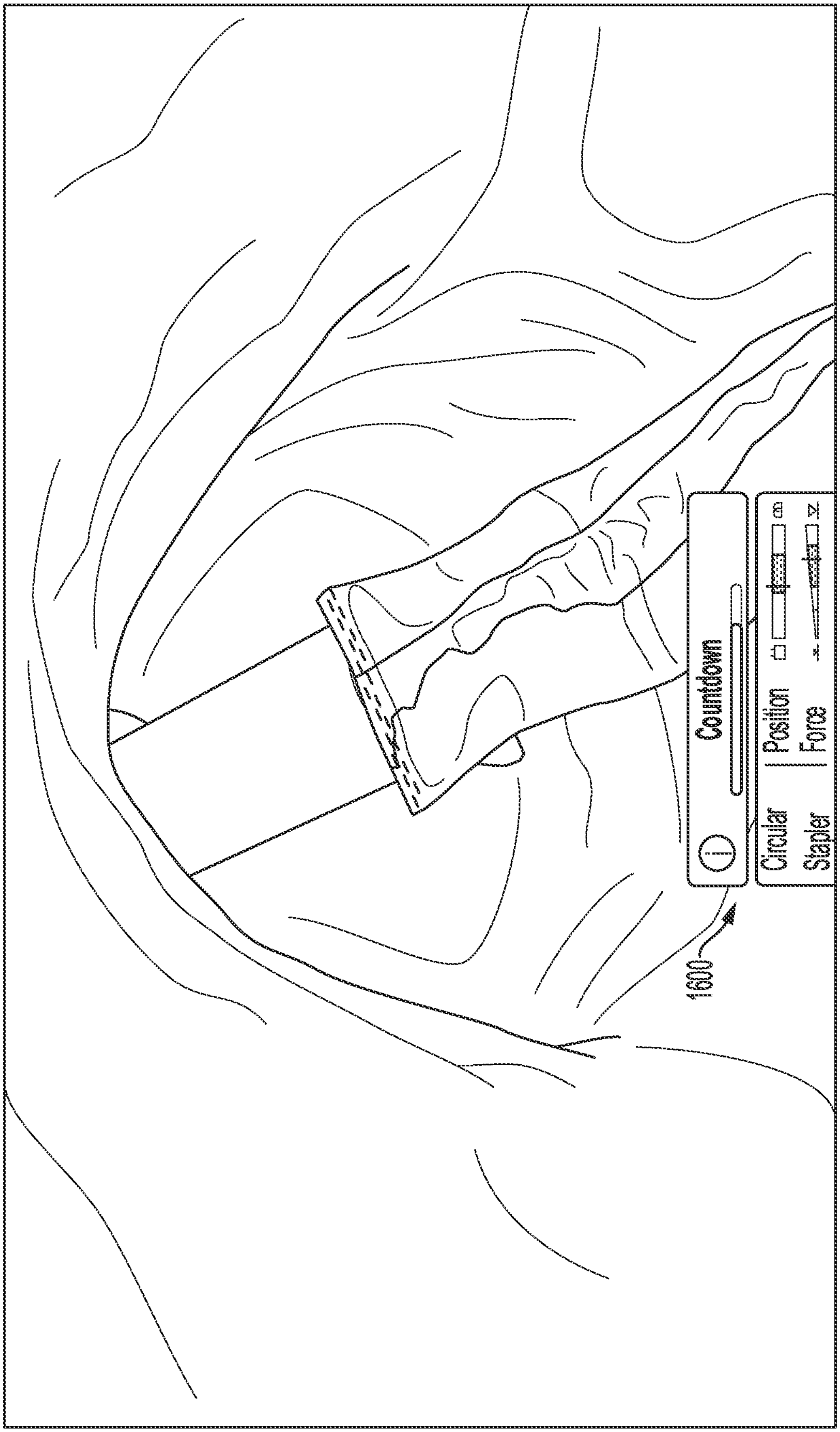
Figure 43:
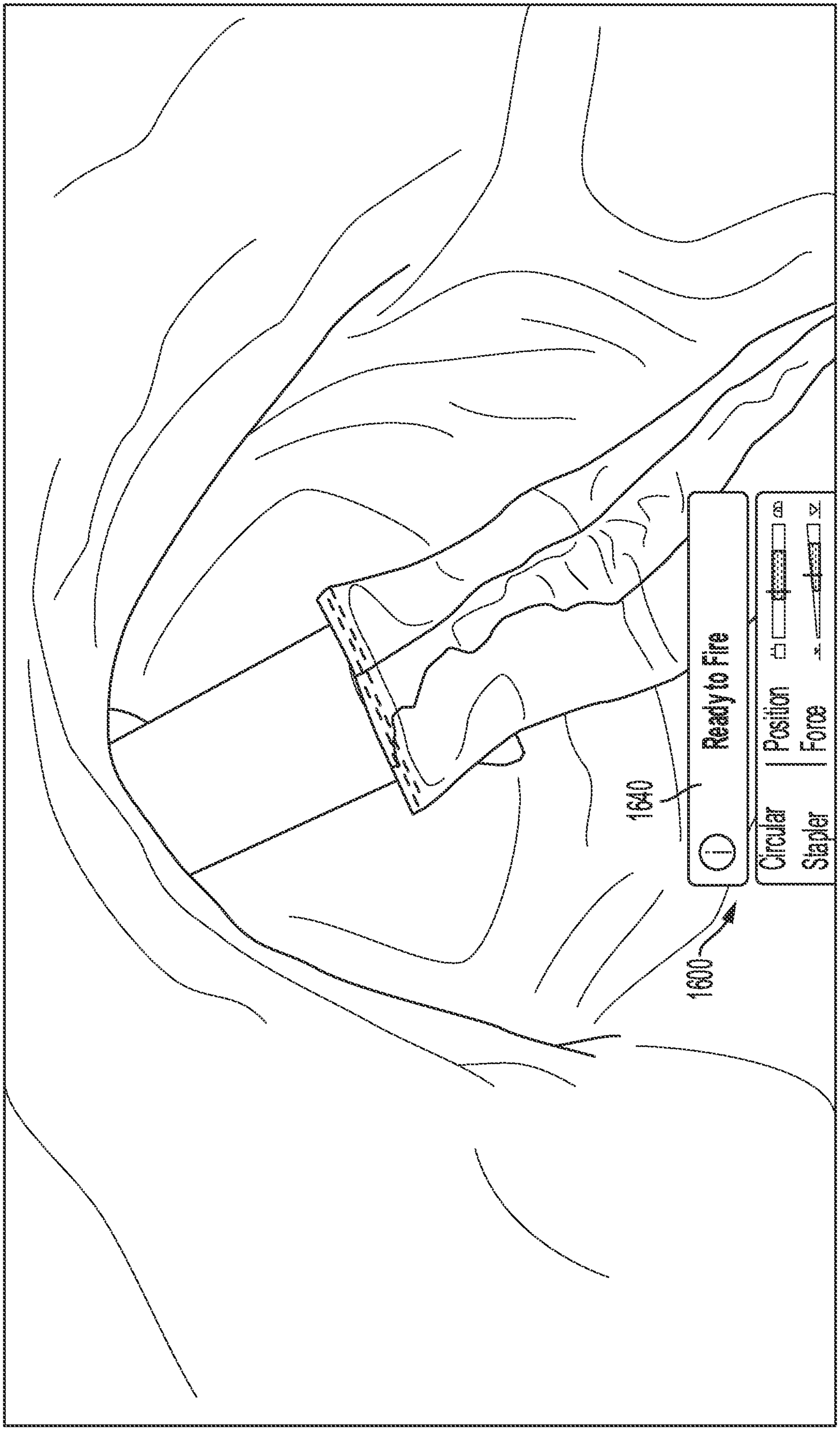
Figure 44:
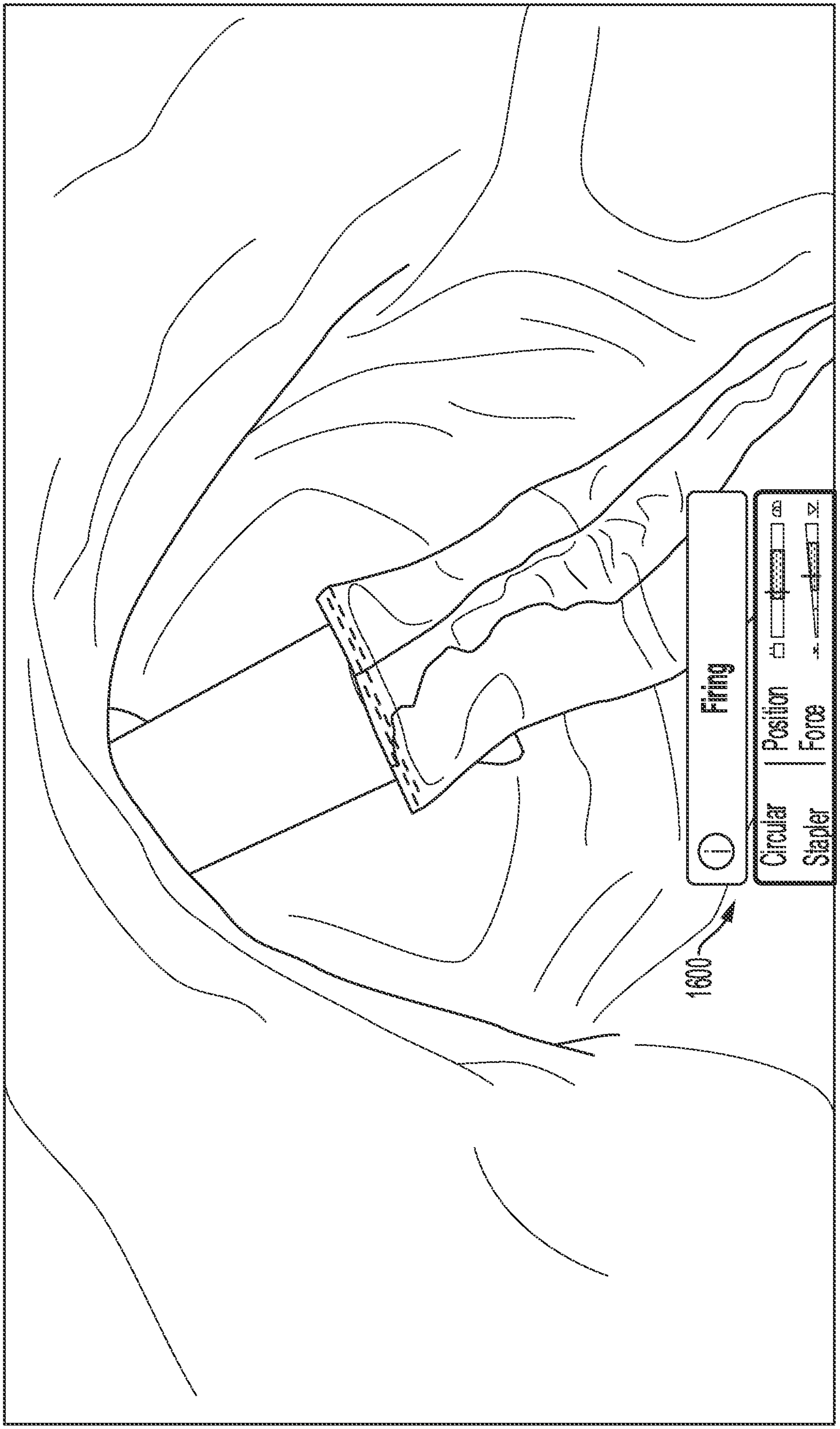
Figure 45:
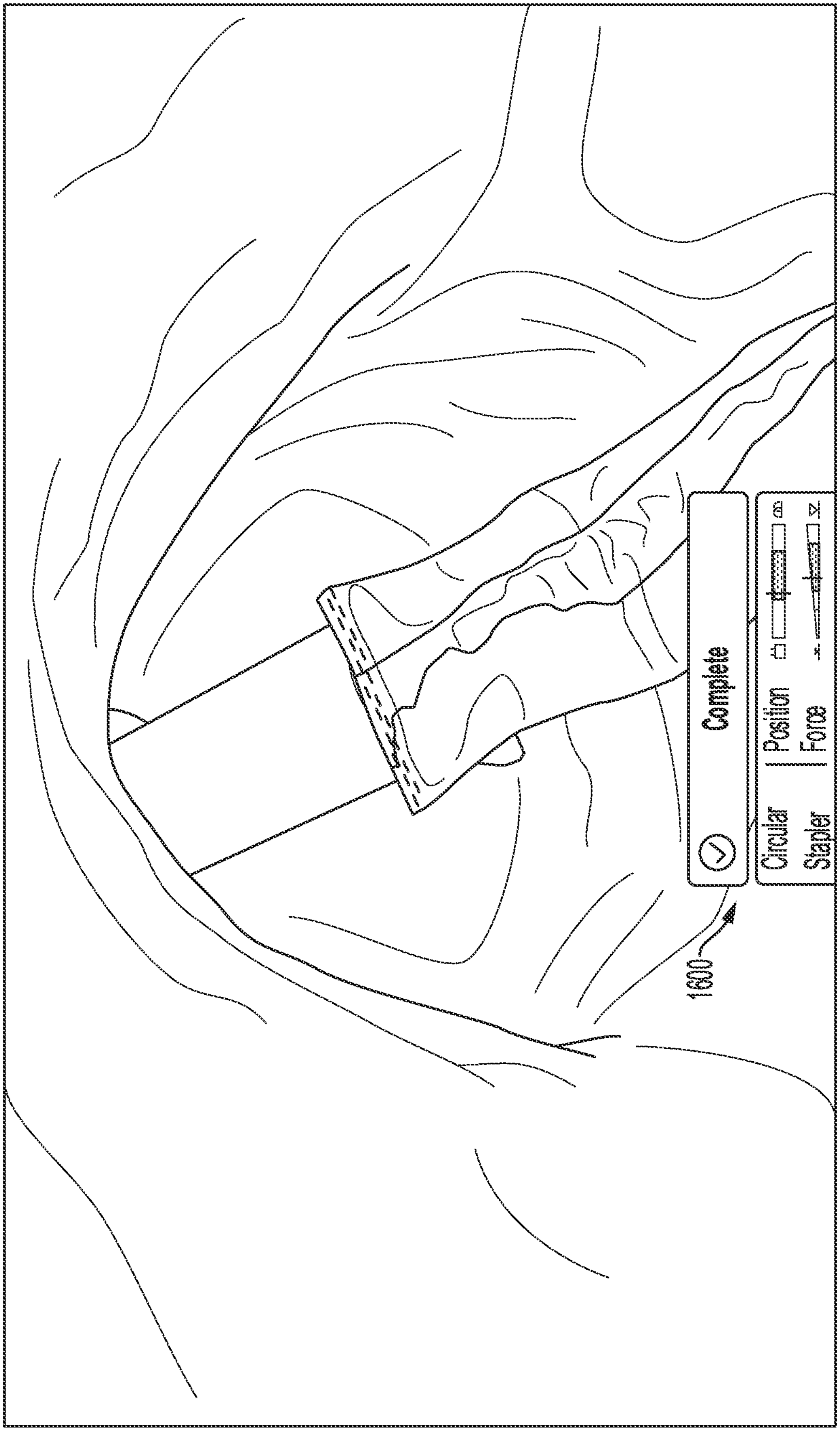

FIGS. 39-45 illustrate an example implementation of the display 1600. Display 1600 is displayed on a display, such as any number of the displays described elsewhere herein. FIG. 39 illustrates the anvil not yet coupled to the trocar, and thus, the display 1600 displays the state of FIG. 38A. FIG. 40 illustrates the anvil coupled to the trocar, and thus, the display 1600 displays the state of FIG. 38B. FIG. 41 illustrates the anvil having reached the acceptable zone for firing, as indicated by first feedback portion 1610, and acceptable force zone for firing, as indicated by the second feedback portion 1620. FIG. 42 illustrates the countdown having been initiated to allow the tissue to relax before firing, and thus, the display 1600 displays the state of FIG. 38D. FIG. 43 illustrates the stapler being in a ready to fire state after completion of the countdown. As can be seen in FIG. 43, the control system causes display 1600 to display notification 1640, indicating that the device is ready to be fired. FIG. 44 illustrates the stapler being fired, and thus, the display 1600 displays the state of FIG. 38E. FIG. 45 illustrates the stapler having completed firing, and thus, the display 1600 displays the state of FIG. 38F.

Embodiment E: Graphic Gap and Graphical Force Feedback

Figure 46:
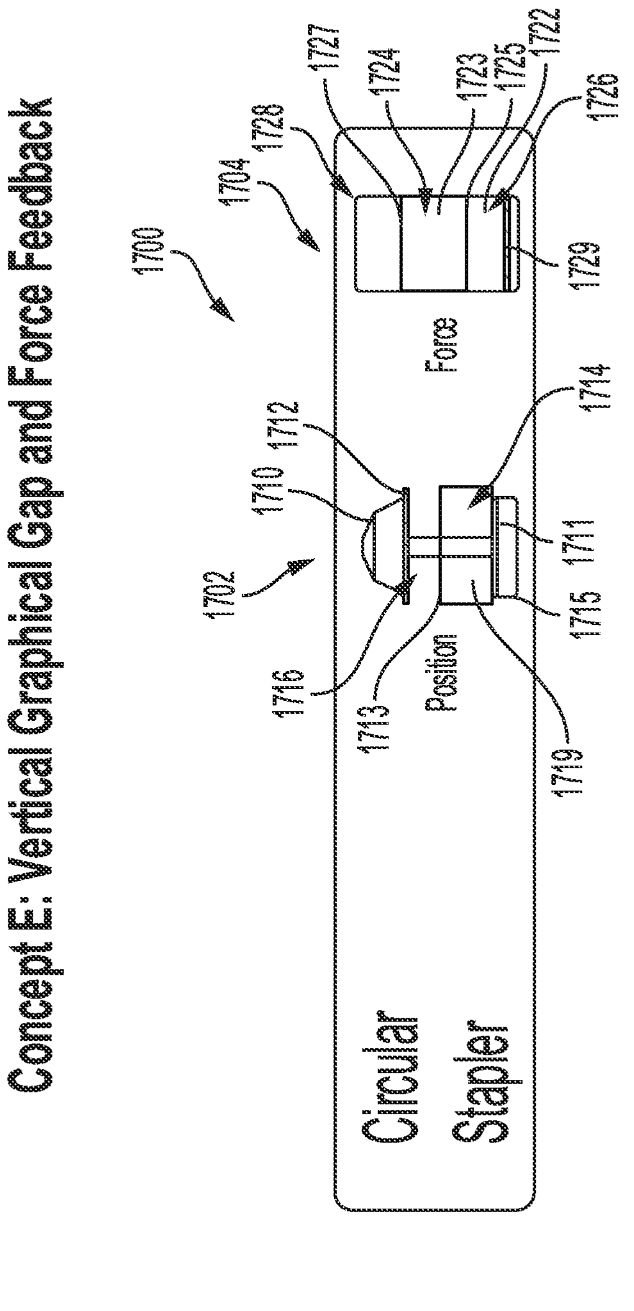
FIG. 46 illustrates a display indicating that an anvil is out of range and that an unacceptable amount of force is being applied to tissue by the anvil according to at least one aspect of the present disclosure.
Figures 47A, 47B, 47C, 47D, 47E, 47F:
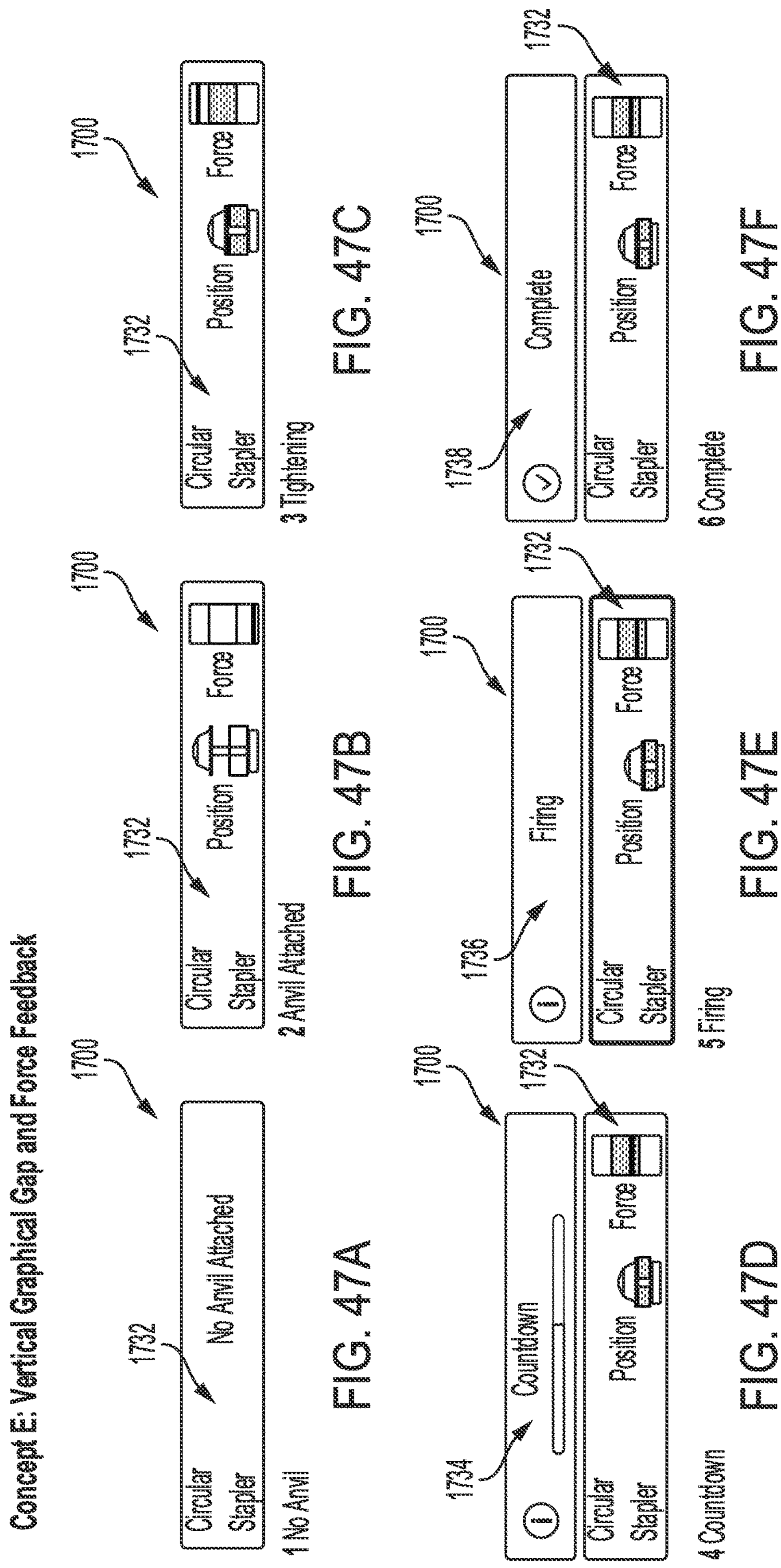
FIGS. 47A-47F illustrate various states of the display of FIG. 46, according to at least one aspect of the present disclosure.

FIG. 46 illustrates a display 1700 for providing visual feedback to a user of a circular stapler, according to at least one aspect of the present disclosure. In various embodiments, the display 1700 is incorporated into the housing 1002 of the circular stapler 1000. In various embodiments, the display 1700 is shown on display 1030. In various other embodiments, the display 1100 is visually displayed on a display, such as display 7, display 9, display 19, within a display of the surgeon console 18, on AR device 66, or any other suitable location described herein that is configured to convey visual information to a user. In various embodiments, the display 1700 is in operable communication with a control system, such as control system 1030, that controls various aspects of the display 1700, as described herein below. In various embodiments, the control system comprises a processor and a memory storing instructions that are executable by the processor. In various embodiments, the control system is any suitable controller, control circuit, hub, or the like described herein. In one aspect, the display 1700 is similar to display 1600.

In one aspect, the first feedback portion 1702 is similar to display 1400. The first feedback portion 1702 provides graphical, visual feedback to a user indicative of the position of the anvil relative to the staple cartridge. In various embodiments, the first feedback portion 1702 is a graphical feedback mechanism that includes a movable indicator 1710 that is a graphical depiction of the anvil and an indicator 1711 that is a graphical depiction of the staple cartridge. In one aspect, the indicator 1710 includes an indicator line 1712 that is a graphic representation of the tissue-contacting surface of the anvil. The first feedback portion 1702 also includes an acceptable zone 1714 that is defined by a threshold boundary 1713 and threshold boundary 1715, both of which are visible to the user. In one aspect, the acceptable zone 1714 corresponds to positions of the anvil relative to the staple cartridge that are suitable for firing staples from the staple cartridge. In one aspect, threshold boundary 1715 is aligned with the boundary of the indicator 1711. Other embodiments are envisioned where the threshold boundary 1715 is offset the boundary of the indicator 1711. In various embodiments, the size of the acceptable zone 1714 and the positions of the threshold boundaries 1713, 1715 are predefined, stored in a memory, and are retrievable by the control system. Various other embodiments are envisioned where the size of the acceptable zone 1714 and the positions of the threshold boundaries 1713, 1715 are set by a user at a user interface.

In some embodiments, when the anvil is initially coupled to the trocar of the surgical instrument, the indicator 1710 on the first feedback portion 1702 indicates that the anvil is outside the acceptable zone 1714, in an unacceptable zone 1716. In various embodiments, the control system detects the attachment of the anvil utilizing any suitable sensors, detectors, or the like, as described elsewhere herein. In various embodiments, the control system detects the attachment of the anvil utilizing an anvil connectivity sensor integrated with the anvil, such as sensor 1044. Accordingly, the control system can communicate with various sensors within the anvil, such as force and/or position sensors, as examples, such that the control circuit can receive, process, and/or wirelessly transmit data from the anvil sensors to other pieces of equipment in the OR for display to users. In one aspect, the control system displays, or illuminates, the indicator line 1712 a first color, such as gray, when the anvil is not coupled to the trocar and displays, or illuminates, the indicator line 1712 a second color different than the first color, such as orange, when the anvil is coupled to the trocar. When the indicator line 1712 of indicator 1710 is within unacceptable zone 1716, this indicates to a user that the anvil is positioned too far away from the staple cartridge, i.e., 'out of range', and that the anvil should be moved closer to the staple cartridge, such as utilizing the manually retraction knob 1013 on the housing or the motorized drive system. When the anvil is within the unacceptable zone 1716, the control system causes a portion 1719 to illuminate a first color, such as gray. In various embodiments, the size of the portion 1719 is defined by boundary lines 1713, 1715. In some embodiments, the control system prevents actuation of the firing drive to deploy the staples from the staple cartridge 1007 based on the determination of the indicator line 1712 being positioned within the unacceptable zone 1716.

When the first feedback portion 1702 indicates that the anvil is within the unacceptable zone 1716, the user can utilize the retraction knob 1013 or motorized system to move the anvil toward the staple cartridge (via trocar). As the user retracts the anvil, the control system detects the movement of the anvil (using any number of position sensors or the like, described elsewhere herein) to cause the indicator 1710, and thus, indicator line 1712, to move toward indicator 1711 to visually communicate to the user that the anvil is approaching acceptable zone 1714. In various embodiments, the circular stapler includes a rotational position sensor, such as sensor 1040, that measures the rotations of the retraction knob 1013 to determine a position of the anvil relative to the staple cartridge. In various embodiments, the circular stapler includes a linear position sensor, such as sensor 1042, to measure movement of various components of the stapler, such as the trocar itself, to determine a position of the anvil relative to the staple cartridge. Once the indicator line 1712 reaches or crosses threshold boundary 1713, indicative of the anvil reaching the acceptable zone 1714, the control system causes the portion 1719 to illuminate a second color different than the first color, such as green, indicating to a user that the anvil is within the acceptable zone 1714, and thus, the stapler can be fired.

As referenced above, the display 1700 also includes a second feedback portion 1720. In one aspect, the second feedback portion 1720 provides visual feedback regarding the amount of force applied to the tissue positioned between the anvil and the staple cartridge. The second feedback portion includes a bar 1722 that defines an acceptable zone 1724 and unacceptable zones 1726, 1728 surrounding the acceptable zone 1724. The unacceptable zone 1726 and the acceptable zone 1724 are separated by threshold boundary 1725 that is visible to the user. Similarly, the unacceptable zone 1728 and the acceptable zone 1724 are separated by threshold boundary 1727 that is visible to the user. In one aspect, the acceptable zone 1724 corresponds to forces that are suitable for firing staples from the staple cartridge. In one aspect, the unacceptable zone 1726 corresponds to forces that are is too low, such as under a threshold limit, and thus, is unacceptable for firing staples. For instance, the anvil may not be applying a sufficient force to the tissue to enable to staples to properly form and seal the tissue. In one aspect, the unacceptable zone 1728 corresponds to forces that are too high, such as over a threshold limit, and thus, is unacceptable for firing staples. For instance, the anvil may be applying too much force to the tissue and thus, may damage the tissue. In various embodiments, the size of the zones 1724, 1726, 1728 and the positions of threshold boundaries 1725, 1727 are predefined, stored in a memory, and are be retrievable by the control system. Various other embodiments are envisioned where the size of the zones 1724, 1726, 1728 and the positions of threshold boundaries 1725, 1727 are set by a user at a user interface.

The second feedback portion 1720 also includes an indicator 1729 that moves along the bar 1722 to visually illustrate how much force is being applied to the tissue via zones 1724, 1726, 1728. In various embodiments, the force is determined in any suitable manner known in the art, such as with a force sensor, a strain gauge, or with any other suitable sensor of sensing the force, as described elsewhere herein. In various embodiments, a torque sensor is integrated with the rotation knob 1013 of the circular stapler to measure the torque a user applies. In various embodiment, a force sensor is integrated with the internal shaft of the stapler that drives the trocar, or within the trocar itself, for measuring the force the shaft experiences. In various embodiments, the anvil includes a force sensor for measuring the force applied to the tissue. In one aspect, the control system can communicate with the anvil utilizing an anvil connectivity sensor integrated with the anvil, such as sensor 1044 such that the control system can interrogate and receive data from the force sensor. With the determined force, the control system controls a position of the indicator 1729 to visually illustrate which force zone 1724, 1726 1728 to position the indicator 1729 within.

In some embodiments, when the anvil is initially coupled to the trocar of the surgical instrument, the control system detects that the anvil is not yet applying a force to the tissue, and thus, causes the indicator 1729 on the second feedback portion 1720 to be positioned within the unacceptable zone 1726, as shown in FIG. 46. The indicator 1729 pointing to the unacceptable zone 1726 indicates to a user that the anvil should be moved closer to the staple cartridge to apply additional force to the tissue, such as utilizing the manually retraction knob 1013 on the housing or the motorized system. When the anvil is within one of unacceptable zones 1726, 1728, a portion 1723 of the bar 1722 displays, or illuminates, a first color, such as gray, to indicate that the stapler is not ready for firing. In some instances, the size of the portion 1723 is defined by threshold boundaries 1725, 1727. In some embodiments, the control system prevents actuation of the firing drive to deploy the staples from the staple cartridge 1007 based on the determination of the indicator 1729 being positioned within one of the unacceptable zones 1726, 1728.

When the second feedback portion 1704 indicates that too little force is being applied to the tissue, by way of indicator 1729 being positioned within unacceptable zone 1726, the user can utilize the retraction knob 1013 to move the anvil toward the staple cartridge (via trocar) to apply additional force to the tissue. As the user retracts the anvil, the control system detects the increase in force (using any number of force sensors or the like, described elsewhere herein) to cause the indicator 1729 to move along bar 1722 to visually communicate to the user that the force applied to the tissue is approaching acceptable zone 1724. Once the indicator 1729 has reached the acceptable zone 1724, the portion 1723 of the bar 1722 displays, or illuminates, a second color different than the first color, such as green, indicating to a user that a sufficient amount of force is being applied to the tissue, and thus, the stapler can be fired.

FIGS. 47A-47F illustrate various states of the display 1700 to visually communicate information to the user. The states of the display 1700 include when the anvil isn't attached to the trocar (FIG. 47A), when the anvil is attached to the trocar (FIG. 47B), when the position of the anvil is moving toward the acceptable zone 1724, but still within unacceptable zone 1726, and the force applied to the tissue is within unacceptable zone 1728, i.e., too much force applied (FIG. 47C), when the user has reached the desired location of the anvil, sufficient force has been applied to the tissue, and a countdown is initiated to allow the tissue to relax prior to firing the staple cartridge (FIG. 47D), when the circular stapler is firing (FIG. 47E), and when firing has been completed (FIG. 46F).

In one aspect, when the stapler is not firing, the control system causes a portion 1732 of the display 1700 to illuminate a first color, such as gray, to indicate to a user that the stapler is not firing (FIGS. 47A-47D and 47F). When the stapler is firing (FIG. 47E), the control system causes the portion 1732 to illuminate a second color different than the first color, such as white, to indicate to the user that the stapler is firing.

In various embodiments, the display 1700 displays notifications 1734, 1736, 1738 that provide textual information to a user. In one aspect, the control system causes display 1700 to display a notification 1734 (FIG. 47D) that the countdown has been initiated. The notification 1734 also includes a bar that visually illustrates the time remaining in the countdown. In one aspect, the control system causes display 1700 to display a notification 1736 (FIG. 47E) when the stapler is firing. In one aspect, the control system causes display 1700 to display a notification 1738 (FIG. 47F) when the firing has completed.

Figure 48:
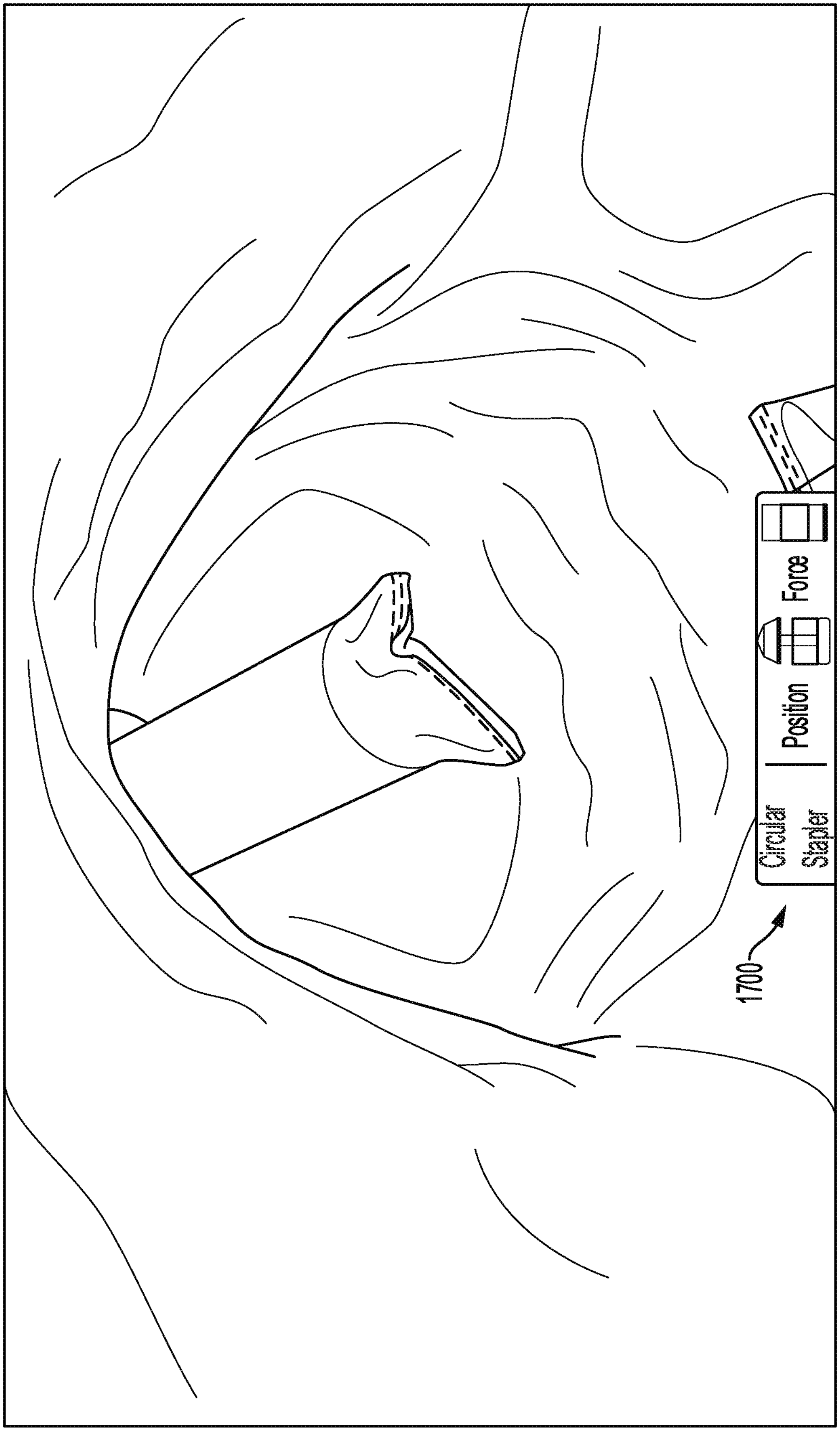
FIGS. 48 and 49 illustrate an example implementation of the display of FIG. 46, according to at least one aspect of the present disclosure.
Figure 49:
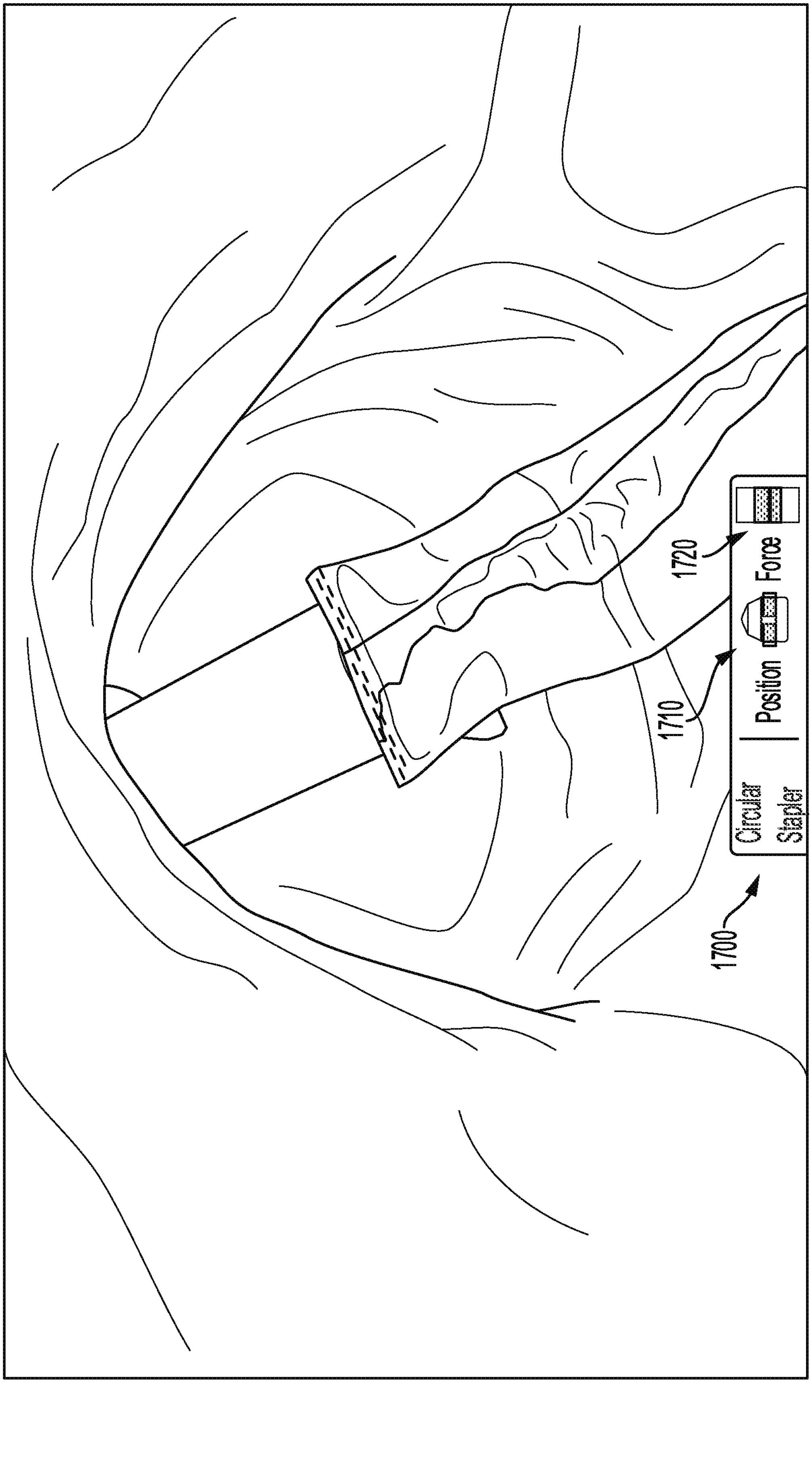

FIGS. 48 and 49 illustrate an example implementation of the display 1700. Display 1700 is displayed on a display, such as any number of the displays described elsewhere herein. FIG. 48 illustrates the anvil not yet coupled to the trocar, and thus, the display 1700 displays the state of FIG. 47B. In other instances, when the anvil is not yet coupled to the trocar, the display 1700 can display the state of FIG. 47A. FIG. 49 illustrates the anvil having reached the acceptable zone for firing, as indicated by first feedback portion 1702, and acceptable force zone for firing, as indicated by the second feedback portion 1704.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of this disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, logic diagrams, and/or examples. Insofar as such block diagrams, logic diagrams, and/or examples contain one or more functions and/or operations, it will be understood by those within the art that each function and/or operation within such block diagrams, logic diagrams, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" or "control system" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a control circuit, computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

It is worthy to note that any reference numbers included in the appended claims are used to reference exemplary embodiments/elements described in the present disclosure.

Accordingly, any such reference numbers are not meant to limit the scope of the subject matter recited in the appended claims.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical stapler, comprising:

an end effector configured to receive a staple cartridge including staples;

a trocar movable relative to the end effector;

an anvil removably coupleable to the trocar, wherein the anvil is movable relative to the end effector based on movement of the trocar, and wherein the anvil is configured to apply a force to tissue positioned between the anvil and the end effector;

a position sensor configured to sense a position of the anvil relative to the end effector;

a force sensor configured to sense the force that is applied to the tissue;

a firing drive to fire the staples;

a housing comprising a display; and a control circuit operably coupled to the position and force sensors and the display, wherein the control circuit is configured to:

interrogate the position sensor to determine the position of the anvil;

interrogate the force sensor to determine the force; and display a representation of the determined position and force on the display, wherein the representation comprises a visual guide, defining:

a first unacceptable zone corresponding to positions of the anvil that are unacceptable for firing staples from the staple cartridge;

a first acceptable zone corresponding to positions of the anvil that are acceptable for firing staples from the staple cartridge;

a second unacceptable zone corresponding to forces that are unacceptable for firing staples from the staple cartridge; and a second acceptable zone corresponding to forces that are acceptable for firing staples from the staple cartridge;

a first position indicator configured to traverse the visual guide to a position that represents the determined position; and a second force indicator configured to traverse the visual guide to a position that represents the determined force;

initiate a countdown based on the position indicator moving within the first acceptable zone and the force indicator moving within the second acceptable zone, display a firing readiness indicator based on a completion of the countdown allow the firing drive to fire the staples from the staple cartridge based; on the completion of the countdown; and prevent the firing drive from firing the staples from the staple cartridge based on the position indicator being located within the first unacceptable zone or the force indicator being within the second unacceptable zone or a combination thereof;

wherein the visual guide comprises a first bar and a second bar. and wherein the first position indicator is movable along the first bar, and wherein the second force indicator is movable. along the second bar.

2. The surgical stapler of claim 1, wherein the housing comprises a rotary actuator configured to move the trocar relative to the end effector, and wherein the rotary actuator comprises the position sensor.

3. The surgical stapler of claim 1, wherein the trocar comprises the position sensor.

4. The surgical stapler of claim 1, wherein the housing comprises a handle.

5. The surgical stapler of claim 1, wherein the representation comprises a numerical representation.

6. The surgical stapler of claim 1, wherein the first bar defines a portion, and wherein the control circuit is further configured to:

display a first color in the portion based on the first position indicator indicating that the determined position is within the first unacceptable zone; and display a second color in the portion based on the first position indicator indicating that the determined position is within the first acceptable zone.

7. A surgical stapler, comprising:

an end effector configured to receive a staple cartridge including staples;

a trocar movable relative to the end effector;

an anvil removably coupleable to the trocar, wherein the anvil is movable relative to the end effector based on movement of the trocar, and wherein the anvil is configured to apply a force to tissue positioned between the anvil and the end effector;

a firing drive to fire the staples;

a first sensor configured to sense attachment of the anvil with the trocar;

a second sensor configured to sense a position of the anvil relative to the end effector;

a third sensor configured to sense the force that is applied to the tissue;

a housing comprising a display; and a control circuit operably coupled to the first sensor, the second sensor, the third sensor and the display, wherein the control circuit is configured to:

interrogate the first sensor to determine that the anvil is coupled to trocar;

interrogate the second sensor to determine the position of the anvil;

interrogate the third sensor to determine the force; and display a representation on the display that the anvil is coupled to the trocar;

display a first position indicator representing the position of the anvil, wherein the first position indicator is movable along a first visual guide, wherein the first visual guide comprises a first acceptable zone corresponding to positions of the anvil that are acceptable for firing staples from the staple cartridge and a first unacceptable zone corresponding to positions of the anvil that are unacceptable for firing staples from the staple cartridge;

display a second force indicator representing the force, wherein the second force indicator is movable along a second visual guide, wherein the second visual guide comprises a second acceptable zone corresponding to forces are acceptable for firing staples from the staple cartridge and a second unacceptable zone corresponding to forces that are unacceptable for firing staples from the staple cartridge;

initiate a countdown based on the position indicator moving within the first acceptable zone and the force indicator moving within the second acceptable zone;

display a firing readiness indicator based on a completion of the countdown;

allow the firing drive to fire the staples from the staple cartridge based on the completion of the countdown; and prevent the firing drive from firing the staples from the staple cartridge based on the position indicator being within the first unacceptable zone and the force indicator being in the second unacceptable zone or a combination thereof.

8. The surgical stapler of claim 7, wherein the display is configurable between:

a first state in which the display indicates that no anvil is coupled to the trocar; and a second state in which the display indicates that the anvil is coupled to the trocar;

wherein the representation comprises transitioning the display to the second state.

9. The surgical stapler of claim 7, wherein the housing comprises a handle.

10. The surgical stapler of claim 1, wherein the housing further comprises a rotary actuator in communication with the trocar and actuatable to move the anvil relative to the end effector, and wherein the control circuit is configured to display a representation of the determined position and force on the display based on actuation of the rotary actuator and prior to the firing drive firing the staples.

* * * * *